United States Patent
Yivgi Ohana et al.

(10) Patent No.: US 12,329,781 B2
(45) Date of Patent: Jun. 17, 2025

(54) MITOCHONDRIAL AUGMENTATION THERAPY OF RENAL DISEASES

(71) Applicant: Minovia Therapeutics Ltd., Tirat Hacarmel (IL)

(72) Inventors: Natalie Yivgi Ohana, Haifa (IL); Uriel Halavee, Tel Aviv (IL); Shmuel Bukshpan, Ramat Hasharon (IL); Moriya Blumkin, Tel Aviv (IL); Noa Sher, Haifa (IL)

(73) Assignee: Minovia Therapeutics Ltd., Tirat Hacarmel (IL)

(*) Notice: Subject to any disclaimer, the term of this patent is extended or adjusted under 35 U.S.C. 154(b) by 1148 days.

(21) Appl. No.: 17/251,666

(22) PCT Filed: Jul. 22, 2019

(86) PCT No.: PCT/IL2019/050821
§ 371 (c)(1),
(2) Date: Dec. 11, 2020

(87) PCT Pub. No.: WO2020/021534
PCT Pub. Date: Jan. 30, 2020

(65) Prior Publication Data
US 2021/0275587 A1  Sep. 9, 2021

Related U.S. Application Data

(60) Provisional application No. 62/753,934, filed on Nov. 1, 2018, provisional application No. 62/701,783, filed on Jul. 22, 2018.

(51) Int. Cl.
A61K 35/15  (2025.01)
A61K 35/17  (2025.01)
(Continued)

(52) U.S. Cl.
CPC .............. A61K 35/15 (2013.01); A61K 35/17 (2013.01); A61K 35/18 (2013.01); A61K 35/19 (2013.01);
(Continued)

(58) Field of Classification Search
CPC ........ A61K 35/17; A61K 35/15; A61K 35/18; A61K 35/19; A61K 35/28; A61K 35/33;
(Continued)

(56) References Cited

U.S. PATENT DOCUMENTS 6,590,141 B1  7/2003  Frohberg
6,616,926 B1  9/2003  Burkly et al.
(Continued)

FOREIGN PATENT DOCUMENTS

AU  2012201710 B2  1/2014
CN  102266350 A  12/2011
(Continued)

OTHER PUBLICATIONS

Rötig, Agnès, et al. "Spectrum of mitochondrial DNA rearrangements in the Pearson marrow-pancreas syndrome." Human molecular genetics 4.8 (1995): 1327-1330. (Year: 1995).*
(Continued)

*Primary Examiner* — Tracy Vivlemore
*Assistant Examiner* — Thomas R. Amick
(74) *Attorney, Agent, or Firm* — The Roy Gross Law Firm, LLC; Roy D. Gross

(57) ABSTRACT

The present invention provides stem cells enriched with healthy functional mitochondria, pharmaceutical compositions comprising these cells and methods of use thereof for treating renal diseases, disorders and symptoms thereof where the disease may or may not be associated with acquired mitochondrial dysfunction.

21 Claims, 16 Drawing Sheets

(51) Int. Cl.
  *A61K 35/18* (2015.01)
  *A61K 35/19* (2015.01)
  *A61K 35/28* (2015.01)
  *A61K 35/33* (2015.01)
  *A61K 35/35* (2015.01)
  *A61K 35/545* (2015.01)

(52) U.S. Cl.
  CPC .............. *A61K 35/28* (2013.01); *A61K 35/33* (2013.01); *A61K 35/35* (2013.01); *A61K 35/545* (2013.01)

(58) Field of Classification Search
  CPC ...... A61K 35/35; A61K 35/545; A61K 35/38; A61P 13/00
  See application file for complete search history.

(56) References Cited

U.S. PATENT DOCUMENTS

| | | | |
|---|---|---|---|
| 6,929,806 | B2 | 8/2005 | Toba et al. |
| 7,238,727 | B2 | 7/2007 | Satomi et al. |
| 7,279,326 | B2 | 10/2007 | Weissig et al. |
| 7,339,090 | B2 | 3/2008 | Christmann |
| 7,407,800 | B1 | 8/2008 | Benton et al. |
| 9,603,872 | B2 | 3/2017 | Cataldo et al. |
| 10,213,459 | B2 | 2/2019 | Yivgi-Ohana et al. |
| 10,738,278 | B2 | 8/2020 | Mohler et al. |
| 2001/0021526 | A1 | 9/2001 | Davis et al. |
| 2003/0113389 | A1 | 6/2003 | Wang et al. |
| 2004/0122109 | A1 | 6/2004 | Fujii et al. |
| 2004/0192627 | A1 | 9/2004 | Weissig et al. |
| 2005/0153381 | A1 | 7/2005 | Marusich et al. |
| 2005/0164933 | A1 | 7/2005 | Tymianski et al. |
| 2006/0024277 | A1 | 2/2006 | Sivak et al. |
| 2006/0241034 | A1 | 10/2006 | Chauvier et al. |
| 2008/0057039 | A1 | 3/2008 | Newell Rogers et al. |
| 2010/0278790 | A1 | 11/2010 | Prockop et al. |
| 2011/0008310 | A1 | 1/2011 | Cataldo et al. |
| 2011/0105359 | A1 | 5/2011 | Czerwinski |
| 2012/0058091 | A1 | 3/2012 | Rogers et al. |
| 2012/0107285 | A1 | 5/2012 | Hyde et al. |
| 2012/0107937 | A1 | 5/2012 | Hyde et al. |
| 2013/0022666 | A1 | 1/2013 | Brzezinska |
| 2013/0034527 | A1 | 2/2013 | Hyde et al. |
| 2013/0149778 | A1 | 6/2013 | Chang et al. |
| 2014/0193511 | A1 | 7/2014 | Yivgi-Ohana et al. |
| 2015/0045403 | A1 | 2/2015 | Shanler et al. |
| 2015/0079193 | A1 | 3/2015 | Yivgi-Ohana et al. |
| 2015/0313950 | A1 | 11/2015 | Gammelsaeter et al. |
| 2015/0344844 | A1 | 12/2015 | Better et al. |
| 2015/0374736 | A1 | 12/2015 | Lee |
| 2015/0374756 | A1 | 12/2015 | Frank et al. |
| 2016/0346333 | A1 | 12/2016 | Hariri |
| 2017/0015287 | A1 | 1/2017 | Sander et al. |
| 2017/0065635 | A1 | 3/2017 | Cataldo et al. |
| 2017/0080030 | A1 | 3/2017 | Peirce-Cottler et al. |
| 2017/0151287 | A1 | 6/2017 | Von Maltzahn et al. |
| 2017/0204372 | A1 | 7/2017 | Mohler et al. |
| 2018/0007913 | A1 | 1/2018 | Sceats et al. |
| 2018/0030413 | A1 | 2/2018 | Yivgi-Ohana et al. |
| 2020/0009198 | A1 | 1/2020 | Choi et al. |
| 2020/0054682 | A1 | 2/2020 | Gojo et al. |
| 2020/0239850 | A1 | 7/2020 | Yivgi-Ohana et al. |
| 2020/0246379 | A1 | 8/2020 | Yivgi-Ohana et al. |
| 2020/0377951 | A1 | 12/2020 | Bettoun |
| 2021/0260137 | A1 | 8/2021 | Yivgi-Ohana et al. |
| 2023/0338427 | A1 | 10/2023 | Yivgi-Ohana et al. |

FOREIGN PATENT DOCUMENTS

| | | |
|---|---|---|
| CN | 102293178 A | 12/2011 |
| CN | 103976935 A | 8/2014 |
| CN | 106795490 A | 5/2017 |
| DE | 102013225588 A1 | 4/2014 |
| GB | 2350565 A | 12/2000 |
| JP | 2002523434 A | 7/2002 |
| JP | 2004500409 A | 1/2004 |
| JP | 2006131600 A | 5/2006 |
| JP | 2008545779 A | 12/2008 |
| JP | 2014501764 A | 1/2014 |
| JP | 2018-507690 | 3/2018 |
| WO | WO 2003/014317 A2 | 2/2003 |
| WO | WO-2004100773 A2 | 11/2004 |
| WO | WO-2008000001 A1 | 1/2008 |
| WO | WO-2008137035 A1 | 11/2008 |
| WO | WO-2008152640 A2 | 12/2008 |
| WO | WO-2011059547 A2 | 5/2011 |
| WO | WO-2013002880 A1 | 1/2013 |
| WO | WO-2013035101 A1 | 3/2013 |
| WO | WO 2013/082243 A1 | 6/2013 |
| WO | WO-2013171752 A1 | 11/2013 |
| WO | WO 2014/130518 A1 | 8/2014 |
| WO | WO 2016/008937 A1 | 1/2016 |
| WO | WO-2016049867 A1 | 4/2016 |
| WO | WO 2016/076434 A1 | 5/2016 |
| WO | WO 2016/113544 A1 | 7/2016 |
| WO | WO 2016/135723 A1 | 9/2016 |
| WO | WO-2016138420 A1 | 9/2016 |
| WO | WO-2017124037 A1 | 7/2017 |
| WO | WO 2018/083700 A1 | 5/2018 |
| WO | WO-2018088874 A1 | 5/2018 |
| WO | WO 2018/101708 | 6/2018 |
| WO | WO 2018/101708 A1 | 6/2018 |
| WO | WO-2018178970 A1 | 10/2018 |
| WO | WO 2020/021535 A1 | 1/2020 |
| WO | WO 2020/021536 A1 | 1/2020 |
| WO | WO 2020/021537 A1 | 1/2020 |
| WO | WO 2020/021538 A1 | 1/2020 |
| WO | WO 2020/021539 A1 | 1/2020 |
| WO | WO 2020/021541 A1 | 1/2020 |
| WO | WO-2020036973 A1 | 2/2020 |
| WO | WO 2020/021540 A9 | 4/2020 |
| WO | WO-2020021541 A9 | 2/2021 |
| WO | WO-2021199040 A1 | 10/2021 |

OTHER PUBLICATIONS

Niyazov, Dmitriy M et al. "Primary Mitochondrial Disease and Secondary Mitochondrial Dysfunction: Importance of Distinction for Diagnosis and Treatment." Molecular syndromology vol. 7,3 (2016): 122-37 (Year: 2016).*

Zhan, Ming et al. "Mitochondrial dynamics: regulatory mechanisms and emerging role in renal pathophysiology." Kidney international vol. 83,4 (2013): 568-81 (Year: 2013).*

Wang, Jingyu et al. "Stem cell-derived mitochondria transplantation: a novel strategy and the challenges for the treatment of tissue injury." Stem cell research & therapy vol. 9,1 106. Apr. 13, 2018 (Year: 2018).*

Augustyniak et al., "Mitochondrial Biogenesis and Neural Differentiation of Human iPSC is Modulated by Idebenone in a Developmental Stage-Dependent Manner," Biogerontology, 2017, 18: 665-677.

CN Office Action in Chinese Application No. 201980054078.2, dated Oct. 27, 2023, 9 pages (with English translation).

Shi et al., "Intravenous administration of mitochondria for treating experimental Parkinson's disease", Mitochondrion, Feb. 2017, 34: 91-100.

Abramova N.B., et al., "Injection of Mitochondria Into Oocytes and Fertilized Eggs," Ontogenez, 1979, vol. 10, No. 4, pp. 401-405 (Translated abstract), 1 Page.

Abramova N.B., et al., "Regulation of the Number and Function of Mitochondria During Artificial Increase of their Mass in Fish Embryos," Biokhimiia, PMID: 6626595, Aug. 1983, vol. 48, No. 8, 1 Page, (Translated Abstract).

Abramova N.B., et al., "The Functioning of Mammalian Mitochondria Injected Into Fish Embryos," Ontogenez, PMID: 2549481, vol. 20, No. 3, May-Jun. 1989, 1 Page, (Translated Abstract).

Alaynick W.A., et al., "Nuclear Receptors, Mitochondria And Lipid Metabolism," Mitochondrion, Sep. 30, 2008, vol. 8, No. 4, pp. 329-337, 17 Pages DOI: 10.1016/j.mito.2008.02.001, XP025474006.

(56) References Cited

OTHER PUBLICATIONS

Babenko V.A., "Mirol Enhances Mitochondria Transfer from Multipotent Mesenchymal Stem Cells (MMSC)to Neural Cells and Improves the Efficacy of Cell Recovery," Molecules, Mar. 19, 2018, vol. 23, No. 3, 14 pages.
Baker et al., "Use of the Mouse Aortic Ring Assay to Study Angiogenesis," 2012, Nature Protocols 7(1): 89-104.
Biolog, "MitoPlate™ S-1 and MitoPlate™ I-1 for Characterization of Mammalian Cell Mitochondria," 2020, pp. 1-12.
Bourgeron T., et al., "Isolation And Characterization of Mitochondria From Human B Lymphoblastoid Cell Lines," Biochemical and Biophysical Research Communications, Jul. 15, 1992, vol. 186, No. 1, pp. 16-23, XP055144685.
Brass et al., "Multiple Skeletal Muscle Mitochondrial DNA Deletions in Patients with Unilateral Peripheral Arterial Disease," 2000, Vascular Medicine 5(4):225-230.
Caicedo A., et al., "Mitoception as a New Tool to Assess the Effects of Mesenchymal Stem/Stromal Cell Mitochondria on Cancer Cell Metabolism and Function," Scientific Reports, Mar. 13, 2015, vol. 5, No. 1, Article 9073, pp. 1-10.
Cardenes N., et al., "De Mesenchymal Stem Cells: a Promising Therapy for the Acute Respiratory Distress Syndrome," Respiration, Feb. 2013, vol. 85, No. 4, pp. 267-278.
Chan D.C., et al., "Mitochondrial Fusion and Fission in Mammals," Annual Review of Cell and Developmental Biology, 2006, vol. 22, pp. 79-99.
Chemicon International Inc.: "Adipogenesis Assay Kit," Cat. No. ECM950, 2004, Revision C, 41448, 12 Pages.
Chen et al. "Inhibition of Triglyceride Synthesis as a Treatment Strategy for Obesity: Lessons From DGAT1-Deficient Mice" 2005, Arteriosclerosis, Thrombosis and Vascular Biology 25(3):482-486.
Chen M., et al., "Generation of Retinal Ganglion-like Cells From Reprogrammed Mouse Fibroblasts," Investigative Ophthalmology & Visual Science, 2010, vol. 51, No. 11, pp. 5970-5978.
Chinnery P.F., et al., "The Challenges of Mitochondrial Replacement," PLoS Genetics, Published on Apr. 24, 2014, vol. 10, No. 4, e1004315, 2 Pages.
Choi Y-S., et al., "Analysis of Proteome Bound To D-loop Region of Mitochondrial DNA By DNA-linked Affinity Chromatography And Reverse-Phase Liquid Chromatography/Tandem Mass Spectrometry," Annals of the New York Academy of Sciences, May 31, 2005, vol. 1042, pp. 88-100, XP055035180.
Clark M.A., et al., "Mitochondrial Transformation of Mammalian Cells," Nature, Macmillan Journals Ltd, London, GB, Feb. 18, 1982, vol. 295, No. 5850, pp. 605-607, ISSN 0028-0836, XP002625375.
Cook G.A., et al., "Structural Changes of Isolated Hepatocytes During Treatment With Digitonin," Biochimica et Biophysica Acta (BBA)-Molecular Cell Research, Dec. 1983, vol. 763, No. 4, pp. 356-367.
Corcelli A., et al., "Mitochondria Isolated in Nearly Isotonic Kci Buffer: Focus on Cardiolipin and Organelle Morphology," Biochimica et Biophysica Acta 1798, 2010, pp. 681-687.
Cowdry N.H., "A Comparison of Mitochondria in Plant and Animal Cells," The Biological Bulletin, 1917, vol. 33, No. 3, pp. 196-228.
Csordas A., "Mitochondrial Transfer Between Eukaryotic Animal Cells And Its Physiologic Role," Rejuvenation Research, Feb. 2006, vol. 9, No. 4, pp. 450-454.
Das Neves R.P., et al., Connecting Variability in Global Transcription Rate to Mitochondrial Variability, PLoS biology, 2010, vol. 8, No. 12, e1000560.
English Translation of Notice of Reasons for Rejection for Japanese Application No. 2021-142214, dated Jun. 21, 2022, 15 Pages.
Extended European Search Report for European Application No. 12830575.2, mailed Feb. 13, 2015, 11 Pages.
Extended European Search Report for European Application No. 16754857.7, mailed Jul. 13, 2018, 06 Pages.
Extended European Search Report for European Application No. 18774886.8, mailed Oct. 26, 2020, 7 Pages.
Extended European Search Report for European Application No. 19776644.7, mailed Jul. 12, 2021, 06 Pages.
Extended European Search Report for European Application No. 19842284.2, mailed May 4, 2022, 8 Pages.
Finsterer J., et al., "Renal Manifestations of Primary Mitochondrial Disorders," Biomedical Reports May 2014 Spandidos Publications GBR, vol. 6, No. 5, May 1, 2017, pp. 487-494.
Frazier A.E., et al., "Mitochondrial Morphology and Distribution in Mammalian Cells," Journal of Biological Chemistry, Dec. 2006, vol. 387, No. 12, 9 Pages.
Frezza C., et al., "Organelle Isolation: Functional Mitochondria From Mouse Liver, Muscle And Cultured Fibroblasts," Nature Protocols, Feb. 22, 2007, vol. 2, No. 2, pp. 287-295, ISSN 1750-2799, XP055038328.
Fu A., et al., "Mitotherapy for Fatty Liver by Intravenous Administration of Exogenous Mitochondria in Male Mice," Frontiers in Pharmacology, Jan. 2017, vol. 8, Article 241, pp. 1-8.
Gasnier F., et al., "Use of Percoll Gradients for Isolation of Human Placenta Mitochondria Suitable for Investigating Outer Membrane Proteins," Analytical Biochemistry, Academic Press Inc., New York, Jul. 1, 1993, vol. 212, No. 1, pp. 173-178, doi: 10.1006/ABIO.1993.1309, ISSN 0003-2697, XP024763625.
Gavazza M., et al., "Sensitivity of Mitochondria Isolated From Liver And Kidney of Rat And Bovine To Lipid Peroxidation: A Comparative Study of Light Emission And Fatty Acid Profiles," Molecular And Cellular Biochemistry, Kluwer Academic Publishers, BO, Dec. 1, 2005, vol. 280, No. 1-2, pp. 77-82, ISSN 1573-4919, XP019288940.
Griffiths E.J., et al., "Mitochondrial Calcium As A Key Regulator of Mitochondrial ATP Production In Mammalian Cells," Biochimica Et Biophysica Acta, Mar. 2009, vol. 1787, No. 11, pp. 1324-1333.
Guantes, et al., "Mitochondria and the Non-Genetic Origins of Cell-to-Cell Variability: More is Different," BioEssays, 2016, vol. 38, No. 1, pp. 64-76.
Hartwig S., et al., "A Critical Comparison Between Two Classical And A Kit-based Method For Mitochondria Isolation," Proteomics, Jan. 31, 2009, vol. 9, No. 11, pp. 3209-3214, XP055144705.
Hassanein T., "Mitochondrial Dysfunction in Liver Disease and Organ Transplantation," Mitochondrion, vol. 4, Sep. 2004, pp. 609-620.
International Preliminary Report on Patentability for International Application No. PCT/IL2012/050359, mailed Mar. 20, 2014, 7 Pages.
International Preliminary Report on Patentability for International Application No. PCT/IL2016/050205, mailed Sep. 8, 2017, 10 Pages.
International Preliminary Report on Patentability for International Application No. PCT/IL2018/050332, mailed Oct. 10, 2019, 8 Pages.
International Preliminary Report on Patentability for International Application No. PCT/IL2019/050350, mailed Oct. 8, 2020, 8 Pages.
International Preliminary Report on Patentability for International Application No. PCT/IL2019/050821, mailed Feb. 4, 2021, 8 Pages.
International Preliminary Report on Patentability for International Application No. PCT/IL2019/050822, mailed Feb. 4, 2021, 8 Pages.
International Preliminary Report on Patentability for International Application No. PCT/IL2019/050823, mailed Feb. 4, 2021, 10 Pages.
International Preliminary Report on Patentability for International Application No. PCT/IL2019/050824, mailed Feb. 4, 2021, 7 Pages.
International Preliminary Report on Patentability for International Application No. PCT/IL2019/050825, mailed Feb. 4, 2021, 10 Pages.
International Preliminary Report on Patentability for International Application No. PCT/IL2019/050826, mailed Feb. 4, 2021, 9 Pages.
International Preliminary Report on Patentability for International Application No. PCT/IL2019/050827, mailed Feb. 4, 2021, 9 Pages.
International Preliminary Report on Patentability for International Application No. PCT/IL2019/050828, mailed Feb. 4, 2021, 8 Pages.
International Preliminary Report on Patentability for International Application No. PCT/IL2021/050349, mailed Oct. 13, 2022, 11 Pages.
International Preliminary Report on Patentability for International Application No. PCT/IL2021/050358, mailed Oct. 13, 2022, 8 Pages.

(56) References Cited

OTHER PUBLICATIONS

International Preliminary Report on Patentability for the application No. PCT/IL2022/050098, mailed Jul. 20, 2023, 9 pages.
International Search Report and Written Opinion for Application No. PCT/IL2022/050098, mailed on May 26, 2022, 10 Pages.
International Search Report and Written Opinion for Application No. PCT/IL2022/051280, mailed on Dec. 1, 2022, 13 pages.
International Search Report and Written Opinion for International Application No. PCT/IL2012/050359, mailed Nov. 25, 2012, 10 Pages.
International Search Report and Written Opinion for International Application No. PCT/IL2016/050205, mailed Jun. 19, 2016, 13 Pages.
International Search Report and Written Opinion for International Application No. PCT/IL2018/050332, mailed Jun. 13, 2018, 11 Pages.
International Search Report and Written Opinion for International Application No. PCT/IL2019/050350, mailed Jul. 7, 2019, 10 Pages.
International Search Report and Written Opinion for International Application No. PCT/IL2019/050821, mailed Nov. 26, 2019, 9 Pages.
International Search Report and Written Opinion for International Application No. PCT/IL2019/050822, mailed Nov. 27, 2019, 11 Pages.
International Search Report and Written Opinion for International Application No. PCT/IL2019/050823, mailed Nov. 18, 2019, 11 Pages.
International Search Report and Written Opinion for International Application No. PCT/IL2019/050824, mailed Dec. 15, 2019, 8 Pages.
International Search Report and Written Opinion for International Application No. PCT/IL2019/050825, mailed Nov. 28, 2019, 11 Pages.
International Search Report and Written Opinion for International Application No. PCT/IL2019/050826, mailed Nov. 24, 2019, 10 Pages.
International Search Report and Written Opinion for International Application No. PCT/IL2019/050827, mailed Nov. 20, 2019, 11 Pages.
International Search Report and Written Opinion for International Application No. PCT/IL2019/050828, mailed Nov. 24, 2019, 11 Pages.
International Search Report and Written Opinion for International Application No. PCT/IL2021/050349, mailed Aug. 17, 2021, 14 Pages.
International Search Report and Written Opinion for International Application No. PCT/IL2021/050358, mailed Jul. 20, 2021, 10 Pages.
Islam M.N., et al., "Mitochondrial Transfer From Bone-marrow-derived Stromal Cells to Pulmonary Alveoli Protects Against Acute Lung Injury," Nature Medicine, Apr. 15, 2012, vol. 18, No. 5, pp. 759-765, 15 Pages, XP055475523, Retrieved from URL: http://www.nature.com/nm/journal/v18/n5/abs/nm.2736.html.
Jelenik T., et al., "Mitochondrial Plasticity in Obesity and Diabetes Mellitus," Antioxidants & Redox Signaling, 2013, vol. 19, No. 3, pp. 258-268.
Jenuth J.P., et al., "Random Genetic Drift in the Female Germline Explains the Rapid Segregation of Mammalian Mitochondrial DNA," Nature Genetics, 1996, vol. 14, No. 2, pp. 146-151.
Jenuth J.P., et al., "Tissue-Specific Selection for Different mtDNA Genotypes in Heteroplasmic Mice," Nature Genetics, 1997, vol. 16, No. 1, pp. 93-95.
Jeon S.Y., et al., "Comparison of Hair Shaft Damage After UVA and UVB Irradiation," The Journal of Cosmetic Science, Mar.-Apr. 2008, vol. 59, No. 2, pp. 151-156 (Abstract), 1 Page.
Katrangi E., et al., "Xenogenic Transfer of Isolated Murine Mitochondria Into Human p0 Cells Can Improve Respiratory Function," Rejuvenation Research, Dec. 2007, vol. 10, No. 4, pp. 561-570.
Khasawneh et al., "A Novel Mitochondrial DNA Deletion in Patient with Pearson Syndrome" Med Arch., Apr. 2018, vol. 72, No. 2, pp. 148-150.
King M.P., et al., "Injection of Mitochondria Into Human Cells Leads To a Rapid Replacement of The Endogenous Mitochondrial DNA," Cell, vol. 52, No. 6, Mar. 25, 1988, pp. 811-819.
Kitani T., et al., "Direct Human Mitochondrial Transfer: A Novel Concept Based on the Endosymbiotic Theory," Transplantation Proceedings, 2014, vol. 46, No. 4, pp. 1233-1236.
Kitani T., et al., "Internalization of Isolated Functional Mitochondria: Involvement of Macropinocytosis," Journal of Cellular and Molecular Medicine, Apr. 2014, vol. 18, No. 8, pp. 1694-1703.
Klotzsch S.G., et al., "Triglyceride Measurements: A Review of Methods and Interferences," Clinical Chemistry, 1990, vol. 36, No. 9, pp. 1605-1613.
Kuranda K., et al., "Exposure to Wild-Type AAV Drives Distinct Capsid Immunity Profiles in Humans," Journal of Clinical Investigation, Dec. 3, 2018, vol. 128, No. 12, pp. 5267-5279, XP055927987.
Kuznetsov A.V., et al., "Cryopreservation of Mitochondria And Mitochondrial Function In Cardiac And Skeletal Muscle Fibers," Analytical Biochemistry, Sep. 2003, vol. 319. No. 2, pp. 296-303.
Lachgar S., et al., "Vascular Endothelial Growth Factor is an Autocrine Growth Factor for Hair Dermal Papilla Cells," The Journal of Investigative Dermatology, 1996, vol. 106, No. 1, pp. 17-23.
Larsen S., et al., "Biomarkers of Mitochondrial Content in Skeletal Muscle of Healthy Young Human Subjects," The Journal of physiology, 2012, vol. 590, No. 14, pp. 3349-3360.
Lin C.S., et al., "Mouse mtDNA Mutant Model of Leber hereditary Optic Neuropathy," Proceedings of the National Academy of Sciences, 2012, vol. 109, No. 49, pp. 20065-20070.
Lin H.D., et al., "Human Wharton's Jelly Stem Cell Conditioned Medium Enhances Freeze-Thaw Survival and Expansion of Cryopreserved CD 34+ cells," Stem Cell Reviews and Reports, Apr. 2013, vol. 9, No. 2, pp. 172-183, XP055927986.
Lu Z., et al., "Profiling the Response of Human Hair Follicles to Ultraviolet Radiation," The Journal of Investigative Dermatology, 2009, vol. 129, No. 7, pp. 1790-1804.
"Maintenance of Mitochondrial Function by Nuclear NAD+ Levels and its Disruption by Aging," Vitamin, 2016, vol. 90, No. 10, pp. 502-507.
Makris et al., "Mitochondriopathy of Peripheral Arterial Disease" 2007, Vascular 15(6):336-343.
Martinez F., et al., "Structural And Functional Changes In Mitochondria Associated With Trophoblast Differentiation: Methods To Isolate Enriched Preparations of Syncytiotrophoblast Mitochondria," Endocrinology, May 31, 1999, vol. 138, No. 5, pp. 2172-2183, XP055144697.
Masuzawa et al., "Transplantation of Autologously Derived Mitochondria Protects the Heart from Ischemia-reperfusion Injury" Jan. 25, 2013, American Journal of Physiology—Heart and Circulatory Physiology 304(7):H966-H982.
Mccully J.D., et al., "Injection of Isolated Mitochondria During Early Reperfusion For Cardioprotection," The American Journal of Physiology—Heart and Circulatory Physiology, Oct. 31, 2008, vol. 296, No. 1, 13 Pages, XP055144701.
Messenger A.G., et al., "Minoxidil: Mechanisms of Action on Hair Growth," British Journal of Dermatology, 2004, vol. 150, No. 2, pp. 186-194.
Mialet-Perez et al. "Cardiac monoamine oxidases: at the heart of mitochondrial dysfunction," Cell Death Dis, Jan. 23, 2020, vol. 11 (54), pp. 1-3, [retrieved on Nov. 4, 2022], retrieved from the Internet: URL: https://www.nature.com/articles/s41419-020-2251-4.pdf.
Modica-Napolitano J.S., et al., "Mitochondria As Targets For Detection And Treatment of Cancer," Expert Reviews in Molecular Medicine, Apr. 2002, vol. 4, No. 9, pp. 1-19.
Morley S.A., et al., "Plant Mitochondrial DNA," Frontiers in Bioscience, Landmark, Jan. 1, 2017, vol. 22, pp. 1023-1032.
Mracek et al,. "The Function and the Role of the Mitochondrial Glycerol-3-Phosphate Dehydrogenase in Mammalian Tissues," Biochimica et Biophysica Acta (BBA)—Bioenergetics, Dec. 7,

(56) References Cited

OTHER PUBLICATIONS 2012, vol. 1827(3), pp. 401-410, [retrieved on Nov. 4, 2022], retrieved from the Internet: URL: https://doi.org/10.1016/j.bbabio.2012.11.014.

Muftuoglu et al. "Mitochondrial Complex I and IV Dysfunction of Leukocytes in Parkinson's Disease" 2003, Turkish Journal of Biochemistry 28(4):246-251.

Muir R., et al., "Mitochondrial Content is Central to Nuclear Gene Expression: Profound Implications for Human Health," BioEssays, 2015, vol. 38, No. 2, pp. 150-156.

Murphy et al. "Allogeneic Endometrial Regenerative Cells: an Off the Shelf Solution for Critical Limb Ischemia?" Aug. 19, 2008, Journal of Translational Medicine 6(45): 1-8.

Murthy M.S.R., et al., "Some Differences In The Properties Of Carnitine Palmitoyltransferase Activities Of The Mitochondrial Outer And Inner Membranes," Biochemical Journal, 1987, vol. 248, No. 3, pp. 727-733.

Nakamura K., et al., "Characterization Of Bioactive Agents In Five Types Of Marketed Sprouts And Comparison Of Their Antihypertensive, Antihyperlipidemic, And Antidiabetic Effects In Fructose—Loaded SHRs," Journal of Food Science and Technology, 2016, vol. 53, No. 1, pp. 581-590.

Neste D.V., et al., "Finasteride Increases Anagen Hair in Men with Androgenetic Alopecia," British Journal of Dermatology, 2000, vol. 143, No. 4, pp. 804-810.

Noterman M.F., et al., "Dual-Process Brain Mitochondria Isolation Preserves Function And Clarifies Protein Composition," PNAS, Feb. 2, 2021, vol. 118, No. 11, pp. 1-10.

Office Action for European Application No. 16754857.7, mailed May 4, 2022, 10 Pages.

Office Action for European Patent Application No. 12830575.2, mailed Mar. 16, 2017, 4 Pages.

Office Action for European Patent Application No. 12830575.2, mailed Feb. 24, 2016, 10 Pages.

Office Action for European Patent Application No. 12830575.2, mailed Oct. 25, 2016, 8 Pages.

Office Action for European Patent Application No. 12830575.2, mailed Sep. 28, 2015, 7 Pages.

Office Action for European Patent Application No. 16754857.7, mailed Jun. 6, 2019, 4 Pages.

Office Action for European Patent Application No. 19841655.4, mailed Jun. 28, 2023, 17 Pages.

Office action for Israel Patent Application No. 299482, mailed Jun. 22, 2023, 6 pages.

Office Action for Japanese Patent Application No. 2020551356, mailed Feb. 7, 2023, 11 Pages.

Office Action for Japanese Patent Application No. 2021502765, mailed Jun. 27, 2023, 11 Pages.

Office Action for Japanese Patent Application No. 2021502783, mailed Jun. 27, 2023, 10 Pages.

Office Action for Japanese Patent Application No. 2021502844, mailed Jul. 4, 2023, 16 Pages.

Office Action for Japanese Patent Application No. 2021502870, mailed Jun. 27, 2023, 10 Pages.

Office Action for Japanese Patent Application No. 2021502879, mailed Jun. 27, 2023, 19 Pages.

Office Action for Japanese Patent Application No. 2021503582, mailed Jun. 27, 2023, 16 Pages.

Parone P.A., et al., "Preventing Mitochondrial Fission Impairs Mitochondrial Function And Leads To Loss Of Mitochondrial Dna," PLoS One, Feb. 2008, vol. 3, No. 9, 9 Pages.

Pasquier J., et al., "Preferential Transfer of Mitochondria From Endothelial to Cancer Cells Through Tunneling Nanotubes Modulates Chemoresistance," Journal of Translational Medicine, Apr. 10, 2013, vol. 11, No. 94, 14 Pages, XP021151199, Retrieved from URL: http://download.springer.com/static/pdf/438/art%253A10.1186%252F1479-5876-11-94.pdf?originUrl=http%3A%2F%2Ftranslational-medicine.biomedcentral.com%2Farticle%2F10.1186%2F1479-5876-11-94&token2=exp=1465970179~ac1=%2Fstatic%2Fpdf%2F438%2Fart%25253A10.1186%25252F1479-5876-11-94.pdf*~hmac=9ddc595d5.

Piel et al. "Exogenous Cytochrome C Restores Myocardial Cytochrome Oxidase Activity into the Late Phase of Sepsis" 2008, Shock 29(5):612-616.

Piel et al. "Mitochondrial Resuscitation with Exogenous Cytochrome C in the Septic Heart" 2007, Critical Care Medicine 35(9):2120-2127.

Pinkert C.A., et al., "Mitochondria Transfer Into Mouse Ova By Microinjection," Transgenic Research, Nov. 1997, vol. 6, No. 6, pp. 379-383.

Pipino C., et al., "Placenta As A Reservoir of Stem Cells: An Underutilized Resource?," British Medical Bulletin, Nov. 25, 2012, vol. 105, No. 1, pp. 1-25.

Platzbecker et al., "Treatment of MDS," Blood, The Journal of the American Society of Hematology, 2019, vol. 133, No. 10, pp. 1096-1107.

Plotnikov E.Y., et al., "Cytoplasm And Organelle Transfer Between Mesenchymal Multipotent Stromal Cells And Renal Tubular Cells In Co-culture," Experimental Cell Research, Sep. 10, 2010, vol. 316, No. 15, pp. 2447-2455.

Romero-Moya D., et al., "Cord Blood-Derived CD34+ Hematopoietic Cells With Low Mitochondrial Mass Are Enriched in Hematopoietic Repopulating Stem Cell Function," Haematologica, 2013, vol. 98, No. 7, pp. 1022-1029.

Roushandeh A.M., et al., "Mitochondrial Transplantation as a Potential and Novel Master Key for Treatment of Various Incurable Diseases," Cytotechnology, 2019, vol. 71, No. 2, pp. 647-663.

Rousou A.J., et al., "Opening of Mitochondrial KATP Channels Enhances Cardioprotection Through The Modulation of Mitochondrial Matrix Volume, Calcium Accumulation, And Respiration," American Journal of Physiology-Heart and Circulatory Physiology, Jul. 8, 2004, vol. 287, No. 5, pp. H1967-H1976, XP055144706.

Saely C.H., et al., "Brown versus White Adipose Tissue: A Mini-Review," Gerontology, 2012, 58(1), pp. 15-23.

Satoh et al. "Mitochondrial Damage-induced Impairment of Angiogenesis in the Aging Rat Kidney" Feb. 2011, Laboratory Investigation 91(2):190-202.

Schechner et al. "Engraftment of a Vascularized Human Skin Equivalent" Dec. 2003, FASEB Journal 17(15):2250-2256.

Sebetic K., et al., "UV Damage of the Hair," Collegium Antropologicum, 2008, vol. 32 Supplement.2, pp. 163-165.

Shi J., et al., "Mitochondria Transfer Into Fibroblasts: Liposome-Mediated Transfer of Labeled Mitochondria Into Cultured Cells," Ethnicity and Disease, Mar. 2008, vol. 18, No. 2, pp. S1-43-S1-44.

Shimoji H., et al., "Inhibitory Effects of Flavonoids on Alternative Respiration of Plant Mitochondria," Biologia Plantarum, 2005, vol. 49, No. 1, pp. 117-119.

Shin et al., "Mitochondrial DNA Mutations in Patients with Myelodysplastic Syndromes", Blood, The Journal of the American Society of Hematology, 2003, vol. 101, No. 8, pp. 3118-3125.

Sidney L.E., et al., "Concise Review: Evidence for CD34 as a Common Marker for Diverse Progenitors," Stem Cells, 2014, vol. 32, No. 6, pp. 1380-1389.

Sivitz W.I., et al., "Mitochondrial Dysfunction In Obesity And Diabetes," US Endocrinology, Dec. 31, 2010, vol. 6, No. 1, pp. 20-27, DOI: 1 0.17925/USE.201 0.06.1.20, XP055729849.

Smith et al. "Locally Enhanced Angiogenesis Promotes Transplanted Cell Survival" 2004, Tissue Engineering 10(1-2):63-71 (11 pages).

Smith L.J., et al., "Stem Cell-Derived Clade F AAVs Mediate High-Efficiency Homologous Recombination-Based Genome Editing," Proceedings of the National Academy of Sciences of the United States of America, Jul. 31, 2018, vol. 115, No. 31, DOI: 10.1073/pnas. 1802343115, pp. E7379-E7388, XP055609078.

Snyder C., et al., "Mitochondria and Chloroplasts Shared in Animal and Plant Tissues: Significance of Communication," Medical Science Monitor, 2015, vol. 21, pp. 1507-1511.

Spees J.L., et al., "Mitochondrial Transfer Between Cells Can Rescue Aerobic Respiration," Proceedings Of The National Academy Of Sciences, US, Jan. 31, 2006, vol. 103, No. 5, pp. 1283-1288, doi:10.1073/pnas.0510511103, ISSN 0027-8424, XP055349990.

(56) References Cited

OTHER PUBLICATIONS

Stork C., et al., "Mitochondrial Dysfunction in Bipolar Disorder: Evidence From Magnetic Resonance Spectroscopy Research," Molecular Psychiatry, 2005, vol. 10, No. 10, pp. 900-919.
Szewczyk A., et al., "Mitochondria as a Pharmacological Target," Pharmacological Reviews, Mar. 2002, vol. 54, No. 1, pp. 101-127.
Tachibana M., et al., "Mitochondrial Gene Replacement in Primate Offspring and Embryonic Stem Cells," Nature, Sep. 17, 2009, vol. 461, No. 7262:367-372, 15 Pages, doi:10.1038/nature08368, XP055072881, Retrieved from URL: http://www.nature.com/nature/journal/v461/n7262/abs/nature08368.html.
Takeda K., et al., "Microinjection of Cytoplasm or Mitochondria Derived From Somatic Cells Affects Parthenogenetic Development of Murine Oocytes," Biology of Reproduction, Feb. 16, 2005, vol. 72, No. 6, pp. 1397-1404.
The Champ Foundation, "William's blog., Let's get More Research Started," Fighting against Pearson Syndrome, May 1, 2017, 4 pages.
Tian L., et al., "Impaired Mitochondrial Function Results from Oxidative Stress in the Full-Term Placenta of Sows with Excessive Back-Fat," Animals, Feb. 2020, vol. 10, No. 360, pp. 1-19.
Torralba D., et al., "Mitochondria Know No Boundaries: Mechanisms and Functions of Intercellular Mitochondrial Transfer," Front Cell Dev Biol., Sep. 2016, vol. 4, 11 pages.
Tuckey R.C., et al., "The Concentration Of Adrenodoxin Reductase Limits Cytochrome P450scc Activity In The Human Placenta," European Journal of Biochemistry, Jul. 31, 1999, vol. 263, No. 2, pp. 319-325, XP055144683.
Tuckey R.C., "Progesterone Synthesis by the Human Placenta," Placenta, May 2005, vol. 26, No. 4, pp. 273-281.
Van Blerkom J., et al., "Mitochondrial Transfer Between Oocytes: Potential Applications Of Mitochondrial Donation And The Issue Of Heteroplasmy," Human Reproduction, Nov. 1998, vol. 13, No. 10, pp. 2857-2868.
Wagle M.A., et al., "The Utility Of An Isolated Mitochondrial Fraction In The Preparation Of Liposomes For The Specific Delivery Of Bioactives To Mitochondria In Live Mammalian Cells," Pharmaceutical Research, Jul. 15, 2011, vol. 28, No. 11, pp. 2790-2796.
Wang W., et al., "Novel Targets for Mitochondrial Medicine," Science Translational Medicine, vol. 8, No. 326, Feb. 17, 2016, 17 pages, Retrieved from the Internet: https://www.ncbi.nlm.nih.gov/pmc/articles/PMC4819426/pdf/nihms769346.pdf.
Wei Y., et al., "Nonalcoholic Fatty Liver Disease and Mitochondrial Dysfunction," World J Gastroenterol, Jan. 14, 2008, vol. 14, No. 2, pp. 193-199.
Weiss J.N., et al., "Stem Cell Ophthalmology Treatment Study: Bone Marrow Derived Stem Cells in the Treatment of Retinitis Pigmentosa," Stem Cell investigation, Jun. 6, 2018, vol. 5, No. 18, pp. 1-9, doi: 10.21037/sci.2018.04.02, XP055778156.
Wieckowski M.R., et al., "Isolation Of Mitochondria-Associated Membranes And Mitochondria From Animal Tissues And Cells," Nature Protocol, Oct. 8, 2009, vol. 4, No. 11, pp. 1582-1590.
Xu Y., et al., "Efficient Commitment To Functional CD34+ Progenitor Cells From Human Bone Marrow Mesenchymal Stem-cell-derived Induced Pluripotent Stem Cells," PLoS One, vol. 7, No. 4, 2012, e34321,10 Pages.
Yamagata K., et al., "Pathological Roles of Mitochondrial Dysfunction in Podocyte Injury," The Japanese Journal of Nephrology, 2007, vol. 49, No. 2, pp. 82-87.
Yamaguchi R., et al., "Mitochondria Frozen With Trehalose Retain A Number Of Biological Functions And Preserve Outer Membrane Integrity," Cell Death Differentiation, Copyright Year: 2007, Published Online: Sep. 15, 2006, vol. 14, No. 3, pp. 616-624, XP055144699.
Yasuda K., et al., "Tunneling Nanotubes Mediate Rescue Of Prematurely Senescent Endothelial Cells By Endothelial Progenitors: Exchange Of Lysosomal Pool," Aging, Jun. 2011, vol. 3, No. 6, pp. 597-608.
You Y., et al., "Mulberry and Mulberry Wine Extract Increase the Number of Mitochondria During Brown Adipogenesis," Food & Function, Feb. 2015, vol. 6, No. 2, pp. 401-408.
Yu J., et al., "Induced Pluripotent Stem Cell Lines Derived From Human Somatic Cells," Science, Dec. 21, 2007, vol. 318, No. 5858, pp. 1917-1920.
Zhang Y., et al., "Deletion of a 4977-bp Fragment in the Mitochondrial Genome is Associated With Mitochondrial Disease Severity," PloS One, May 29, 2015, vol. 10, No. 5: e0128624, 10 Pages, XP055549866, Retrieved from URL: http://journals.plos.org/plosone/article?id=10.1371/journal, pone.0128624.
Zheng Y., et al., "Mitochondrial DNA 4977 bp Deletion is a Common Phenomenon in Hair and Increases with Age," Bosn Journal of Basic Medical Sciences, 2012, vol. 12, No. 3, pp. 187-192.
EP Office Action in European Application No. 19840282.8, dated Jan. 9, 2024, 13 pages.
Gollihue et al., "Prospects for therapeutic mitochondrial transplantation", Mitochondrion, 2017, 35: 70-79.
Lodi et al., "Deficit of in vivo mitochondrial ATP production in patients with Friedreich ataxia", Proc. Natl. Acad. Sci, Sep. 1999, 96: 11492-11495.
Rosa et al., "Vitamin C and E supplementation prevents mitochondrial damage of ileum myocytes caused by intense and exhaustive exercise training", J Appl Physiol, Aug. 2009, 107: 1532-1538.
Sookoian et al., "Mitochondrial genome architecture in non-alcoholic fatty liver disease", Journal of Pathology, Oct. 2016, 240: 437-449.
Tomizawa et al., "Elevated levels of alanine transaminase and triglycerides within normal limits are associated with fatty liver", Experimental and Therapeutic Medicine, May 2014, 8: 759-762.
Au et al., "Mitochondrial DNA deletion in a girl with Fanconi's syndrome", Pediatr Nephrol, 2007, 22:136-140.
Galipeau et al., "Mesenchymal Stromal Cells: Clinical Challenges and Therapeutic Opportunities", Cell Stem Cell 22, Jun. 1, 2018, p. 824-839.
Govers et al., "Mitochondrial DNA mutations in renal disease: an overview". Pediatric Nephrology, 2021, 36:9-17.
Makhlough et al., "Bone marrow—mesenchymal stromal cell infusion in patients with chronic kidney disease: A safety study with 18 months of follow-up", Cytotherapy, 2018; 20:660-669.
Marcheque et al., "Concise Reviews: Stem Cells and Kidney Regeneration: An Update", Stem Cells Translational Medicine, 2019, 8:82-92.
Renaghan et al., "Acute Kidney Injury and CKD Associated with Hematopoietic Stem Cell Transplantation", CJASN, 2020, 15:289-297.
Rota et al., "Stem Cell Therapies in Kidney Diseases: Progress and Challenges", Int. J. Mol. Sci., 2019, 20, 2790, p. 1-26.
Swaminathan et al., "Allogeneic Mesenchymal Stem Cells for Treatment of AKI after Cardiac Surgery", J Am Soc Nephrol, 2018, 29: 260-267.
Yang et al., "Safety and efficacy of intrarenal arterial autologous CD34+ cell transfusion in patients with chronic kidney disease: A randomized, open-label, controlled phase II clinical trial", Stem Cells Transl Med., 2020, 9:827-838.
Gowda et al., "Markers of renal function tests", North American Journal of Medical Science, Apr. 2010, 2(4): 170-173.
Hosten, "Chapter 193: BUN and Creatine", Clinical methods: The History, Physical, and Laboratory Examination, $3^{rd}$ ED., 1990, pp. 874-978.
JP Office Action in Japanese Application No. 2021-502763, dated Mar. 20, 2023, 13 pages (with English translation).
JP Office Action in Japanese Application No. 2021-502836, dated Mar. 20, 2023, 12 pages (with English translation).
Shah et al., "Serum Bicarbonate Levels and the Progression of Kidney Disease: A Cohort Study", Am J Kidney Dis, Aug. 2009, 54(2): 270-277.
Tang et al., "Normalisation of urinary biomarkers to creatine for clinical practice and research—when and why", Singapore Med J, 2015, 56(1): 7-10.
Vormann, "Magnesium and Kidney Health—More on the 'Forgotten Electrolyte'", Am J Nephrol, 2016, 44: 379-380.
Anonymous: "History of Changes for Study: NCT03384420", ClinicalTrials.gov archive, Dec. 2017, 4 pages.

(56) References Cited

OTHER PUBLICATIONS

Anonymous: "William's Blog | The Champ Foundation", The Champ Foundation, Feb. 2018, 5 pages.
EP Extended European Search Report in European Application No. EP19841655.4, dated Mar. 11, 2022, 18 pages.
EP Extended European Search Report in European Application No. EP19840685.2, dated Apr. 22, 2022, 9 pages.
EP Extended European Search Report in European Application No. EP19841817.0, dated May 6, 2022, 7 pages.
EP Extended European Search Report in European Application No. EP19840137.4, dated Apr. 22, 2022, 8 pages.
EP Extended European Search Report in European Application No. EP198407744.4, dated May 6, 2022, 9 pages.
EP Extended European Search Report in European Application No. EP19841283.5, dated May 6, 2022, 7 pages.
EP Extended European Search Report in European Application No. EP19840282.8, dated Apr. 22, 2022, 7 pages.
Gollihue et al., "Mitochondrial transplantation strategies as potential therapeutics for central nervous system trauma", Neural regeneration research, Feb. 2018, 13.2:194.
Jacoby et al., "First-in-Human Mitochondrial Augmentation of Hematopoietic Stem Cells in Pearson Syndrome", Blood, American Society of Hematology, Nov. 2018, 132(Supp. 1):1024.
Jacoby et al., "Mitochondrial augmentation of CD34+ cells from healthy donors and patients with mitochondrial DNA disorders confers functional benefit", NPJ Regenerative Medicine, Dec. 2021, 6(1):1-12.
Che et al. Mitochondrial dysfunction in the pathophysiology of renal diseases, Am J Physiol Renal Physiol 306: F367-F378 (Year:2014).
Keefe et al. Fanconi Syndrome. StatPearls [Internet]. Treasure Island (FL): StatPearls Publishing; Jan. 2021. NCBI Bookshelf. A service of the National Library of Medicine, National Institutes of Health. p. 1-4 (Year: 2021).
Hashimi et al. Nephritic Syndrome. StatPearls [Internet]. Treasure Island (FL): StatPearls Publishing; Jan. 2021. NCBI Bookshelf. A service of the National Library of Medicine, National Institutes of Health. p. 1-8 (Year: 2021).
Hall et al. The Not So 'Mighty Chondrion': Emergence of Renal Diseases due to Mitochondrial Dysfunction. Nephron Physiol 2007; 105:p. 1-p. 10 (Year: 2007).
De Maranon et al., "Targeting mitochondria: a great boon to type 2 diabetes", Redox Experimental Medicine, Aug. 2022, 2022(1): R127-138.
Garone et al., "Clinical and genetic spectrum of mitochondrial neurgastrointestinal encephalomyopathy", Brain, 2011, 134: 3326-3332.
JP Office Action in Japanese Application No. 2021-503582, dated Feb. 19, 2024, 13 pages (with English translation).
Nishigaki et al., "Mitochondrial Dysfunctions and Age-associated Diseases", Japanese Journal of Geriatrics, 2006, 43(3): 274-282, 15 pages (with English abstract).
Seo et al., "Age-related changes in skeletal muscle mitochondria: the role of exercise", Integrative Medicine Research, Jul. 2016, 5(3): 182-186.
Wakino et al., "The Cutting-Edge or Medicine: Aging and Chronic Kidney Disease", Japanese Journal of Geriatrics, 2017, 106(5): 1019-1028, 12 pages (with English abstract).
Ahmed et al. "Human Epidermal Growth Factor Receptor 2 (HER2)—Specific Chimeric Antigen Receptor Modified T Cells for the Immunotherapy of HER2 positive Sarcoma", Journal of Clinical Oncology, May 2015 vol. 33, No. 15 pp. 1688-1696. doi: 10.1200/JCO.2014.58.0225. Epub Mar. 23, 2015. PMID: 25800760; PMCID: PMC4429176.
Yu-Wai-Man, P. et al. 2009 "Inherited mitochondrial optic neuropathies". Journal of medical genetics, 46(3), pp. 145-158 (2008). doi: 10.1136/jmg.2007.054270. Epub Nov. 10, 2008. Erratum in: J Med Genet. Apr. 2011;48(4):284. PMID: 19001017; PMCID: PMC2643051.
Mi Jin Kim et al. "Delivery of Exogenous mitochondria via centrifugation enhances cellular metabolic function" Seientific reports vol. 8 No. 1, Feb. 20, 2018. https://doi.org/10.1038/s41598-018-21539-y.
Silva, Gisele S. et al., "Causes of ischemic stroke" in, Acute ischemic stroke: imaging and intervention, R.G. Gonzalez et al. (Eds.) Springer-Verlag Berlin Heidelberg 2011, pp. 25-42. DOI:10.1007/978-3-642-12751-9_2.
Bartelink Imke H, et al."Association between busulfan exposure and outcome in children receiving intravenous busulfan before hematologic stem cell transplantation" Biology of blood and marrow transplantation 15.2 (2009) 231-241. https://doi.org/10.1016/j.bbmt.2008.11.022.
Prasun P, Ginevic I, Oishi K. "Mitochondrial dysfunction in non-alcoholic fatty liver disease and alcohol related liver disease". Transl Gastroenterol Hepatol. Jan. 5, 2021;6:4. doi: 10.21037/tgh-20-125. PMID: 33437892; PMCID: PMC7792990.
Canadian Center Society, "Side effects of a stem cell transplant". Available online: [https://cancer.ca/en/treatments/treatment-types/stem-cell-transplant/side-effects-of-stem-cell-transplant].
Rao RS, Salvato F, Thal B, Eubel H, Thelen JJ, Møller IM. "The proteome of higher plant mitochondria". Mitochondrion. Mar. 2017;33:22-37. doi: 10.1016/j.mito.2016.07.002. Epub Jul. 9, 2016. PMID: 27405097.
Naing et al., "Maternally inherited diabetes and deafness (MIDD): Diagnosis and management", Journal of Diabetes and its Complications, vol. 28, Issue 4, 2014, pp. 542-546, doi: 10.1016/j.jdiacomp.2014.03.006. Epub Mar. 12, 2014. PMID: 24746802.
Rovira-Llopis et al., "Mitochondrial dynamics in type 2 diabetes: Pathophysiological implications", Redox Biology, vol. 11, 2017, pp. 637-645, doi: 10.1016/j.redox.2017.01.013. Epub Jan. 16, 2017. PMID: 28131082; PMCID: PMC5284490.
Imamura, Yoji et al. "Angiogenic therapy using autologous bone marrow stem cells Results of autologous bone marrow cells implantation (BMI) for hindlimb and ischemic myocardium", Journal of Saitama Medical University, 2003, vol. 30, No. 4, p. 195.
Masakaba Tagawa et al. "Cell therapy using bone marrow mononuclear cells"J Jpn Coll Angiol, 2006, vol. 46, pp. 281-288.
Caldas de Andrade et al. "Bone marrow mononuclear cell transplantation improves mitochondrial bioenergetics in the liver of cholestatic rats" Experimental Cell Research, vol. 336, Issue 1, 2015, pp. 15-22, doi: 10.1016/j.yexcr.2015.05.002. Epub May 12, 2015. PMID: 25978973.
Weihong Yan et al. "Umbilical Cord MSCs Reverse D-Galactose-Induced Hepatic Mitochondrial Dysfunction via Activation of Nrf2/HO-1 Pathway", Biological and Pharmaceutical Bulletin, 2017, 40 p. 1174-1182, doi: 10.1248/bpb.b16-00777. Epub May 13, 2017. PMID: 28502921.
Greiff, D., and M. Myers. "Effect of dimethyl sulphoxide on the cryo-tolerance of mitochondria." Nature 190.4782 (1961): 1202-1204. https://doi.org/10.1038/1901202b0.
Nukala, Vidya N., et al. "Cryopreservation of brain mitochondria: a novel methodology for functional studies." Journal of neuroscience methods 152.1-2 (2006): 48-54. doi: 10.1016/j.jneumeth.2005.08.017. Epub Oct. 24, 2005. PMID: 16246427.

\* cited by examiner

MITOCHONDRIAL AUGMENTATION THERAPY OF RENAL DISEASES

CROSS-REFERENCE TO RELATED APPLICATIONS

This application is a 35 USC § 371 National Stage application of International Application No. PCT/IL2019/050821 filed Jul. 22, 2019; which claims the benefit under 35 USC § 119(e) to U.S. Application Ser. No. 62/753,934 filed Nov. 1, 2018 and U.S. Application Ser. No. 62/701,783 filed Jul. 22, 2018. The disclosure of each of the prior applications is considered part of and is incorporated by reference in the disclosure of this application.

FIELD OF THE INVENTION

The present invention provides stem cells enriched with functional mitochondria and methods of using mitochondrial augmentation therapy for treating renal-associated diseases, disorders and conditions in humans.

BACKGROUND OF THE INVENTION

Kidney disease, or renal disease, also known as nephropathy, is damage to or disease of a kidney. Nephritis is an inflammatory kidney disease. Nephrosis is non-inflammatory kidney disease. Nephritis and nephrosis can give rise to nephritic syndrome and nephrotic syndrome, respectively. Kidney disease usually causes a loss of kidney function to some degree and can result in kidney failure, the complete loss of kidney function. Kidney failure is known as the end-stage of kidney disease, where dialysis or a kidney transplant is the only treatment option.

Causes of kidney disease include deposition of the Immunoglobulin A antibodies in the glomerulus, administration of analgesics, xanthine oxidase deficiency, toxicity of chemotherapy agents, and/or long-term exposure to lead or its salts. Chronic conditions that can produce nephropathy include systemic lupus erythematosus, diabetes mellitus and high blood pressure (hypertension), which lead to diabetic nephropathy and hypertensive nephropathy, respectively. Sepsis is also known to induce acute kidney diseases.

Mitochondrial diseases are a genetically heterogeneous group of disorders caused by mutations in mitochondrial DNA (mtDNA) or nuclear DNA (nDNA) displaying a wide range of severity and phenotypes (Wallace, D. C. and Chalkia, D., Cold Spring Harb. Perspect. Biol. 2013; 5:a021220). The prevalence of mtDNA-related disease is about 1 in 8500 in the population (Elliott, H. R. et al., American Journal of Human Genetics, 83, 254-260, 2008), yet to date, apart from supportive therapy there is no effective treatment for the majority of mitochondrial diseases. A variety of treatments have been evaluated in clinical trials but none has delivered breakthrough results (Kanabus, M. et al., British journal of pharmacology, 171, 1798-1817, 2014).

One of the causes of high blood pressure is kidney disease. It was previously suggested that the J mitochondrial haplotype, which is also linked to longevity, is correlated with lower blood pressure (Rea et al. AGE 34:4 (2013) 1445-1456). It was demonstrated that the V and J haplotypes are correlated with a lower chance of developing chronic renal allograft dysfunction following kidney transplant (Jimenez-Sousa et al. Int J Med Sci 11:11 (2014) p1129-1132)

WO 2013/035101 to the present inventors relates to mitochondrial compositions and therapeutic methods of using same, and discloses compositions of partially purified functional mitochondria and methods of using the compositions to treat conditions which benefit from increased mitochondrial function by administering the compositions to a subject in need thereof.

WO 2016/008937 relates to methods for the intercellular transfer of mitochondria isolated from a population of donor cells into a population of recipient cells. The methods show improved efficacy of transfer of an amount mitochondria.

US 2012/0107285 is directed to mitochondrial enhancement of cells. Certain embodiments include, but are not limited to, methods of modifying stem cells, or methods of administering modified stem cells to at least one biological tissue.

WO 2016/135723 to the present inventors relates to human bone-marrow cells enriched by at least 50% with functional mitochondria, methods for their production, and therapeutic methods utilizing such cells.

There is a long-felt need in the field of therapy of kidney diseases, e.g. those unrelated to primary mitochondrial diseases, for effective and long term therapies.

SUMMARY OF THE INVENTION

According to the principles of the present invention, human stem cells enriched with healthy and functional mitochondria are introduced into a subject afflicted with kidney dysfunction or failure. This process, generally referred to as "mitochondria augmentation therapy", increases the number of healthy and functional mitochondria within these stem cells. Stem cells enriched with healthy and functional mitochondria are administered to patients suffering from kidney-related diseases and disorders to provide alleviation of symptoms associated with the kidney dysfunction and improve the parameters of kidney function. In certain embodiments, the disease or disorder is associated with acquired mitochondrial dysfunction. In other embodiments, the disease or disorder is not associated with acquired mitochondrial dysfunction.

The present invention is based in part on the findings that a single round of treatment of juveniles with Pearson Syndrome (PS), a congenital disease caused by a mutation in mitochondrial DNA, with stem cells enriched with healthy functional mitochondria was sufficient to ameliorate significantly a variety of parameters relating to kidney function.

Without being restricted to any theory or mechanism, it is hypothesized that the systemic administration of mitochondrially augmented human stem cells resulted in the enhancement of mitochondrial activity in the patient's renal system, and that this enhancement, ameliorated the severity of symptoms of Pearson Syndrome, including renal symptoms deriving directly or indirectly from the mitochondrial DNA mutation.

The present invention provides, in one aspect, a method for treating a renal disease, disorder or a symptom thereof in a human patient in need of such treatment, the method comprising the step of administering parenterally a pharmaceutical composition to the patient, the pharmaceutical composition comprising at least about $5 \times 10^5$ to $5 \times 10^9$ human stem cells, wherein the human stem cells are enriched with frozen-thawed healthy functional human exogenous mitochondria, wherein the renal disease or disorder is not a primary mitochondrial disease or disorder caused by a pathogenic mutation in mitochondrial DNA or by a pathogenic mutation in nuclear DNA encoding a mitochondrial molecule.

In another aspect, the present invention provides a pharmaceutical composition for use in treating a renal disease, disorder or a symptom thereof in a human patient in need of such treatment, the composition comprising at least $10^5$ to $2 \times 10^7$ human stem cells per kilogram bodyweight of the patient in a pharmaceutically acceptable liquid medium capable of supporting the viability of the cells, wherein the human stem cells are enriched with frozen thawed healthy functional human exogenous mitochondria, wherein the renal disease or disorder is not a primary mitochondrial disease or disorder caused by a pathogenic mutation in mitochondrial DNA or by a pathogenic mutation in nuclear DNA encoding a mitochondrial protein.

In some embodiments, the enrichment comprises introducing into the stem cells a dose of mitochondria of at least 0.088 up to 176 milliunits of CS activity per million cells.

In further embodiments, the enrichment comprises contacting the stem cells with a dose of mitochondria of 0.88 up to 17.6 milliunits of CS activity per million cells. In some embodiments, the dose of isolated mitochondria is added to the recipient cells at the desired concentration. The ratio of the number of mitochondria donor cells versus the number of mitochondria recipient cells is a ratio above 2:1 (donor cells vs. recipient cells). In typical embodiments, the ratio is at least 5, alternatively at least 10 or higher. In specific embodiments, the ratio of donor cells from which mitochondria are collected to recipient cells is at least 20, 50, 100 or possibly even higher. Each possibility is a separate embodiment.

In certain embodiments, the healthy functional human exogenous mitochondria are syngeneic or allogeneic. In certain embodiments, the healthy functional human exogenous mitochondria are syngeneic. In certain embodiments, the healthy functional human exogenous mitochondria are autologous i.e., of the same maternal bloodline. In certain embodiments, the healthy functional human exogenous mitochondria are allogeneic.

In certain embodiments, the disease or disorder is associated with acquired mitochondrial dysfunction. In other embodiments, the disease or disorder is not associated with acquired mitochondrial dysfunction.

In certain embodiments, the disease or disorder is selected from the group consisting of nephropathy, nephritis, nephrosis, nephritic syndrome, nephrotic syndrome, Fanconi's syndrome and kidney failure. Each possibility represents a separate embodiment of the present invention.

In certain embodiments, the symptom is selected from the group consisting of, low blood alkaline phosphatase levels, low blood magnesium levels, high blood creatinine levels, low blood bicarbonate levels, low blood base excess levels, high urine glucose/creatinine ratios, high urine chloride/creatinine ratios, high urine sodium/creatinine ratios, high blood lactate levels, high urine magnesium/creatinine ratios, high urine potassium/creatinine ratios, high urine calcium/creatinine ratios, and high blood urea levels. Each possibility represents a separate embodiment of the present invention.

In certain embodiments the pharmaceutical composition is administered by systemic administration. In alternative embodiments, the pharmaceutical composition is administered directly to the renal system. In certain embodiments, the pharmaceutical composition is administered directly to a kidney, the renal pelvis, the adrenal gland, the renal artery, the inferior vena cava, the abdominal aorta, the common iliac artery or the common iliac vein. Each possibility represents a separate embodiment of the present invention.

In certain embodiments, the pharmaceutical composition comprises about $10^6$ mitochondrially-enriched human stem cells per kilogram body weight of the patient. In certain embodiments, the pharmaceutical composition comprises a total of $5 \times 10^5$ to $5 \times 10^9$ human stem cells enriched with human mitochondria.

In certain embodiments, the mitochondrially-enriched human stem cells have at least one of: (i) an increased mitochondrial DNA content; (ii) an increased level of CS activity; (iii) an increased content of at least one mitochondrial protein selected from SDHA and COX1; (iv) an increased rate of $O_2$ consumption; (v) an increased rate of ATP production; or (vi) any combination thereof, relative to the corresponding level in the stem cells prior to mitochondrial enrichment. Each possibility represents a separate embodiment of the present invention.

In certain embodiments, the human stem cells are obtained or derived from the patient before enrichment with the exogenous mitochondria.

In certain embodiments, the human stem cells are obtained or derived from a donor different than the patient before enrichment with the exogenous mitochondria. In certain embodiments, the donor of the stem cells is at least partly HLA-matched with the patient. In certain embodiments, the method described above further comprises a step of administering to the patient an agent which prevents, delays, minimizes or abolishes an adverse immunogenic reaction between the patient and the mitochondrially-enriched human stem cells. In certain embodiments, the adverse immunogenic reaction is a graft-versus-host disease (GvHD).

In certain embodiments, the human stem cells are $CD34^+$. In certain embodiments, the human stem cells are hematopoietic stem cells. In certain embodiments, the human stem cells are mesenchymal stem cells. In certain embodiments, the human stem cells are pluripotent stem cells (PSCs) or induced pluripotent stem cells (iPSCs).

In certain embodiments, the method described above further comprises the preceding steps of isolating, deriving or obtaining human stem cells, and introducing healthy functional human exogenous mitochondria into the human stem cells, thus producing the mitochondrially-enriched human stem cells. In certain embodiments, the method comprises (a) freezing the human stem cells, (b) thawing the human stem cells, and (c) introducing healthy functional human exogenous mitochondria into the human stem cells. In certain embodiments, the human stem cells are isolated, derived or obtained from cells of the bone marrow. In other embodiments, the human stem cells are isolated, derived or obtained from adipose tissue, oral mucosa, skin fibroblasts, blood or umbilical cord blood. Each possibility represents a separate embodiment of the present invention.

In certain embodiments, the human stem cells have undergone at least one freeze-thaw cycle prior to introducing healthy functional human exogenous mitochondria into said human stem cells. In certain embodiments, the method comprises (a) freezing the healthy functional human exogenous mitochondria, (b) thawing the healthy functional human exogenous mitochondria, and (c) introducing the healthy functional human exogenous mitochondria into the human stem cells. In certain embodiments, the human stem cells are isolated, derived or obtained from cells of the bone marrow, adipose tissue, oral mucosa, skin fibroblasts, blood or umbilical cord blood. In certain embodiments, the healthy functional human exogenous mitochondria are isolated or obtained from placenta, placental cells grown in culture or blood cells. Each possibility represents a separate embodiment of the present invention.

In certain embodiments, the human stem cells have undergone at least one freeze-thaw cycle after enrichment with the healthy functional human exogenous mitochondria. In certain embodiments, the method further comprises the additional steps of (a) freezing the human stem cells enriched with healthy functional human exogenous mitochondria, and (b) thawing the human stem cells enriched with healthy functional human exogenous mitochondria, prior to administering the human stem cells enriched with healthy functional human exogenous mitochondria to the patient.

In certain embodiments, the healthy functional human exogenous mitochondria constitute at least 3% of the total mitochondria in the mitochondrially enriched human stem cells. In certain embodiments, the healthy functional human exogenous mitochondria constitute at least 10% of the total mitochondria in the mitochondrially enriched human stem cells. In certain embodiments, the healthy functional human exogenous mitochondria constitute at least 1% of the total mitochondria in the mitochondrially enriched human stem cells.

In certain embodiments, the pharmaceutical composition further comprises non-enriched stem cells, megakaryocytes, erythrocytes, mast cells, myeloblasts, basophils, neutrophils, eosinophils, monocytes, macrophages, natural killer (NK) cells, small lymphocytes, T lymphocytes, B lymphocytes, plasma cells, reticular cells, or any combination thereof. Each possibility represents a separate embodiment of the present invention.

The present invention further provides, in another aspect, a plurality of human stem cells enriched with healthy functional human exogenous mitochondria, for use in treating renal disorders.

The present invention further provides, in another aspect, a pharmaceutical composition comprising a therapeutically-effective amount of a plurality of human stem cells enriched with healthy functional human exogenous mitochondria, for use in treating renal disorders as described above.

In certain embodiments, the pharmaceutical composition described above is for use in treating a renal disease or a renal disorder or a symptom thereof, wherein the renal disease or disorder is not a primary mitochondrial disease or disorder caused by a pathogenic mutation in mitochondrial DNA or by a pathogenic mutation in nuclear DNA encoding a mitochondrial molecule, such as, for example, a protein or a peptide. In certain embodiments, the symptom is selected from the group consisting of, low blood alkaline phosphatase levels, low blood magnesium levels, high blood creatinine levels, low blood bicarbonate levels, low blood base excess levels, high urine glucose/creatinine ratios, high urine chloride/creatinine ratios, high urine sodium/creatinine ratios, high blood lactate levels, high urine magnesium/creatinine ratios, high urine potassium/creatinine ratios, high urine calcium/creatinine ratios, and high blood urea levels. Each possibility represents a separate embodiment of the present invention.

The present invention further provides, in another aspect, a method for treating a renal disease or a renal disorder or a symptom thereof in a patient in need thereof, comprising administering to the patient the pharmaceutical composition described above, wherein the renal disease or disorder is not a primary mitochondrial disease or disorder caused by a pathogenic mutation in mitochondrial DNA or by a pathogenic mutation in nuclear DNA encoding a mitochondrial molecule, such as, for example, a protein or a peptide.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. Further limitations and disadvantages of conventional and traditional approaches will become apparent to one of skill in the art, though comparison of such systems with some aspects of the present invention as set forth in the remainder of the present application with reference to the drawings.

DETAILED DESCRIPTION OF THE INVENTION

Figure 1:
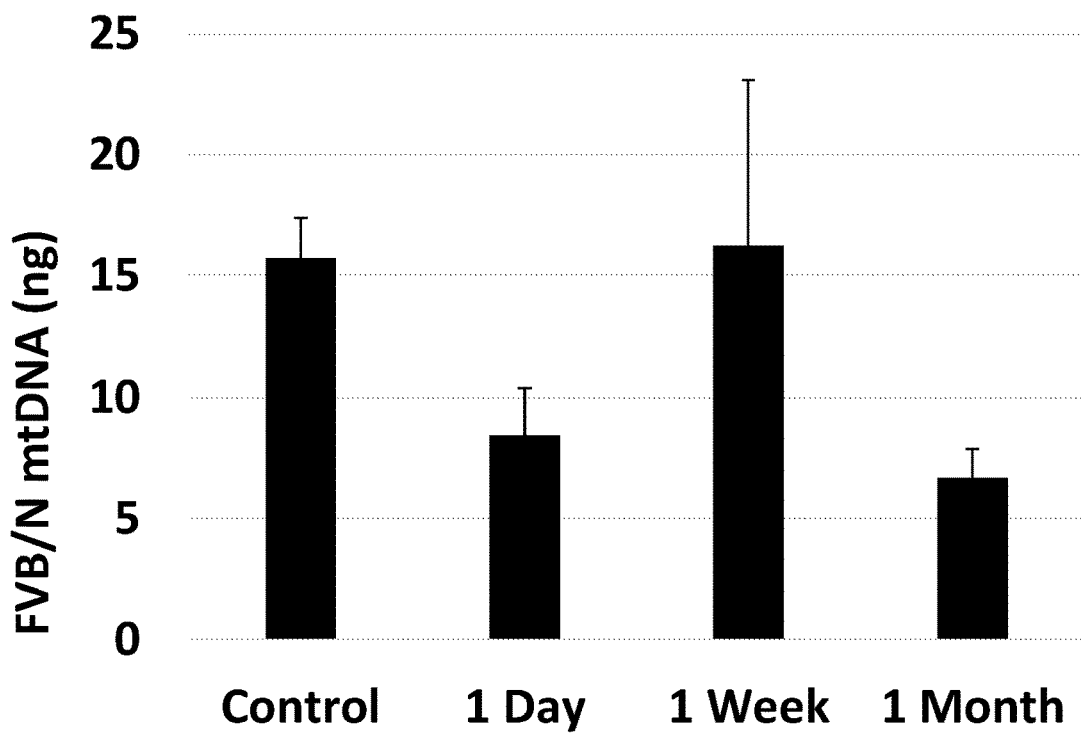
FIG. 1 is a bar graph illustrating the amount of mutated mtDNA (FVB/N mtDNA) in the bone marrow of mice as a function of time post administration of murine cells.

It has now been shown for the first time that human stem cells loaded with healthy functional exogenous mitochondria can achieve in-vivo systemic delivery of healthy functional mitochondria to organs, tissues and cells in patients suffering from diseases and disorders of diversified etiologies.

Without being limited to any theory or mechanism, it is now hypothesized that functional exogenous mitochondria can enter human stem cells, and thereby increase their mitochondrial activity and energy production. Such cells may hypothetically reach distal organs through circulation, and transfer at least part of their functional mitochondria to cells in other organs.

Again without being limited to any theory or mechanism, it is now further hypothesized that augmented stem cells as described below are recruited to damaged or diseased organs and improve their function either by e.g. mitochondrial transfer, secretion of different factors, differentiation, etc.

More specifically, it has been surprisingly found that a single round of treatment of young Pearson Syndrome (PS) patients by autologous stem cells which went through mitochondria augmentation therapy was sufficient to significantly ameliorate a wide variety of adverse PS-related and PS-independent kidney-related symptoms.

The present invention provides, in one aspect, a method for treating a renal disease, disorder or a symptom thereof in a subject in need of such treatment, wherein the renal disease or disorder is not a primary mitochondrial disease or disorder caused by a pathogenic mutation in mitochondrial DNA or by a pathogenic mutation in nuclear DNA encoding a mitochondrial molecule, the method comprising the step of administering a pharmaceutical composition comprising a plurality of stem cells to the patient, wherein the stem cells are enriched with healthy functional exogenous mitochondria. In some embodiments, the subject is a mammalian subject and the stem cells are mammalian stem cells. In certain embodiments, the subject is a human subject and the stem cells are human stem cells.

In some embodiments, the present invention provides a method for treating a renal disease, disorder or a symptom thereof in a human patient in need of such treatment, wherein the renal disease or disorder is not a primary mitochondrial disease or disorder caused by a pathogenic mutation in mitochondrial DNA or by a pathogenic mutation in nuclear DNA encoding a mitochondrial molecule, the method comprising the step of administering a pharmaceutical composition comprising a plurality of human stem cells to the patient, wherein the human stem cells are enriched with healthy functional human exogenous mitochondria.

As used herein and in the claims, the terms "mitochondrial disease" and "primary mitochondrial disease" may be interchangeably used. The terms "mitochondrial disease" and "primary mitochondrial disease" refer to a congenital mitochondrial disease which is diagnosed by a known or indisputably pathogenic mutation in the mitochondrial DNA, or by mutations in genes of the nuclear DNA, whose gene products are imported into the mitochondria. The phrase "the renal disease or disorder is not a primary mitochondrial disease" means that the renal disease or disorder is not primarily diagnosed by a known or indisputably pathogenic mutation in the mitochondrial DNA, or by mutations in genes of the nuclear DNA whose gene products are imported into the mitochondria. The renal disease or disorder which is the object of treatment of the present invention is not necessarily operably linked to a mutation, or to a group of mutations, in a coding region in mitochondrial or nuclear DNA, coding for a mitochondrial molecule.

In some embodiments, the renal disease or disorder is associated with acquired mitochondrial dysfunction. In other embodiments, the disease or disorder is not associated with acquired mitochondrial dysfunction. In some embodiments, the renal disease or disorder is associated with a secondary mitochondrial dysfunction. In other embodiments, the renal disease or disorder is not associated with a secondary mitochondrial dysfunction.

As used herein, the term "secondary mitochondrial dysfunction" and "acquired mitochondrial dysfunction" are used interchangeably and refer to an acquired mitochondrial dysfunction that can accompany many non-primary mitochondrial diseases and may be caused by genes encoding neither function nor production of the oxidative phosphorylation (OXPHOS) proteins. Secondary mitochondrial dysfunction can also be caused by environmental factors which can cause oxidative stress.

In another aspect, the present invention provides a pharmaceutical composition for use in treating a renal disease, disorder or a symptom thereof in a human patient in need of such treatment, the composition comprising a plurality of human stem cells in a pharmaceutically acceptable liquid medium capable of supporting the viability of the cells, wherein the human stem cells are enriched with frozen thawed healthy functional human exogenous mitochondria, wherein the renal disease or disorder is not a primary mitochondrial disease or disorder caused by a pathogenic mutation in mitochondrial DNA or by a pathogenic mutation in nuclear DNA encoding a mitochondrial protein.

In some embodiments, the pharmaceutical composition comprises at least $10^5$ to $4\times10^7$ mitochondrially-enriched human stem cells per kilogram bodyweight of the patient. In some embodiments, the pharmaceutical composition comprises at least $10^5$ to $2\times10^7$ mitochondrially-enriched human stem cells per kilogram bodyweight of the patient. In some embodiments, the pharmaceutical composition comprises at least $5\times10^5$ to $1.5\times10^7$ mitochondrially-enriched human stem cells per kilogram bodyweight of the patient. In some embodiments, the pharmaceutical composition comprises at least $10^6$ to $10^7$ mitochondrially-enriched human stem cells per kilogram bodyweight of the patient. In other embodiments, the pharmaceutical composition comprises at least $10^5$ or at least $10^6$ mitochondrially-enriched human stem cells per kilogram bodyweight of the patient. Each possibility represents a separate embodiment of the present invention. In some embodiments, the pharmaceutical composition comprises a total of at least $5\times10^5$ up to $5\times10^9$ mitochondrially-enriched human stem cells. In some embodiments, the pharmaceutical composition comprises a total of at least $10^6$ up to $10^9$ mitochondrially-enriched human stem cells. In other embodiments, the pharmaceutical composition comprises a total of at least $2\times10^6$ up to $5\times10^8$ mitochondrially-enriched human stem cells.

In certain embodiments, the healthy functional human mitochondria are autologous or allogeneic. In certain embodiments, the healthy functional human mitochondria are autologous. In certain embodiments, the healthy functional human mitochondria are allogeneic.

In certain embodiments, the method is for treating a renal disease, disorder or a symptom thereof in a human patient in need of such treatment, the method comprising the step of administering a pharmaceutical composition comprising a plurality of human stem cells to the patient, wherein the human stem cells are enriched with healthy functional autologous or allogeneic mitochondria without a pathogenic mutation in mitochondrial DNA and without a mutated mitochondrial protein encoded by nuclear DNA, and wherein the renal disease or disorder is not a primary mitochondrial disease or disorder caused by a pathogenic mutation in mitochondrial DNA or by a pathogenic mutation in nuclear DNA encoding a mitochondrial molecule (such as a protein, peptide, nucleic acid, and the like).

In some embodiments, there is provided a method for treating a renal disease, disorder or a symptom thereof in a human patient in need of such treatment, the method comprising the step of administering a pharmaceutical composition comprising a plurality of human stem cells to the patient, wherein the human stem cells are enriched with healthy functional exogenous mitochondria without a pathogenic mutation in mitochondrial DNA, and wherein the renal disease or disorder is not a primary mitochondrial disease or disorder caused by a pathogenic mutation in mitochondrial DNA or by a pathogenic mutation in nuclear DNA.

The term "method" as used herein generally refers to manners, means, techniques and procedures for accomplishing a given task, including, but not limited to, those manners, means, techniques and procedures either known to, or readily developed from known manners, means, techniques and procedures by practitioners of the chemical, pharmacological, biological, biochemical and medical arts.

The term "treating" as used herein includes the diminishment, alleviation, or amelioration of at least one symptom associated or induced by a disease or condition. The term "treating" as used herein also includes preventative (e.g., prophylactic), palliative and curative treatment.

The term "pharmaceutical composition" as used herein refers to any composition comprising at least one biologically active agent. As used herein, the term "pharmaceutical composition" further refers to a composition comprising an active pharmaceutical ingredient to be delivered to a subject, for example, for therapeutic, prophylactic, diagnostic, preventative or prognostic effect. The term "pharmaceutical composition" as used herein further refers to any composition comprising human stem cells, optionally further comprising a medium or carrier in which the cells are maintained in a viable state. In certain embodiments, the pharmaceutical composition comprises the active pharmaceutical ingredient and a pharmaceutically acceptable carrier. As used herein, the term "pharmaceutically acceptable carrier" includes any and all solvents, dispersion media, coatings, anti-bacterial and anti-fungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In certain embodiments, the pharmaceutical composition is frozen. In certain embodiments, the pharmaceutical composition is thawed. In certain embodiments, the pharmaceutical composition is thawed prior to being administered. In certain embodiments, the pharmaceutical composition is thawed up to 24 hours prior to being administered. In certain embodiments, the enriched human stem cells are the only active ingredient in the pharmaceutical composition.

The term "biologically active agent" as used herein refers to any molecule capable of eliciting a response in a biological system such as, for example, living cell(s), tissue(s), organ(s), and being(s). Non-limiting examples of biologically active agents according to the present inventions include cells, intact mitochondria, mitochondrial DNA, and a mitochondrial protein. According to the principles of the present invention, a plurality of human stem cells enriched with healthy functional human mitochondria without a pathogenic mutation in mitochondrial DNA is a biologically active agent.

The phrases "a renal disease or a renal disorder" and "kidney disease" as used herein refer to damage to, or a disease of, a kidney.

The term "therapeutically-effective amount" or "an effective amount" refers to the amount of an active agent or composition that is required to confer a therapeutic effect on the treated patient. Effective doses will vary, as recognized by those skilled in the art, e.g. depending on route of administration, excipient usage, and the possibility of co-usage with other therapeutic treatment.

The term "stem cells" as used herein generally refers to any human stem cells. Stem cells are undifferentiated cells that can differentiate into other types of cells and can divide to produce more of the same type of stem cells. Stem cells can be either totipotent or pluripotent. The term "human stem cells" as used herein generally refers to all stem cells naturally found in humans, and to all stem cells produced or derived ex-vivo and are compatible with humans. A "progenitor cell", like a stem cell, has a tendency to differentiate into a specific type of cell, but is already more specific than a stem cell and is pushed to differentiate into its "target" cell. The most important difference between stem cells and progenitor cells is that stem cells can replicate indefinitely, whereas progenitor cells can divide only a limited number of times. The term "human stem cells" as used herein further includes "progenitor cells" and "non-fully-differentiated stem cells".

According to the principles of the present invention, stem cells are enriched with healthy functional human exogenous mitochondria prior to being administered to a patient in need in order to increase the number and/or function of mitochondria in them. Without being limited to any theory or mechanism, the increased number and/or function of mitochondria in the administered stem cells is responsible for the various therapeutic effects exemplified herein for the first time in human patients. The term "enriching" as used herein refers to any action designed to increase the mitochondrial content, e.g. the number of intact mitochondria, or the functionality of mitochondria of a mammalian cell. In particular, stem cells enriched with functional mitochondria will show enhanced mitochondrial function compared to the same stem cells prior to enrichment. The term "enriching" as used herein further refers to any action performed ex vivo, which increases the mitochondrial content, e.g. the number of intact, functional, healthy, mitochondria, of a human cell. According to the principles of the present invention, healthy functional human exogenous mitochondria are introduced into human stem cells, thus enriching these cells with healthy functional human mitochondria.

It should be understood that such enrichment changes the mitochondrial content of the human stem cells: while naïve human stem cells substantially have one population of host/autologous mitochondria, human stem cells enriched with exogenous mitochondria substantially have two populations of mitochondria-one population of host/autologous/endogenous mitochondria and another population of the introduced mitochondria (i.e., the exogenous mitochondria). Thus, the term "enriched" relates to the state of the cells after receiving/incorporation exogenous mitochondria. Determining the number and/or ratio between the two populations of mitochondria is straightforward, as the two populations may differ in several aspects e.g. in their mitochondrial DNA. Therefore, the phrase "human stem cells enriched with healthy functional human mitochondria" is equivalent to the phrase "human stem cells comprising endogenous mitochondria and healthy functional exogenous mitochondria". For example, human stem cells which comprise at least 1% and less than 33% healthy functional exogenous mitochondria of the total mitochondria, are considered comprising host/autologous/endogenous mitochondria and healthy functional exogenous mitochondria in a ratio of 99:1 to a ratio 67:33. For example, "3% of the total mitochondria" means that after enrichment the original (endogenous) mitochondrial content is 97% of the total mitochondria and the introduced (exogenous) mitochondria is 3% of the total mitochondria—this is equivalent to (3/97=) 3.1% enrichment. Another example—"33% of the total mitochondria" means that after enrichment, the original (endogenous) mitochondrial content is 67% of the total mitochondria and the introduced (exogenous) mitochondria is 33% of the total mitochondria—this is equivalent to (33/67=) 49.2% enrichment.

It should be understood that the phrase "human stem cells enriched with healthy functional exogenous mitochondria" as used herein refers to human stem cells comprising healthy functional mitochondria, wherein the healthy functional mitochondria are of a different origin than the human stem cells, i.e. these mitochondria are obtained/derived/isolated from an exogenous source. The presence of "exogenous", "foreign" or "non-original" healthy functional mitochondria within human stem cells serves as evidence that these cells are enriched with said mitochondria. A person of average skill in the art would know how to determine that human stem cells comprise exogenous allogeneic mitochondria from different origins based on well-known methods in the art (see e.g. Zander J. et al., Forensic Sci. Int. Genet., 2017, Vol. 29, pages 242-249). Such methods can be based e.g. on genetic differences between different mitochondria populations within a human stem cell or within a plurality of human stem cells. For example, in humans, the mitochondrial DNA encodes 37 genes (Nature. 290 (5806): 457-65), thus by sequencing the mtDNA one can easily determine the existence of 1, 2 or more different populations of mtDNA in a human stem cell or in a plurality of human stem cells.

In some embodiments, enrichment of the stem cells with healthy functional human exogenous mitochondria comprises washing the mitochondrially-enriched stem cells after incubation of the human stem cells with said healthy functional human exogenous mitochondria. This step provides a composition of the mitochondrially-enriched stem cells substantially devoid of cell debris or mitochondrial membrane remnants and mitochondria that did not enter the stem cells. In some embodiments, washing comprises centrifugation of the mitochondrially-enriched stem cells after incubation of the human stem cells with said healthy functional human exogenous mitochondria. According to some embodiments, the pharmaceutical composition comprising the mitochondrially-enriched human stem cells is separated from free mitochondria, i.e., mitochondria that did not enter the stem cells, or other cell debris. According to some embodiments, the pharmaceutical composition comprising the mitochondrially-enriched human stem cells does not comprise a detectable amount of free mitochondria.

The terms "healthy functional mitochondria", "healthy functional human mitochondria", "healthy functional exogenous mitochondria", "healthy functional human exogenous mitochondria", healthy functional human exogenous mitochondria without a pathogenic mutation in mitochondrial DNA or in a mitochondrial protein" and "healthy functional human exogenous mitochondria without a pathogenic mutation in mitochondrial DNA or in a mitochondrial molecule" may interchangeably be used and refer to mitochondria displaying normal, non-pathologic levels of activity. The activity of mitochondria can be measured by a variety of methods well known in the art, such as Tetramethylrhodamine Ethyl Ester Perchlorate (TMRE) staining, $O_2$ consumption, ATP production, and CS activity level.

In certain embodiments, the human stem cells enriched with healthy functional exogenous mitochondria comprise a mixture of healthy functional mitochondria of different origins. In certain embodiments, one of the origins of the mixture of healthy functional mitochondria is the same as the origin of the human stem cells. In certain embodiments, none of the origins of the mixture of healthy functional mitochondria is the origin of the human stem cells. In certain embodiments, the human stem cells enriched with healthy functional mitochondria comprise healthy functional mitochondria of a single origin which is different than the origin of the human stem cells.

As the introduction of healthy functional exogenous mitochondria to human stem cells may increase the total number/content of healthy functional mitochondria in these cells, it should further be understood that the phrase "human stem cells enriched with healthy functional mitochondria" as used herein may, in certain embodiments, refer to human stem cells comprising increased amounts of healthy functional mitochondria, either, endogenous, from the stem cells or exogenous, from a different source or origin.

The term "healthy mitochondria" or "functional mitochondria" refers to normally-functioning mitochondria. The term "healthy mitochondrial DNA" or "normal mitochondrial DNA" refers to mitochondrial DNA which does not include a mutation which affects the normal function of the mitochondria. The term "functional mitochondria" as used herein refers to mitochondria displaying normal, non-pathologic levels of activity. The activity of mitochondria can be measured by a variety of methods well known in the art, such as membrane potential, $O_2$ consumption, ATP production, and CS activity level. The term "functional mitochondria" and "healthy mitochondria" are used interchangeably, and further refer to mitochondria that exhibit parameters indicative of normal mtDNA, normal levels of oxygen consumption and ATP production.

The term "associated with" in connection with the relationship between a mutation in mitochondrial DNA and a disease or disorder generally means that the mutation in mitochondrial DNA is at least partly responsible to at least one of the symptoms of the disease or disorder, either directly or indirectly, either alone or in combination with other factors, by any biological mechanism. The term "mutation" as used herein refers to a deletion, an insertion or a point mutation which affects the structure and/or function of a molecule, e.g. an RNA molecule or a protein molecule, encoded by DNA.

In certain embodiments, the pathogenic mutation in mitochondrial DNA or the pathogenic mutation in nuclear DNA is not in a gene encoding a mitochondrial molecule. In certain embodiments, the pathogenic mutation in mitochondrial DNA or the pathogenic mutation in nuclear DNA is not in a gene encoding a mitochondrial protein. In certain embodiments, the pathogenic mutation in mitochondrial DNA or the pathogenic mutation in nuclear DNA is not in a gene encoding a mitochondrial enzyme. In certain embodiments, the pathogenic mutation in mitochondrial DNA or the pathogenic mutation in nuclear DNA is not in a gene encoding a mitochondrial peptide. In certain embodiments, the pathogenic mutation in mitochondrial DNA or the pathogenic mutation in nuclear DNA is not in a gene encoding a mitochondrial RNA molecule.

In certain embodiments, the disease or disorder is selected from the group consisting of nephropathy, nephritis, nephrosis, nephritic syndrome, nephrotic syndrome, Fanconi's syndrome and kidney failure. Each possibility represents a separate embodiment of the present invention.

It is to be understood explicitly that for diseases associated or caused by genetic abnormalities the methods and compositions of the present invention will be useful to alleviate the symptoms of the disease rather than to treat the underlying pathology.

In certain embodiments, the symptom is selected from the group consisting of inability to gain weight, low blood alkaline phosphatase levels, low blood magnesium levels, high blood creatinine levels, low blood bicarbonate levels, low blood base excess levels, high urine glucose/creatinine ratios, high urine potassium/creatinine ratios, high urine chloride/creatinine ratios, high urine sodium/creatinine ratios, high blood lactate levels, high urine magnesium/creatinine ratios, high urine calcium/creatinine ratios, high blood urea levels and low ATP content in lymphocytes. Each possibility represents a separate embodiment of the present invention. In certain embodiments, the symptom is a plurality of symptoms. It should be understood that defining symptoms as "high" and "low" correspond to "detectably higher than normal" and "detectably lower than normal", respectively, wherein the normal level is the corresponding level in a plurality of healthy subjects.

In certain embodiments, the stem cells substantially comprise mitochondrial DNA of a single origin. In certain embodiments, the stem cells substantially comprise mitochondria of a single mitochondrial DNA haplogroup. In human genetics, the term "a human mitochondrial DNA haplogroup" is used to refer to a haplogroup defined by differences in human mitochondrial DNA. The term "haplogroup" as used herein further refers to a genetic population group of people who share a common ancestor on the matriline. Mitochondrial haplogroup is determined by sequencing.

In certain embodiments, the stem cells comprise mitochondrial DNA of two or more origins. In certain embodiments, the stem cells comprise mitochondria of two or more mitochondrial DNA haplogroups. In certain embodiments, the stem cells comprise functional mitochondria of a mitochondrial DNA haplogroup selected from the group consisting of haplogroup J and haplogroup V.

In certain embodiments, the patient experiences impaired physical performance as determined by an aerobic MET test, by an IPMDS/QoL questionnaire, by a 30 seconds Sit-to-Stand test, or by a 6-minute walk test (SMWT). Each possibility represents a separate embodiment of the present invention.

In certain embodiments, the pharmaceutical composition is administered directly to the renal system. In certain embodiments, the pharmaceutical composition is administered directly to a kidney, the renal pelvis, a ureter, the urinary bladder, the urethra, the adrenal gland, the renal artery, the renal vein, the inferior vena cava, the abdominal aorta, the common iliac artery or the common iliac vein. Each possibility represents a separate embodiment of the present invention.

In certain embodiments, the pharmaceutical composition comprises at least $1*10^4$, at least $1*10^5$, at least $1*10^6$, or at least $1*10^7$ mitochondrially-enriched human stem cells. Each possibility represents a separate embodiment of the present invention. In certain embodiments, the pharmaceutical composition comprises at least $10^4$ mitochondrially-enriched human stem cells. In certain embodiments, the pharmaceutical composition comprises about $1*10^4$ to about $1*10^8$ mitochondrially-enriched human stem cells. In certain embodiments, the pharmaceutical composition comprises about $1*10^4$ to $1*10^9$, $1*10^5$ to $1*10^9$, $1*10^6$ to $1*10^9$, or $1*10^7$ to $1*10^9$ mitochondrially-enriched human stem cells. Each possibility represents a separate embodiment of the present invention. In certain embodiments, the pharmaceutical composition comprises at least $10^3$ mitochondrially-enriched human stem cells. In certain embodiments, the pharmaceutical composition comprises at least about $10^5$ mitochondrially-enriched human stem cells per kilogram body weight of the patient. In certain embodiments, the pharmaceutical composition is administered by parenteral administration. In certain embodiments, the pharmaceutical composition is administered by systemic administration. In certain embodiments, the pharmaceutical composition is administered intravenously to the patient. In certain embodiments, the pharmaceutical composition is administered by intravenous infusion. In certain embodiments, the pharmaceutical composition comprises at least $1*10^5$, at least $1*10^6$, or at least $1*10^7$ mitochondrially-enriched human stem cells. In certain embodiments, the pharmaceutical composition comprises about $1*10^6$ to about $1*10^8$ mitochondrially-enriched human stem cells. In certain embodiments, the pharmaceutical composition comprises at least about $1*10^5$, at least $1*10^6$, or at least $1*10^7$ mitochondrially-enriched human stem cells per kilogram body weight of the patient. In certain embodiments, the pharmaceutical composition comprises about $1*10^5$ to about $1*10^7$ mitochondrially-enriched human stem cells per kilogram body weight of the patient.

In certain embodiments, the level of mitochondrial enrichment in the mitochondrially-enriched human stem cells is determined by: (i) the levels of host (endogenous) mitochondrial DNA and exogenous mitochondrial DNA; (ii) the level of citrate synthase or the level of citrate synthase activity; or (iii) both (i) and (ii). Each possibility represents a separate embodiment of the present invention.

In certain embodiments, the method comprises administering to the patient a pharmaceutical composition comprising a therapeutically-effective amount of at least about $1*10^4$ stem cells per kilogram body weight of the patient. In certain embodiments, the method comprises administering to the patient a pharmaceutical composition comprising a therapeutically-effective amount of at least about $1*10^5$ stem cells per kilogram body weight of the patient. In certain embodiments, the method comprises administering to the patient a pharmaceutical composition comprising a therapeutically-effective amount of at least about $1*10^6$ stem cells per kilogram body weight of the patient.

In certain embodiments, the method comprises administering to the patient a pharmaceutical composition comprising a therapeutically-effective amount of about $1*10^4$ to about $1*10^8$ stem cells per kilogram body weight of the patient. In certain embodiments, the method comprises administering to the patient a pharmaceutical composition comprising a therapeutically-effective amount of about $1*10^5$ to about $1*10^7$ stem cells per kilogram body weight of the patient. In certain embodiments, the method comprises administering to the patient a pharmaceutical composition comprising a therapeutically-effective amount of about $5*10^4$ to about $5*10^6$ stem cells per kilogram body weight of the patient.

In certain embodiments, the method comprises administering to the patient a pharmaceutical composition comprising a therapeutically-effective amount of about $1*10^4$ to about $4*10^8$ stem cells per kilogram body weight of the patient. In certain embodiments, the method comprises administering to the patient a pharmaceutical composition comprising a therapeutically-effective amount of about $1*10^5$ to about $4*10^7$ stem cells per kilogram body weight of the patient. In certain embodiments, the method comprises administering to the patient a pharmaceutical composition comprising a therapeutically-effective amount of about $1*10^6$ to about $4*10^6$ stem cells per kilogram body weight of the patient.

In certain embodiments, the mitochondrially-enriched human stem cells are obtained or derived from the patient himself, before enrichment with the exogenous functional mitochondria.

In certain embodiments, the mitochondrially-enriched human stem cells are obtained or derived from a donor different than the patient before enrichment of the cells with exogenous mitochondria. In certain embodiments, the donor is at least partly human leukocyte antigen (HLA)-matched with the patient. In certain embodiments, the method described above further comprises a step of administering to the patient an agent which prevents, delays, minimizes or abolishes an adverse immunogenic reaction between the patient and the mitochondrially-enriched human stem cells. In certain embodiments, the adverse immunogenic reaction is a graft-versus-host disease (GvHD).

In certain embodiments, the stem cells are pluripotent stem cells (PSCs). In certain embodiments, the stem cells are induced pluripotent stem cells (iPSCs). As used herein the term "pluripotent stem cells (PSCs)" refers to cells that can propagate indefinitely, as well as give rise to a plurality of cell types in the body, for example neuronal cells. Totipotent stem cells are cells that can give rise to every other cell type in the body. Embryonic stem cells (ESCs) are totipotent stem cells and induced pluripotent stem cells (iPSCs) are pluripotent stem cells. As used herein the term "induced pluripotent stem cells (iPSCs)" refers to a type of pluripotent stem cell that can be generated from human adult somatic cells. In some embodiments, the PSCs are non-embryonic stem cells. As used herein the term "embryonic stem cells (ESC)" refers to a type of totipotent stem cell derived from the inner cell mass of a blastocyst.

In certain embodiments, the stem cells are mesenchymal stem cells. In certain embodiments, the stem cells are CD34$^+$ cells. The term "CD34$^+$ cells" as used herein refers to stem cells characterized as being CD34-positive, regardless of their origin. The term further refers to hematopoietic stem cells characterized as being CD34-positive that are obtained from stem cells or mobilized from bone marrow or obtained from umbilical cord blood. As used herein, the term "CD34$^+$ cells" denotes cells that express the surface marker protein CD34. Expression of CD34 can be determined by immunofluorescence analysis or FACS analysis using an antibody directed against CD34. Hematopoietic progenitor cell antigen CD34, also known as CD34 antigen, is a protein that in humans is encoded by the CD34 gene.

In certain embodiments, the CD34$^+$ cells are umbilical cord cells. In certain embodiments, the CD34$^+$ cells are bone marrow cells. In certain embodiments, the CD34$^+$ cells are hematopoietic cells. In certain embodiments, the CD34$^+$ cells are mesenchymal stem cells. In certain embodiments, the CD34$^+$ cells are endothelial progenitor cells. In certain embodiments, the CD34$^+$ cells are endothelial cells of blood vessels. In certain embodiments, the CD34$^+$ cells are mast cells. In certain embodiments, the CD34$^+$ cells are a subpopulation dendritic cells (which are factor XIIIa-negative). In certain embodiments, the CD34$^+$ cells are Long-Term Hematopoietic Stem Cells (LT-HSCs). In certain embodiments, the CD34$^+$ cells are human HSCs cells. In certain embodiments, the CD34$^+$ cells are HLA-matched to the patient. In certain embodiments, the CD34+ cells are HLA-matched with the patient. In certain embodiments, the CD34+ cells are autologous to the patient.

In certain embodiments, the stem cells are derived from adipose tissue, oral mucosa, peripheral blood or umbilical cord blood. Each possibility represents a separate embodiment of the present invention. In certain embodiments, the stem cells are derived from bone marrow cells. The term "bone marrow cells" as used herein generally refers to all human cells naturally found in the bone marrow of humans, and to all cell populations naturally found in the bone marrow of humans. The term "bone marrow stem cells" refers to the stem cell population derived from the bone marrow.

The term "myelopoietic cells" as used herein refers to cells involved in myelopoiesis, e.g. in the production of bone-marrow and of all cells that arise from it, namely, all blood cells.

The term "erythropoietic cells" as used herein refers to cells involved in erythropoiesis, e.g. in the production of red blood cells (erythrocytes).

The term "multi-potential hematopoietic stem cells" or "hemocytoblasts" as used herein refers to the stem cells that give rise to all the other blood cells through the process of hematopoiesis.

The term "common myeloid progenitor" as used herein refers to the cells that generate myeloid cells. The term "common lymphoid progenitor" as used herein refers to the cells that generate lymphocytes.

The term "mesenchymal stem cells" as used herein refers to multipotent stromal cells that can differentiate into a variety of cell types, including neuronal cells, osteoblasts (bone cells), chondrocytes (cartilage cells), myocytes (muscle cells) and adipocytes (fat cells).

In certain embodiments, the pharmaceutical composition may further comprise non-enriched stem cells, megakaryocytes, erythrocytes, mast cells, myeloblasts, basophils, neutrophils, eosinophils, monocytes, macrophages, natural killer (NK) cells, small lymphocytes, T lymphocytes, B lymphocytes, plasma cells, reticular cells, or any combination thereof. Each possibility represents a separate embodiment of the present invention.

In certain embodiments, the method described above further comprises the preceding steps of isolating, deriving or obtaining human stem cells, and introducing healthy functional human exogenous mitochondria into the human stem cells, thus producing the mitochondrially-enriched human stem cells. In certain embodiments, the method comprises (a) freezing the human stem cells, (b) thawing the human stem cells, and (c) introducing healthy functional human exogenous mitochondria into the human stem cells. In certain embodiments, the human stem cells are isolated, derived or obtained from cells of the bone marrow, adipose tissue, oral mucosa, skin fibroblasts, blood or umbilical cord blood. Each possibility represents a separate embodiment of the present invention.

In some embodiments, the method described above further comprises the step of selection of CD34 positive cells from the human stem cells prior to introducing the healthy functional exogenous mitochondria into the cells. Selection of CD34 positive cells can be done by methods known in the art including but not limited to the CliniMACS or Prodigy systems (Miltenyi).

In certain embodiments, the method described above further comprises the preceding steps of isolating or obtaining healthy functional human exogenous mitochondria form a suitable source, and introducing the healthy functional human exogenous mitochondria into human stem cells, thus producing the mitochondrially-enriched human stem cells. In certain embodiments, the method may include the steps of: (a) freezing the healthy functional human exogenous mitochondria, (b) thawing the healthy functional human exogenous mitochondria, and (c) introducing the healthy functional human exogenous mitochondria into the human stem cells. In certain embodiments, the healthy functional human exogenous mitochondria are isolated or obtained from a suitable source, including, but not limited to: placenta, placental cells grown in culture or blood cells. Each possibility represents a separate embodiment of the present invention.

According to the principles of the present invention, the possibility to freeze healthy functional exogenous mitochondria before enriching the human stem cells is crucial for mitochondrial augmentation therapy process as it e.g. provides sufficient time to test functionality and/or certain attributes of the healthy functional exogenous mitochondria, as well as increases the shelf-life of the healthy functional exogenous mitochondria and/or allows the healthy functional exogenous mitochondria to be easily distributed, before enriching the human stem cells.

Without wishing to be bound by any theory or mechanism, mitochondria that have undergone a freeze-thaw cycle demonstrate a comparable oxygen consumption rate following thawing, as compared to control mitochondria that have not undergone a freeze-thaw cycle.

According to some embodiments, the freeze-thaw cycle comprises freezing said functional mitochondria for at least 24 hours prior to thawing. According to other embodiments, the freeze-thaw cycle comprises freezing said functional mitochondria for at least 1 month prior to thawing, several months prior to thawing or longer. Each possibility represents a separate embodiment of the present invention. According to another embodiment, the oxygen consumption of the functional mitochondria after the freeze-thaw cycle is equal or higher than the oxygen consumption of the functional mitochondria prior to the freeze-thaw cycle.

As used herein, the term "freeze-thaw cycle" refers to freezing of the functional mitochondria to a temperature below 0° C., maintaining the mitochondria in a temperature below 0° C. for a defined period of time and thawing the mitochondria to room temperature or body temperature or any temperature above 0° C. which enables treatment of the stem cells with the mitochondria. Each possibility represents a separate embodiment of the present invention. The term "room temperature", as used herein typically refers to a temperature of between 18° C. and 25° C. The term "body temperature", as used herein, refers to a temperature of between 35.5° C. and 37.5° C., preferably 37° C. In another embodiment, mitochondria that have undergone a freeze-thaw cycle are functional mitochondria.

In another embodiment, the mitochondria that have undergone a freeze-thaw cycle were frozen at a temperature of −70° C. or lower. In another embodiment, the mitochondria that have undergone a freeze-thaw cycle were frozen at a temperature of −20° C. or lower. In another embodiment, the mitochondria that have undergone a freeze-thaw cycle were frozen at a temperature of −4° C. or lower. According to another embodiment, freezing of the mitochondria is gradual. According to some embodiment, freezing of mitochondria is through flash-freezing. As used herein, the term "flash-freezing" refers to rapidly freezing the mitochondria by subjecting them to cryogenic temperatures.

In another embodiment, the mitochondria that underwent a freeze-thaw cycle were frozen for at least 30 minutes prior to thawing. According to another embodiment, the freeze-thaw cycle comprises freezing the functional mitochondria for at least 30, 60, 90, 120, 180, 210 minutes prior to thawing. Each possibility represents a separate embodiment of the present invention. In another embodiment, the mitochondria that have undergone a freeze-thaw cycle were frozen for at least 1, 2, 3, 4, 5, 6, 7, 8, 9, 10, 24, 48, 72, 96, or 120 hours prior to thawing. Each freezing time presents a separate embodiment of the present invention. In another embodiment, the mitochondria that have undergone a freeze-thaw cycle were frozen for at least 4, 5, 6, 7, 30, 60, 120, 365 days prior to thawing. Each freezing time presents a separate embodiment of the present invention. According to another embodiment, the freeze-thaw cycle comprises freezing the functional mitochondria for at least 1, 2, 3 weeks prior to thawing. Each possibility represents a separate embodiment of the present invention. According to another embodiment, the freeze-thaw cycle comprises freezing the functional mitochondria for at least 1, 2, 3, 4, 5, 6 months prior to thawing. Each possibility represents a separate embodiment of the present invention.

In another embodiment, the mitochondria that have undergone a freeze-thaw cycle were frozen at −70° C. for at least 30 minutes prior to thawing. Without wishing to be bound by any theory or mechanism, the possibility to freeze mitochondria and thaw them after a long period enables easy storage and use of the mitochondria with reproducible results even after a long period of storage.

According to one embodiment, thawing is at room temperature. In another embodiment, thawing is at body temperature. According to another embodiment, thawing is at a temperature which enables administering the mitochondria according to the methods of the invention. According to another embodiment, thawing is performed gradually.

According to another embodiment, the mitochondria that underwent a freeze-thaw cycle were frozen within a freezing buffer. According to another embodiment, the mitochondria that underwent a freeze-thaw cycle were frozen within the isolation buffer. As used herein, the term "isolation buffer" refers to a buffer in which the mitochondria of the invention have been isolated. In a non-limiting example, the isolation buffer is a sucrose buffer. Without wishing to be bound by any mechanism or theory, freezing mitochondria within the isolation buffer saves time and isolation steps, as there is no need to replace the isolation buffer with a freezing buffer prior to freezing or to replace the freezing buffer upon thawing.

According to another embodiment, the freezing buffer comprises a cryoprotectant. According to some embodiments, the cryoprotectant is a saccharide, an oligosaccharide or a polysaccharide. Each possibility represents a separate embodiment of the present invention. According to another embodiment, the saccharide concentration in the freezing buffer is a sufficient saccharide concentration which acts to preserve mitochondrial function. According to another embodiment, the isolation buffer comprises a saccharide. According to another embodiment, the saccharide concentration in the isolation buffer is a sufficient saccharide concentration which acts to preserve mitochondrial function. According to another embodiment, the saccharide is sucrose.

In certain embodiments, the healthy functional exogenous mitochondria constitute at least 3% of the total mitochondria in the mitochondrially-enriched cell. In certain embodiments, the healthy functional exogenous mitochondria constitute at least 10% of the total mitochondria in the mitochondrially-enriched cell. In some embodiments, the healthy functional exogenous mitochondria constitute at least about 3%, 5%, 10%, 15%, 20%, 25% or 30% of the total mitochondria in the mitochondrially-enriched cell. Each possibility represents a separate embodiment of the present invention.

The extent of enrichment of the stem cells with functional mitochondria may be determined by functional and/or enzymatic assays, including but not limited to rate of oxygen ($O_2$) consumption, content or activity level of citrate synthase, rate of adenosine triphosphate (ATP) production. In the alternative the enrichment of the stem cells with healthy donor mitochondria may be confirmed by the detection of mitochondrial DNA of the donor. According to some embodiments, the extent of enrichment of the stem cells with functional mitochondria may be determined by the level of change in heteroplasmy and/or by the copy number of mtDNA per cell. Each possibility represents a separate embodiment of the present invention.

TMRM (tetramethylrhodamine methyl ester) or the related TMRE (tetramethylrhodamine ethyl ester) are cell-permeant fluorogenic dyes commonly used to assess mitochondrial function in living cells, by identifying changes in mitochondrial membrane potential. According to some embodiments, the level of enrichment can be determined by staining with TMRE or TMRM.

According to another embodiment, the intactness of a mitochondrial membrane may be determined by any method known in the art. In a non-limiting example, intactness of a mitochondrial membrane is measured using the tetramethylrhodamine methyl ester (TMRM) or the tetramethylrhodamine ethyl ester (TMRE) fluorescent probes. Each possibility represents a separate embodiment of the present invention. Mitochondria that were observed under a microscope and show TMRM or TMRE staining have an intact mitochondrial outer membrane. As used herein, the term "a mitochondrial membrane" refers to a mitochondrial membrane selected from the group consisting of the mitochondrial inner membrane, the mitochondrial outer membrane, and both.

In certain embodiments, the level of mitochondrial enrichment in the mitochondrially-enriched human stem cells is determined by sequencing at least a statistically-representative portion of total mitochondrial DNA in the cells and determining the relative levels of host/endogenous mitochondrial DNA and exogenous mitochondrial DNA. In certain embodiments, the level of mitochondrial enrichment in the mitochondrially-enriched human stem cells is determined by single nucleotide polymorphism (SNP) analysis. In certain embodiments, the largest mitochondrial population and/or the largest mitochondrial DNA population is the host/endogenous mitochondrial population and/or the host/endogenous mitochondrial DNA population; and/or the second-largest mitochondrial population and/or the second-largest mitochondrial DNA population is the exogenous mitochondrial population and/or the exogenous mitochondrial DNA population. Each possibility represents a separate embodiment of the invention.

According to certain embodiments, the enrichment of the stem cells with healthy functional mitochondria may be determined by conventional assays that are recognized in the art. In certain embodiments, the level of mitochondrial enrichment in the mitochondrially-enriched human stem cells is determined by (i) the levels of host/endogenous mitochondrial DNA and exogenous mitochondrial DNA; (ii) the level of mitochondrial proteins selected from the group consisting of citrate synthase (CS), cytochrome C oxidase (COX1), succinate dehydrogenase complex flavoprotein subunit A (SDHA) and any combination thereof; (iii) the level of CS activity; or (iv) any combination of (i), (ii) and (iii). Each possibility represents a separate embodiment of the invention. In certain embodiments, the level of mitochondrial enrichment in the mitochondrially-enriched human stem cells is determined by at least one of: (i) the levels of host mitochondrial DNA and exogenous mitochondrial DNA in case of allogeneic mitochondria; (ii) the level of citrate synthase activity; (iii) the level of succinate dehydrogenase complex flavoprotein subunit A (SDHA) or cytochrome C oxidase (COX1); (iv) the rate of oxygen ($O_2$) consumption; (v) the rate of adenosine triphosphate (ATP) production or (vi) any combination thereof Each possibility represents a separate embodiment of the present invention. Methods for measuring these various parameters are well known in the art.

In certain embodiments, the pharmaceutical composition may further include non-enriched stem cells, megakaryocytes, erythrocytes, mast cells, myeloblasts, basophils, neutrophils, eosinophils, monocytes, macrophages, natural killer (NK) cells, small lymphocytes, T lymphocytes, B lymphocytes, plasma cells, reticular cells, or any combination thereof.

In some embodiments, there is provided a method for treating a renal disease, disorder or a symptom thereof in a human patient in need of such treatment, wherein the renal disease or disorder is not a primary mitochondrial disease or disorder caused by a pathogenic mutation in mitochondrial DNA or by a pathogenic mutation in nuclear DNA encoding a mitochondrial protein, the method comprising the step of administering a pharmaceutical composition comprising a plurality of mitochondrially enriched human stem cells to the patient, said stem cells are enriched with healthy functional human exogenous mitochondria.

In some embodiments, there is provided a method for treating a renal disease, disorder or a symptom thereof in a human patient in need of such treatment, the method comprising the step of administering a pharmaceutical composition comprising a plurality of human stem cells to the patient, wherein the human stem cells are enriched with healthy functional exogenous mitochondria without a pathogenic mutation in mitochondrial DNA, and wherein the renal disease or disorder is not a primary mitochondrial disease or disorder caused by a pathogenic mutation in mitochondrial DNA or with a pathogenic mutation in nuclear DNA.

The present invention further provides, in another aspect, a pharmaceutical composition comprising a plurality of human stem cells enriched with healthy functional human exogenous mitochondria, for use in a method of treating a renal disease, disorder or a symptom thereof, wherein the renal disease or disorder is not a primary mitochondrial disease or disorder caused by a pathogenic mutation in mitochondrial DNA or by a pathogenic mutation in nuclear DNA encoding for mitochondrial molecule.

In certain embodiments, the method comprises (a) thawing a frozen pharmaceutical composition comprising a therapeutically-effective amount of human stem cells enriched with healthy functional exogenous mitochondria, and (b) administering the thawed pharmaceutical composition to the patient.

In some embodiments, there is provided a pharmaceutical composition comprising a plurality of human stem cells enriched with healthy functional mitochondria without a pathogenic mutation in mitochondrial DNA, for use in a method of treating a renal disease, disorder or a symptom thereof, wherein the renal disease or disorder is not a primary mitochondrial disease or disorder caused by a pathogenic mutation in mitochondrial DNA or with a pathogenic mutation in nuclear DNA encoding a mitochondrial protein.

The present invention further provides, in another aspect, a pharmaceutical composition comprising a plurality of human stem cells enriched with healthy functional human mitochondria, for use in a method of treating a renal disease, disorder or a symptom thereof, wherein the renal disease or disorder is not a primary mitochondrial disease or disorder caused by a pathogenic mutation in mitochondrial DNA or by a pathogenic mutation in nuclear DNA encoding a mitochondrial molecule.

The present invention further provides, in another aspect, a pharmaceutical composition comprising a plurality of human stem cells enriched with healthy functional exogenous mitochondria without a pathogenic mutation in mitochondrial DNA, for use in a method of treating a renal disease, disorder or a symptom thereof, wherein the renal disease or disorder is not a primary mitochondrial disease or disorder caused by a pathogenic mutation in mitochondrial DNA or by a pathogenic mutation in nuclear DNA.

The present invention further provides, in another aspect, an ex-vivo method for enriching human stem cells with healthy functional human exogenous mitochondria, the method comprising the steps of: (i) providing a first composition, comprising a plurality of isolated or partially purified human stem cells from a patient afflicted with a renal disease or a renal disorder or a symptom thereof, wherein the renal disease or disorder is not a primary mitochondrial disease or disorder caused by a pathogenic mutation in mitochondrial DNA or with a pathogenic mutation in nuclear DNA encoding a mitochondrial molecule, or plurality of isolated or partially purified human stem cells from a healthy donor; (ii) providing a second composition, comprising a plurality of isolated healthy functional human exogenous mitochondria obtained from a donor without a pathogenic mutation in mitochondrial DNA or in a mitochondrial molecule (such as a protein); (iii) contacting the human stem cells of the first composition with the healthy functional human exogenous mitochondria of the second composition, thus providing a third composition; and (iv) incubating the third composition under conditions allowing the healthy functional human exogenous mitochondria to enter the human stem cells, thereby enriching said human stem cells with said healthy functional human exogenous mitochondria, thus providing a fourth composition comprising human stem cells enriched with healthy functional human exogenous mitochondria without a pathogenic mutation in mitochondrial DNA or in a mitochondrial molecule; wherein the enriched human stem cells of step (iv) have a detectably higher total content of healthy functional human mitochondria compared to the human stem cells in step (i).

The term "ex-vivo method" as used herein refers to a method comprising steps performed exclusively outside the human body. In particular, an ex vivo method comprises manipulation of cells outside the body that are subsequently reintroduced or transplanted into the subject to be treated.

The term "healthy donor" and "healthy subject" are used interchangeably, and refer to a subject not suffering from the disease or condition which is being treated.

The term "contacting" refers to bringing the composition of mitochondria and cells into sufficient proximity to promote entry of the mitochondria into the cells. The term "introducing" mitochondria into the stem cells is used interchangeably with the term contacting.

The term "isolated human healthy functional mitochondria" as used herein refers to intact mitochondria isolated, obtained or derived from cells obtained from a healthy subject, not afflicted with a mitochondrial disease. In some embodiments, such mitochondria are exogenous mitochondria. The term "isolated" as used herein and in the claims in the context of mitochondria includes mitochondria that were purified, at least partially, from other components found in said source. In certain embodiments, the total amount of mitochondrial proteins in the second composition comprising the plurality of isolated healthy functional exogenous mitochondria, is between 20%-80%, 20-70%, 40-70%, 20-40%, or 20-30% of the total amount of cellular proteins within the sample. Each possibility represents a separate embodiment of the present invention. In certain embodiments, the total amount of mitochondrial proteins in the second composition comprising the plurality of isolated healthy functional exogenous mitochondria, is between 20%-80% of the total amount of cellular proteins within the sample. In certain embodiments, the total amount of mitochondrial proteins in the second composition comprising the plurality of isolated healthy functional exogenous mitochondria, is between 20%-80% of the combined weight of the mitochondria and other sub-cellular fractions. In other embodiments, the total amount of mitochondrial proteins in the second composition comprising the plurality of isolated healthy functional exogenous mitochondria, is above 80% of the combined weight of the mitochondria and other sub-cellular fractions.

In some embodiments, the methods described above in various embodiments thereof further comprises expanding the stem cells of the first composition by culturing said stem cells in a proliferation medium capable of expanding stem cells. In other embodiments, the method further comprises expanding the mitochondrially-enriched stem cells of the fourth composition by culturing said cells in a culture or proliferation medium capable of expanding stem cells. As used throughout this application, the term "culture or proliferation medium" is a fluid medium such as cell culture media, cell growth media, buffer which provides sustenance to the cells. As used throughout this application, and in the claims the term "pharmaceutical composition" comprises a fluid carrier such as cell culture media, cell growth media, buffer which provides sustenance to the cells.

In additional embodiments, the human stem cells are expanded before or after mitochondrial augmentation.

According to some embodiments, the method for enriching human stem cells with healthy functional exogenous mitochondria does not comprise measuring the membrane potential of the cell.

In some embodiments, the enrichment of the stem cells with healthy functional exogenous mitochondria comprises introducing into the stem cells a dose of mitochondria of at least 0.044 up to 176 milliunits of CS activity per million cells. In some embodiments, the enrichment of the stem cells with healthy functional exogenous mitochondria comprises introducing into the stem cells a dose of mitochondria of at least 0.088 up to 176 milliunits of CS activity per million cells. In other embodiments, the enrichment of the stem cells with healthy functional exogenous mitochondria comprises introducing into the stem cells a dose of mitochondria of at least 0.2 up to 150 milliunits of CS activity per million cells. In other embodiments, the enrichment of the stem cells with healthy functional exogenous mitochondria comprises introducing into the stem cells a dose of mitochondria of at least 0.4 up to 100 milliunits of CS activity per million cells. In some embodiments, the enrichment of the stem cells with healthy functional exogenous mitochondria comprises introducing into the stem cells a dose of mitochondria of at least 0.6 up to 80 milliunits of CS activity per million cells. In some embodiments, the enrichment of the stem cells with healthy functional exogenous mitochondria comprises introducing into the stem cells a dose of mitochondria of at least 0.7 up to 50 milliunits of CS activity per million cells. In some embodiments, the enrichment of the stem cells with healthy functional exogenous mitochondria comprises introducing into the stem cells a dose of mitochondria of at least 0.8 up to 20 milliunits of CS activity per million cells. In some embodiments, the enrichment of the stem cells with healthy functional exogenous mitochondria comprises introducing into the stem cells a dose of mitochondria of at least 0.88 up to 17.6 milliunits of CS activity per million cells. In some embodiments, the enrichment of the stem cells with healthy functional exogenous mitochondria comprises introducing into the stem cells a dose of mitochondria of at least 0.44 up to 17.6 milliunits of CS activity per million cells.

Mitochondrial dose can be expressed in terms of units of CS activity or mtDNA copy number of other quantifiable measurements of the amount of healthy functional mitochondria as explained herein. A "unit of CS activity" is defined as the amount that enables conversion of one micromole substrate in 1 minute in 1 mL reaction volume.

The present invention further provides, in another aspect, a plurality of human stem cells enriched with healthy functional human exogenous mitochondria, obtained by the method described above.

The present invention further provides, in another aspect, a pharmaceutical composition comprising a therapeutically-effective amount of a plurality of human stem cells enriched with healthy functional human exogenous mitochondria, as described above.

In certain embodiments, the pharmaceutical composition described above is for use in a method for treating a renal disease or a renal disorder or a symptom thereof, wherein the renal disease or disorder is not a primary mitochondrial disease or disorder caused by a pathogenic mutation in mitochondrial DNA or with a pathogenic mutation in nuclear DNA.

The present invention further provides, in another aspect, a method for treating a renal disease or a renal disorder or a symptom thereof in a patient in need thereof, comprising administering to the patient the pharmaceutical composition described above, wherein the renal disease or disorder is not a primary mitochondrial disease or disorder caused by a pathogenic mutation in mitochondrial DNA or with a pathogenic mutation in nuclear DNA.

In certain embodiments, the first composition is fresh. In certain embodiments, the first composition was frozen and then thawed prior to incubation. In certain embodiments, the second composition is fresh. In certain embodiments, the second composition was frozen and then thawed prior to incubation. In certain embodiments, the fourth composition is fresh. In certain embodiments, the fourth composition was frozen and then thawed prior to administration.

In certain embodiments, the total amount of mitochondrial proteins in the second composition comprising the plurality of isolated healthy functional exogenous mitochondria, is between 20%-80% of the total amount of cellular proteins within the sample. In certain embodiments, the total amount of mitochondrial proteins in the second composition comprising the plurality of isolated healthy functional exogenous mitochondria, is between 20%-70%, 20%-60% or 30%-50% of the total amount of cellular proteins within the sample. Each possibility represents a separate embodiment of the present invention. In certain embodiments, the total amount of mitochondrial proteins in the second composition comprising the plurality of isolated healthy functional exogenous mitochondria, is between 20%-80% of the combined weight of the mitochondria and other sub-cellular fractions. In other embodiments, the total amount of mitochondrial proteins in the second composition comprising the plurality of isolated healthy functional exogenous mitochondria, is above 80% of the combined weight of the mitochondria and other sub-cellular fractions.

Eukaroytic NADPH-cytochrome C reductase (cytochrome C reductase) is a flavoprotein localized to the endoplasmic reticulum. It transfers electrons from NADPH to several oxygenases, the most important of which are the cytochrome P450 family of enzymes, responsible for xenobiotic detoxification. Cytochrome C reductase is widely used as an endoplasmic reticulum marker. In certain embodiments, the second composition is substantially free from cytochrome C reductase or cytochrome C reductase activity. In certain embodiments, the fourth composition is not enriched with cytochrome C reductase or cytochrome C reductase activity compared to the first composition.

In some embodiments, the stem cells in the fourth composition have at least one of (i) an increased mitochondrial DNA content; (ii) an increased content of at least one mitochondrial protein selected from the group consisting of CS, COX1 and SDHA; (iii) an increased rate of oxygen ($O_2$) consumption; (ii) an increased activity level of citrate synthase; (iii) an increased rate of adenosine triphosphate (ATP) production; or (iv) any combination thereof, relative to the stem cells in the first composition. Each possibility represents a separate embodiment of the invention.

The term "increased mitochondrial DNA content" as used herein refers to the content of mitochondrial DNA which is detectably higher than the mitochondrial DNA content in the first composition, prior to mitochondria enrichment. Mitochondrial DNA content may be measured by performing quantitative PCR of a mitochondrial gene prior and post mitochondrial enrichment, normalized to a nuclear gene.

The term "increased content of at least one mitochondrial protein" as used herein refers to the content of either nuclear-encoded or mitochondrial-encoded mitochondrial proteins, e.g., CS, COX1 and SDHA, which is detectably higher than content of said mitochondrial protein in the first composition, prior to mitochondrial enrichment.

The term "increased rate of oxygen (O2) consumption" as used herein refers to a rate of oxygen (O2) consumption which is detectably higher than the rate of oxygen (O2) consumption in the first composition, prior to mitochondrial enrichment.

The term "increased content or activity level of citrate synthase" as used herein refers to a content or activity level of citrate synthase which is detectably higher than the content value or activity level of citrate synthase in the first composition, prior to mitochondrial enrichment.

The term "increased rate of adenosine triphosphate (ATP) production" as used herein refers to a rate of adenosine triphosphate (ATP) production which is detectably higher than the rate of adenosine triphosphate (ATP) production in the first composition, prior to mitochondrial enrichment.

In certain embodiments, the term "detectably higher" as used herein refers to a statistically-significant increase between the normal and increased values. In certain embodiments, the term "detectably higher" as used herein refers to a non-pathological increase, i.e. to a level in which no pathological symptom associated with the substantially higher value becomes apparent. In certain embodiments, the term "increased" as used herein refers to a value which is 1.05 fold, 1.1 fold, 1.25 fold, 1.5 fold, 2 fold, 3 fold, 4 fold, 5 fold, 6 fold, 7 fold or higher than the corresponding value found in corresponding cells or corresponding mitochondria of a plurality of healthy subjects or in the stem cells of the first composition prior to mitochondrial enrichment. Each possibility represents a separate embodiment of the invention.

In specific situations the same cells, prior to mitochondrial enrichment, serve as controls to measure CS and ATP activity and determine enrichment level.

The phrase "conditions allowing the human functional exogenous mitochondria to enter the human stem cells" as used herein generally refers to parameters such as time, temperature, and proximity between the exogenous mitochondria and the human stem cells. While identifying those conditions are within the capabilities of any man of ordinary skill in the field, such conditions are provided by the present invention. For example, human cells and human cell lines are routinely incubated with mitochondria in liquid medium, in a sterile environment, at 37° C. and 5% $CO_2$ atmosphere. In certain embodiments, the stem cells were incubated with the mitochondria for 24 hours at R.T. in saline containing 4.5% HSA (human serum albumin).

In certain embodiments, the human stem cells are incubated with the healthy functional exogenous mitochondria for a time ranging from 0.5 to 30 hours, at a temperature ranging from 16 to 37° C. In certain embodiments, the human stem cells are incubated with the healthy functional exogenous mitochondria for a time ranging from 1 to 30 or from 5 to 25 hours. Each possibility represents a separate embodiment of the present invention. In specific embodiments, incubation is for 20 to 30 hours. In some embodiments, incubation is at room temperature (18° C. to 30° C.) for at least 1, 5, 10, 15 or 20 hours. Each possibility represents a separate embodiment of the present invention. In other embodiments, incubation is up to 1, 5, 10, 15, 20 or 30 hours. Each possibility represents a separate embodiment of the present invention. In specific embodiments, incubation is for 24 hours. In some embodiments, incubation is at room temperature (20° C. to 30° C.). In certain embodiments, incubation is at 37° C. In some embodiments, incubation is in a 5% $CO_2$ atmosphere for at least 1, 5, 10, 15 or 20 hours, and/or up to 1, 5, 10, 15 or 20 hours. In other embodiments, incubation does not include added $CO_2$ above the level found in air. In some embodiments, incubation is in a medium supporting cell survival. In some embodiments, the medium is Dulbecco's Modified Eagle Medium (DMEM). In other embodiment, the medium is saline containing HSA (human serum albumin). In some embodiments, the saline contains between 2% to 10% HSA. In further embodiments, the saline contains between 3 to 6% HSA. In yet further embodiments, the saline contains 4.5% HSA. In specific embodiments, incubation of the stem cells with the heathy functional mitochondria is at a temperature ranging between 16 to 30° C., for a time ranging between 15 to 30 hours, in a saline containing between 3 to 6% HSA, without added $CO_2$ above the level found in air.

In certain embodiments, the methods described above in various embodiments thereof, further include centrifugation before, during or after incubation of the stem cells with the exogenous mitochondria. Each possibility represents a separate embodiment of the present invention. In some embodiments, the methods described above in various embodiments thereof, include a single centrifugation step before, during or after incubation of the stem cells with the exogenous mitochondria. In some embodiments, the centrifugation force ranges from 1000 g to 8500 g. In some embodiments, the centrifugation force ranges from 2000 g to 4000 g. In some embodiments, the centrifugation force is above 2500 g. In some embodiments, the centrifugation force ranges from 2500 g to 8500 g. In some embodiments, the centrifugation force ranges from 2500 g to 8000 g. In some embodiments, the centrifugation force ranges from 3000 g to 8000 g. In other embodiments, the centrifugation force ranges from 4000 g to 8000 g. In specific embodiments, the centrifugation force is 7000 g. In other embodiments, the centrifugation force is 8000 g. In some embodiments, centrifugation is performed for a time ranging from 2 minutes to 30 minutes. In some embodiments, centrifugation is performed for a time ranging from 3 minutes to 25 minutes. In some embodiments, centrifugation is performed for a time ranging from 5 minutes to 20 minutes. In some embodiments, centrifugation is performed for a time ranging from 8 minutes to 15 minutes.

In some embodiments, centrifugation is performed in a temperature ranging from 4 to 37° C. In certain embodiments, centrifugation is performed in a temperature ranging from 4 to 10° C. or 16-30° C. Each possibility represents a separate embodiment of the present invention. In specific embodiments, centrifugation is performed at 2-6° C. In specific embodiments, centrifugation is performed at 4° C. In some embodiments, the methods described above in various embodiments thereof include a single centrifugation before, during or after incubation of the stem cells with the exogenous mitochondria, followed by resting the cells at a temperature lower than 30° C. In some embodiments, the conditions allowing the human functional mitochondria to enter the human stem cells include a single centrifugation before, during or after incubation of the stem cells with the exogenous mitochondria, followed by resting the cells at a temperature ranging between 16 to 28° C.

By manipulating the conditions of the incubation, one can manipulate the features of the product. In certain embodiments, the incubation is performed at 37° C. In certain embodiments, the incubation is performed for at least 6 hours. In certain embodiments, the incubation is performed for at least 12 hours. In certain embodiments, the incubation is performed for 12 to 24 hours. In certain embodiments, the incubation is performed at a ratio of $1*10^5$ to $1*10^7$ naïve stem cells per amount of exogenous mitochondria having or exhibiting 4.4 milliunits of CS. In certain embodiments, the incubation is performed at a ratio of $1*10^6$ naïve stem cells per amount of exogenous mitochondria having or exhibiting 4.4 milliunits of CS. In certain embodiments, the conditions are sufficient to increase the mitochondrial content of the naïve stem cells by about 5% to about 100% as determined by CS activity. In certain embodiments, the conditions are sufficient to increase the mitochondrial content of the naïve stem cells by at least about 5% as determined by CS activity.

Heteroplasmy is the presence of more than one type of mitochondrial DNA within a cell or individual. The heteroplasmy level is the proportion of mutant mtDNA molecules vs. wild type/functional mtDNA molecules and is an important factor in considering the severity of mitochondrial diseases. While lower levels of heteroplasmy (sufficient amount of mitochondria are functional) are associated with a healthy phenotype, higher levels of heteroplasmy (insufficient amount of mitochondria are functional) are associated with pathologies. In certain embodiments, the heteroplasmy level of the stem cells in the fourth composition is at least 1% lower than the heteroplasmy level of the stem cells in the first composition. In certain embodiments, the heteroplasmy level of the stem cells in the fourth composition is at least 3% lower than the heteroplasmy level of the stem cells in the first composition. In certain embodiments, the heteroplasmy level of the stem cells in the fourth composition is at least 5% lower than the heteroplasmy level of the stem cells in the first composition. In certain embodiments, the heteroplasmy level of the stem cells in the fourth composition is at least 10% lower than the heteroplasmy level of the stem cells in the first composition. In certain embodiments, the heteroplasmy level of the stem cells in the fourth composition is at least 15% lower than the heteroplasmy level of the stem cells in the first composition. In certain embodiments, the heteroplasmy level of the stem cells in the fourth composition is at least 20% lower than the heteroplasmy level of the stem cells in the first composition. In certain embodiments, the heteroplasmy level of the stem cells in the fourth composition is at least 25% lower than the heteroplasmy level of the stem cells in the first composition. In certain embodiments, the heteroplasmy level of the stem cells in the fourth composition is at least 30% lower than the heteroplasmy level of the stem cells in the first composition.

The term "mitochondrial content" as used herein refers to the amount of mitochondria within a cell. The term "mitochondrial content" as used herein further refers to the amount of functional mitochondria within a cell, or to the average amount of functional mitochondria within a plurality of cells.

The term "enriched human stem cells" refers to human stem cells, and to populations of human stem cells, which their mitochondrial content was increased, on average, by an active step of a method, compared to their naïve counterparts. The term "increased mitochondrial content" as used herein further refers to a mitochondrial content of the cells in after incubation with mitochondria which is detectably higher than the mitochondrial content of the cells prior to mitochondria enrichment.

The phrase stem cells "obtained" from s subject/patient as used herein refers to cells that were stem cells in the subject/patient at the time of their isolation from said subject/patient.

The phrase stem cells "derived" from a subject/patient as used herein refers to cells that were not stem cells in the patient, and have been manipulated to become stem cells. The phrase further includes stems cells of a certain type which have been manipulated to become stem cells of a different type. The term "manipulated" as used herein refers to the use of any one of the methods known in the field (Yu J. et al., Science, 2007, Vol. 318 (5858), pages 1917-1920) for reprograming somatic cells to an undifferentiated state and becoming induced pluripotent stem cells (iPSc), and, optionally, further reprograming the iPSc to become cells of a desired lineage or population (Chen M. et al., IOVS, 2010, Vol. 51 (11), pages 5970-5978), such as bone-marrow cells (Xu Y. et al., 2012, PLOS ONE, Vol. 7 (4), page e34321).

The term "peripheral blood" as used herein refers to blood circulating in the blood system. The term "isolating from the peripheral blood" as used herein refers to the isolation of the stem cells from the other constituents found in the blood.

Citrate synthase (CS) is localized in the mitochondrial matrix, but is encoded by nuclear DNA. Citrate synthase is involved in the first step of the Krebs cycle, and is commonly used as a quantitative enzyme marker for the presence of intact mitochondria (Larsen S. et al., 2012, J. Physiol., Vol. 590 (14), pages 3349-3360; Cook G. A. et al., Biochim. Biophys. Acta., 1983, Vol. 763 (4), pages 356-367). In certain embodiments, the mitochondrial content of the stem cells in the first composition or in the fourth composition is determined by determining the content of citrate synthase. In certain embodiments, the mitochondrial content of the stem cells in the first composition or in the fourth composition is determined by determining the activity level of citrate synthase. In certain embodiments, the mitochondrial content of the stem cells in the first composition or in the fourth composition correlates with the content of citrate synthase. In certain embodiments, the mitochondrial content of the stem cells in the first composition or in the fourth composition correlates with the activity level of citrate synthase. CS activity can be measured by commercially available kits, e.g., using the CS activity kit CS0720 (Sigma).

Mitochondrial DNA content may be measured by performing quantitative PCR of a mitochondrial gene prior and post mitochondrial enrichment, normalized to a nuclear gene.

In certain embodiments, the donor of the HLA-matched stem cells is the patient. In certain embodiments, the donor of the HLA-matched stem cells is a family relative of the patient. The term "HLA-matched" as used herein refers to the desire that the patient and the donor of the stem cells be as closely HLA-matched as possible, at least to the degree in which the patient does not develop an acute immune response against the stem cells of the donor. The prevention and/or therapy of such an immune response may be achieved with or without acute or chronic use of immune-suppressors. In certain embodiments, the stem cells from the donor are HLA-matched to the patient to a degree wherein the patient does not reject the stem cells. In certain embodiment, the patient is further treated by an immunosuppressive therapy to prevent immune rejection of the stem cells graft.

As used herein, the term "autologous cells" or "cells that are autologous, refers to being the patient's own cells. The term "autologous mitochondria", refers to mitochondria obtained from the patient's own cells or from maternally related cells. The terms "allogeneic cells" or "allogeneic mitochondria", refer to cells or mitochondria being from a different donor individual.

The term "syngeneic" as used herein and in the claims refers to genetic identity or genetic near-identity sufficient to allow grafting among individuals without rejection. The term syngeneic in the context of mitochondria is used herein interchangeably with the term autologous mitochondria meaning of the same maternal bloodline.

The term "exogenous mitochondria" refers to a mitochondria that are introduced to a target cell (i.e., stem cell), from a source which is external to the cell. For example, in some embodiments, an exogenous mitochondria may be derived or isolated from a cell which is different than the target cell. For example, an exogenous mitochondria may be produced/made in a donor cell, purified/isolated obtained from the donor cell and thereafter introduced into the target cell.

The term "endogenous mitochondria" refers to mitochondria that are being made/expressed/produced by cell and is not introduced from an external source into the cell. In some embodiments, endogenous mitochondria contain proteins and/or other molecules which are encoded by the genome of the cell. In some embodiments, the term "endogenous mitochondria" is equivalent to the term "host mitochondria".

In some embodiments, the identification/discrimination of endogenous mitochondria from exogenous mitochondria, after the latter have been introduced into the target cell, can be performed by various means, including, for example, but not limited to: identifying differences in mitochondrial DNA (mtDNA) sequences, for example different haplotypes, between the endogenous mitochondria and exogenous mitochondria, identify specific mitochondrial proteins originating from the tissue of the exogenous mitochondria, such as, for example, cytochrome p450 Cholesterol side chain cleavage (P450SCC) from placenta, UCP1 from brown adipose tissue, and the like, or any combination thereof.

In certain embodiments, the method described above further comprises a step of administering to the patient an agent which promotes mitochondrial biogenesis. The term "mitochondrial biogenesis" as used herein refers to the growth and division of mitochondria. In certain embodiments, the agent which promotes mitochondrial biogenesis is erythropoietin (EPO) or a salt thereof. In certain embodiments, the agent is selected from the group consisting of recombinant human erythropoietin and isolated human erythropoietin.

The term "pre-transplant conditioning agent" as used herein refers to any agent capable of killing bone-marrow cells within the bone-marrow of a human subject.

As used herein, the term "flash-freezing" refers to rapidly freezing the mitochondria by subjecting them to cryogenic temperatures.

The term "about" as used herein means a range of 10% below to 10% above the indicated integer, number or amount. For example, the phrase "about $1*10^5$" means "$1.1*10^5$ to $9*10^4$". Typically, the numerical values as used herein refer to ±10% of the indicated numerical value.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The following examples are presented in order to more fully illustrate some embodiments of the invention. They should, in no way be construed, however, as limiting the broad scope of the invention.

EXAMPLES

Example 1. Mitochondria Augmentation Therapy in Murine Cells.

Different murine cells were incubated in DMEM (24 hours, 37° C., 5% $CO_2$) with isolated murine or human mitochondria in order to increase their mitochondrial content and activity. Table 1 describes representative results of the mitochondria augmentation therapy process, determined by the relative increase in CS activity of the cells after the process compared to the CS activity of the cells before the process.

Table 1.

| Origin of cells | Origin of mitochondria | CS activity of mitochondria/ number of cells | Relative increase in CS activity of cells |
|---|---|---|---|
| ICR Mouse- Isolated from whole bone marrow | Human mitochondria | 4.4 mU CS/1 × 10^6 Cells | +41% |
| FVB/N Mouse- Isolated from whole bone marrow | C57/BL placental mitochondria | 4.4 mU CS/1 × 10^6 Cells | +70% |

| Origin of cells | Origin of mitochondria | CS activity of mitochondria/ number of cells | Relative increase in CS activity of cells |
|---|---|---|---|
| FVB/N Mouse-Isolated from whole bone marrow | C57/BL liver mitochondria | 4.4 mU CS/1 × 10^6 Cells | +25% |
| Human-CD34+-Isolated by pheresis-Frozen | Human blood mitochondria | 4.4 mU CS/1 × 10^6 Cells | +33% |

Example 2. Pre-Clinical Bio-Distribution Studies.

Mitochondria were isolated from placenta of C57/BL mice (donor of wild type mtDNA). Bone marrow cells were isolated from FVB/N mice (carry an mtDNA mutation in ATP8). FVB/N cells were loaded with C57/BL exogenous mitochondria (4.4 mU of mitochondria per $1 \times 10^6$ cells), and then I.V. injected back to FVB/N mice. FVB/N mice were then sacrificed in different time points, and organ bio-distribution was tested.

FIG. 1 presents the level of FVB/N mtDNA found in the bone marrow as a function of time post the I.V. injection. The data teach that the level of mutated mtDNA in the bone marrow was significantly reduced over time.

Example 3. Mitochondrial Augmentation Therapy Improves Kidney Function in Mice.

Mitochondria were isolated from term C57BL murine placenta. Bone marrow cells of 12 months old C57BL mice were obtained. Bone marrow cells enriched with mitochondria (MNV-BM-PLC, $1 \times 10^6$ cells), bone marrow cells alone (BM, $1 \times 10^6$ cells) or a control vehicle solution (VEHICLE, 4.5% Albumin in 0.9% w/v NaCl) were injected IV to the tail vein of 12 months old C57BL mice at the beginning of the experiment and again at about the age of 15 months, 18 months, 21 months. BUN blood test was performed 1, 3, 4 and 6 months post first IV injection.

Figure 2:
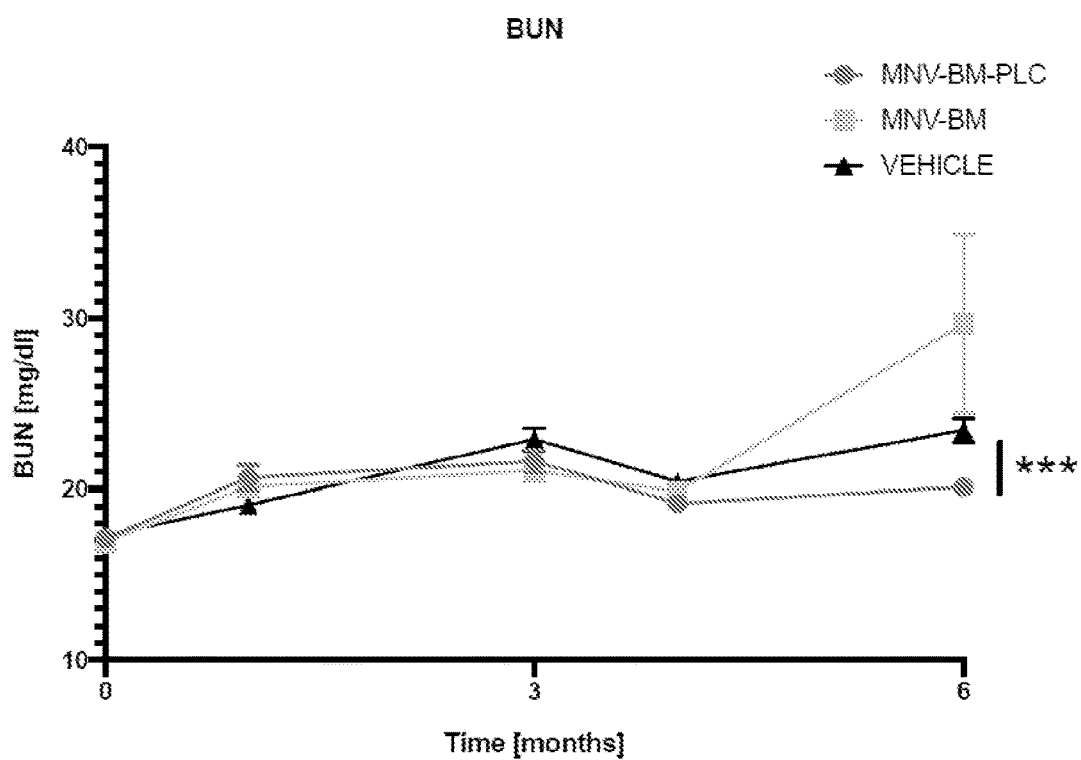
FIG. 2 is a line graph illustrating blood urea nitrogen (BUN) levels of aging mice (12 months old) treated with bone marrow cells enriched with placental mitochondria every approximately 3 as a function of time post administration of the enriched bone marrow cells (MNV-BM-PLC), untreated bone marrow cells (MNV-BM) and control (VEHICLE).

As can be seen in FIG. 2, aging mice (12 months) transplanted with bone marrow cells enriched with healthy mitochondria (MNV-BM-PLC) arrested kidney deterioration, illustrated by the decreased level of blood urea nitrogen 6 months following MAT.

Example 4. Compassionate Treatment Using Autologous CD34+ Cells Enriched with MNV-BLD (Blood Derived Mitochondria) for a Young Patient with Pearson Syndrome (PS) and PS-Related Renal Fanconi's Syndrome (FS).

Patient 1 was a 6.5-years old male patient diagnosed with Pearson Syndrome, having a deletion of nucleotides 5835-9753 in his mtDNA. Prior to mitochondrial augmentation therapy (MAT), his weight was 14.5 KG. His growth was significantly delayed for 3 years prior to treatment with no improvement despite being fed by a gastrostomy tube (G-tube) for more than a year. The patient had renal failure (GFR 22 ml/min), proximal tubulopathy requiring electrolyte supplementation and hypoparathyroidism requiring calcium supplementation.

Mobilization of hematopoietic stem and progenitor cells (HSPC) from the patient was performed by subcutaneous administration of GCSF, given alone for 5 days. Leukapheresis was performed using a Spectra Optia system (TerumoBCT), via peripheral vein access, according to institutional guidelines. CD34 positive selection was performed on mobilized peripheral blood derived cells by using the CliniMACS CD34 reagent according to the manufacturer's instructions. Mitochondria were isolated from maternal peripheral blood mononuclear cells (PBMCs) using 250 mM sucrose buffer pH 7.4 by differential centrifugation.

For MAT, the autologous CD34+ cells were incubated with the healthy mitochondria from the patient's mother ($1*10^6$ cells per amount of mitochondria having 4.4 milli-units of citrate synthase (CS)), which resulted in a 1.56 fold increase in the cells mitochondrial content (56% increase in mitochondrial content as demonstrated by CS activity). Incubation with mitochondria was performed for 24 hours at R.T. in saline containing 4.5% HSA. Enriched cells were suspended in 4.5% HSA in saline solution.

Figure 3A:
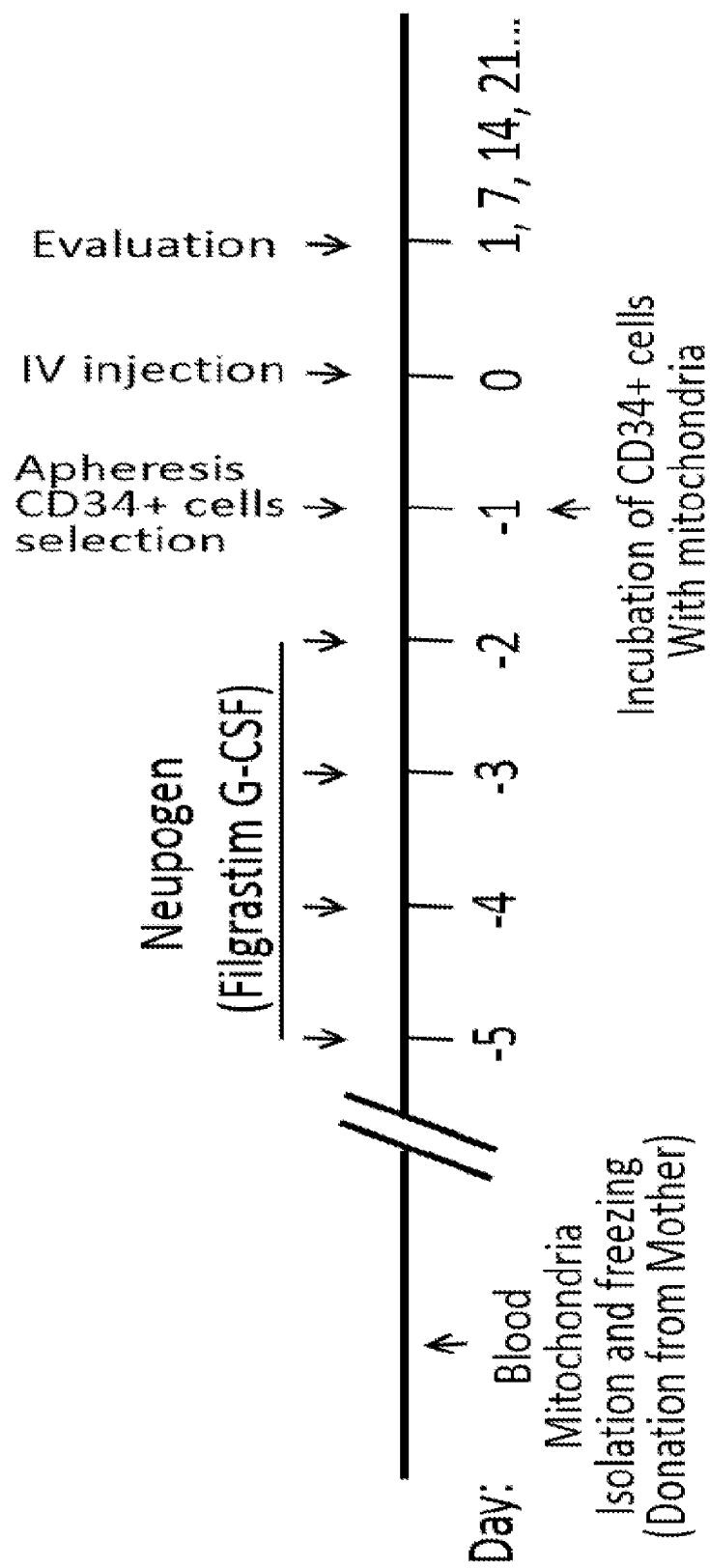
FIG. 3A is a scheme of the different stages of treatment of a Pearson Syndrome (PS) patient, as provided by the present invention.

The patient received a single round of treatment, by IV infusion, of $1.1*10^6$ autologous CD34+ cells enriched with healthy mitochondria per kilogram body weight, according to the timeline presented in FIG. 3A.

Table 2 presents the Pediatric Mitochondrial Disease Scale (IPMDS)-Quality of Life (QoL) Questionnaire results of the patient as a function of time post cellular therapy. In both the "Complaints & Symptoms" and the "Physical Examination" categories, 0 represents "normal" to the relevant attribute, while aggravated conditions are scored as 1-5, dependent on severity.

TABLE 2

|  | Pre-treatment | +6 months |
|---|---|---|
| Complaints & Symptoms | 24 | 11 |
| Physical Examination | 13.4 | 4.6 |

Figure 3B:
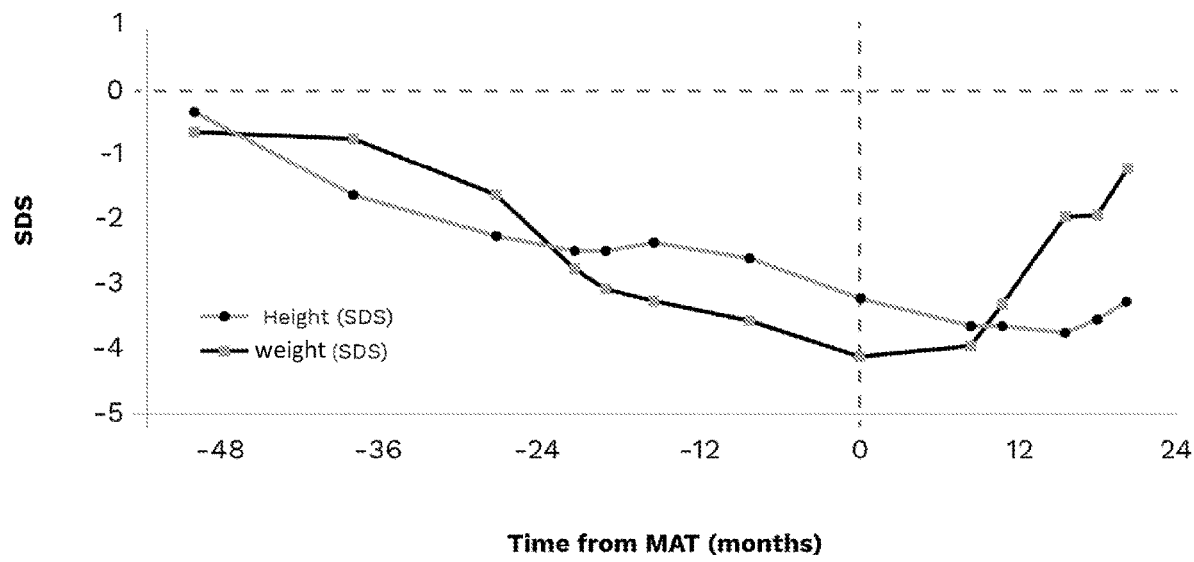
FIG. 3B is a line graph illustrating the standard deviation score of the weight and height of a PS patient treated by the methods provided in the present invention as a function of time before and after therapy

It should be noted that the patient has not gained weight in the 3 years before treatment, i.e. did not gain any weight since being 3.5 years old. FIG. 3B shows the growth measured by standard deviation score of the weight and height of the patient, with data starting 4 years prior to MAT and during the follow-up period. The data indicates that approximately 9 months or 15 months following a single treatment, there was an increase in the weight and height of the patient, respectively.

Figure 3C:
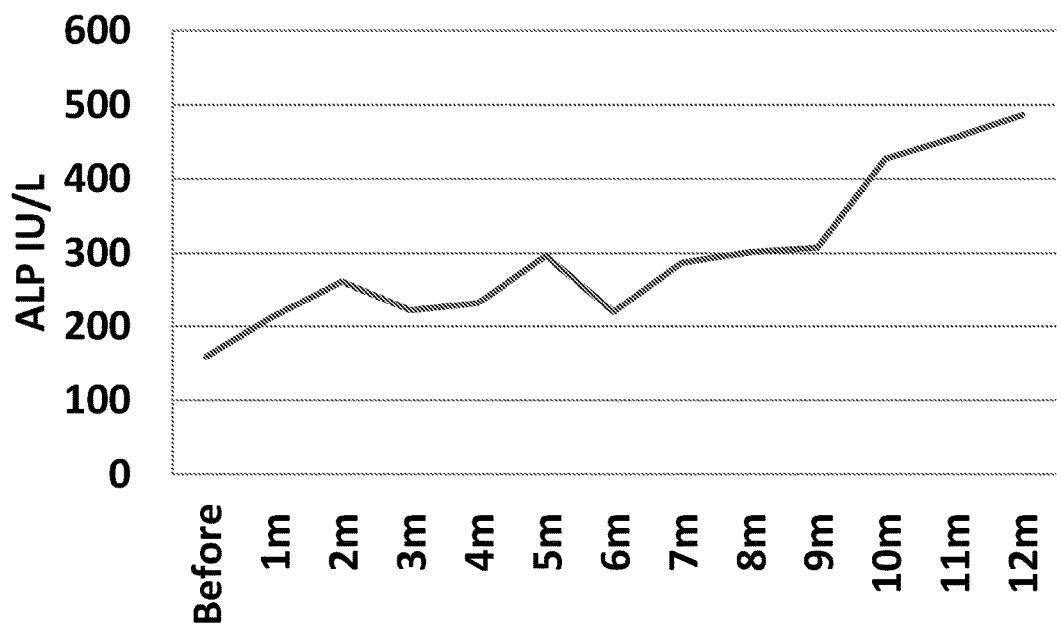
FIG. 3C is a line graph illustrating the alkaline phosphatase (ATP) level of a PS patient treated by the methods provided in the present invention as a function of time before and after therapy.

Another evidence for the patient's growth comes from his Alkaline Phosphatase levels. An alkaline phosphatase level test (ALP test) measures the amount of alkaline phosphatase enzyme in the bloodstream. Having lower than normal ALP levels in the blood can indicate malnutrition, which could be caused by a deficiency in certain vitamins and minerals. The data presented in FIG. 3C indicates that a single treatment was sufficient to elevate the Alkaline Phosphatase levels of the patient from 159 to 486 IU/L in only 12 months.

Figure 3D:
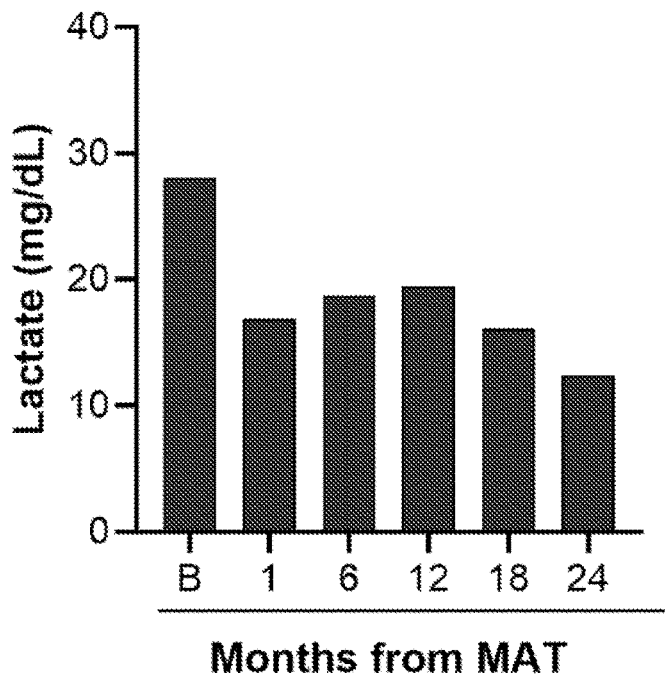
FIG. 3D is a bar graph illustrating the level of lactate in the blood of a PS patient treated by the methods provided in the present invention as a function of time before and after therapy.
Figure 3E:
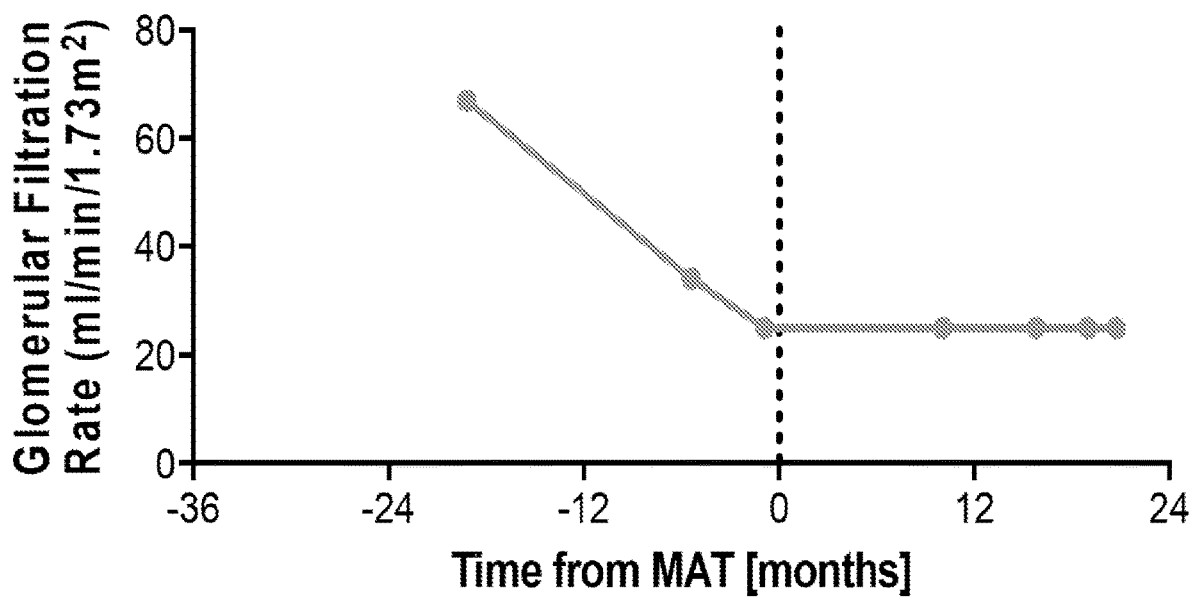
FIG. 3E is a line graph illustrating the glomerular filtration rate (GFR) level of a PS patient treated by the methods provided in the present invention as a function of time before and after therapy.

Blood lactate is lactic acid that appears in the blood as a result of anaerobic metabolism when mitochondria are damaged or when oxygen delivery to the tissues is insufficient to support normal metabolic demands, one of the hallmarks of mitochondria dysfunction. FIG. 3D presents the level of lactate found in the blood of the patient as a function of time post the I.V. injection. As can be seen in FIG. 3D after MAT, blood lactate level of patient 1 has decreased to normal values.

Figure 3F:
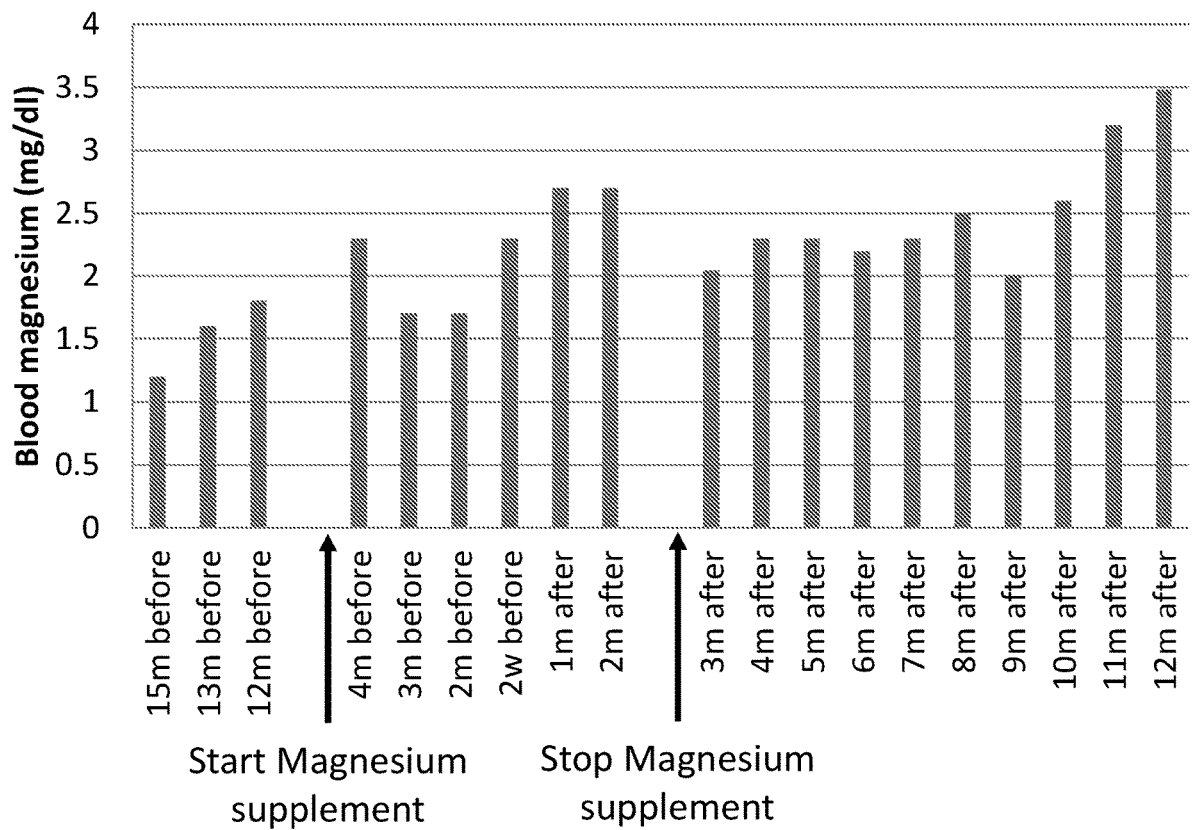
FIG. 3F is a bar graph illustrating the levels of blood magnesium in a PS patient treated by the methods provided in the present invention as a function of time before and after therapy, before and after magnesium supplementation
Figure 3G:
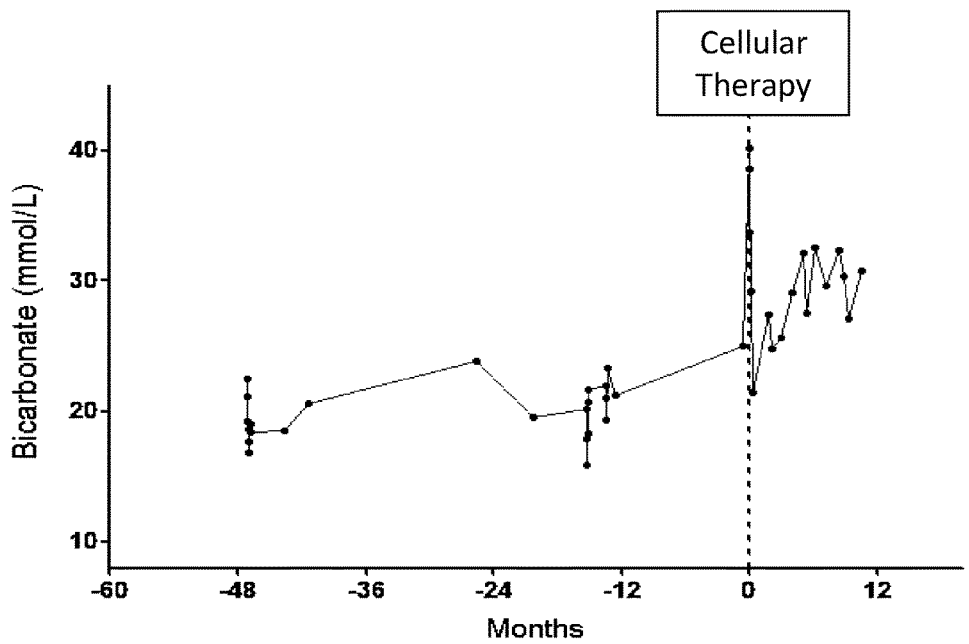
FIG. 3G is a line graph illustrating the blood bicarbonate level of a PS patient treated by the methods provided in the present invention as a function of time before and after therapy.

Prior to MAT, renal impairment of both glomerular and tubular functions were noted in patient 1. Following MAT, both functions were improved, with stabilization of glomerular filtration rate (FIG. 2E-), improvement in serum magnesium levels (FIG. 3F) and bicarbonate levels (FIG. 3G), Attaining high levels of magnesium, without magnesium supplementation, is evidence of improved magnesium absorption as well as re-absorption in the kidney proximal tubule.

Figure 3H:
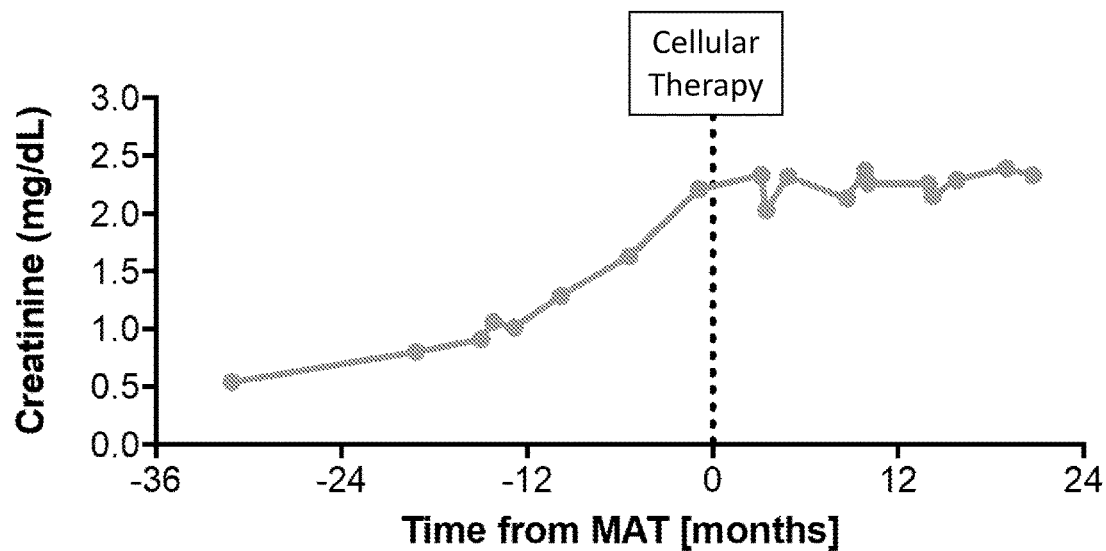
FIG. 3H is a line graph illustrating the creatinine level of a PS patient treated by the methods provided in the present invention as a function of time before and after therapy.

FIG. 3H presents the level of creatinine in the blood of the patient as a function of time pre and post cellular therapy. The data teach that the creatinine level of the patient was initially normal (below 1 mg/dL) but over time, about 12 month before the treatment, his condition deteriorated. Reaching high levels of creatinine is a marker of kidney failure. After initializing cellular therapy, his condition stabilized and further deterioration (illustrated by the dotted line) was prevented.

Figure 3I:
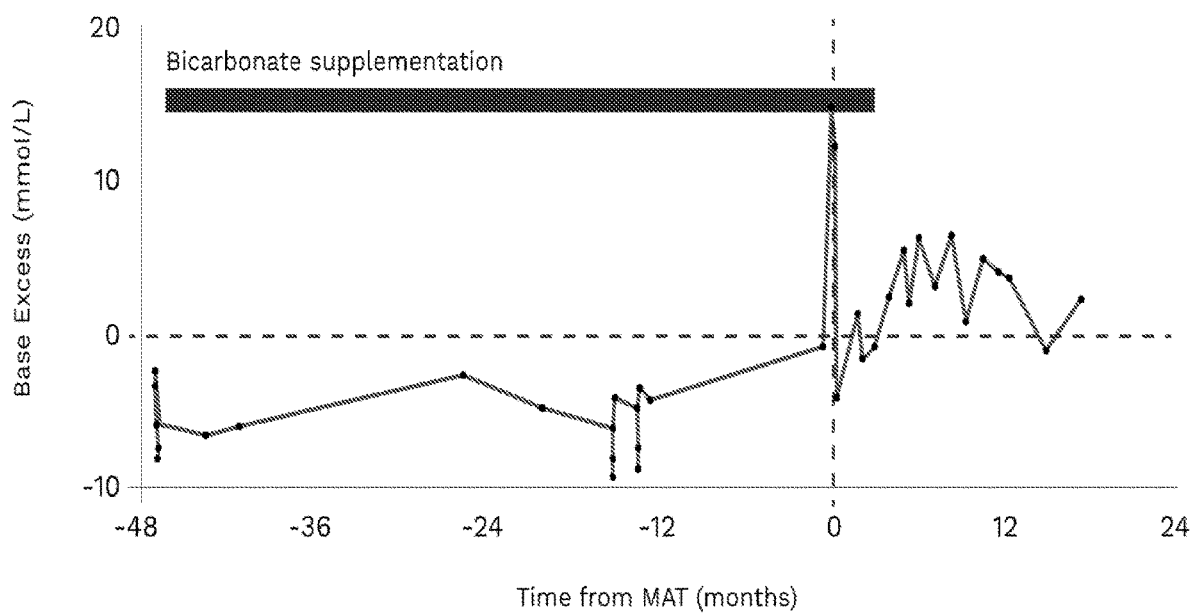
FIG. 3I is a line graph illustrating the level of blood base excess of a PS patient treated by the methods provided in the present invention as a function of time before and after therapy.

As can further be seen in FIGS. 3I, cellular treatment also resulted in pronounced improvements in the levels of blood base excess without supplementing with bicarbonate. Taken together, the data indicates that a single round of cellular treatment was also sufficient to at least prevent further deterioration in the condition of the patient.

Figure 3J:
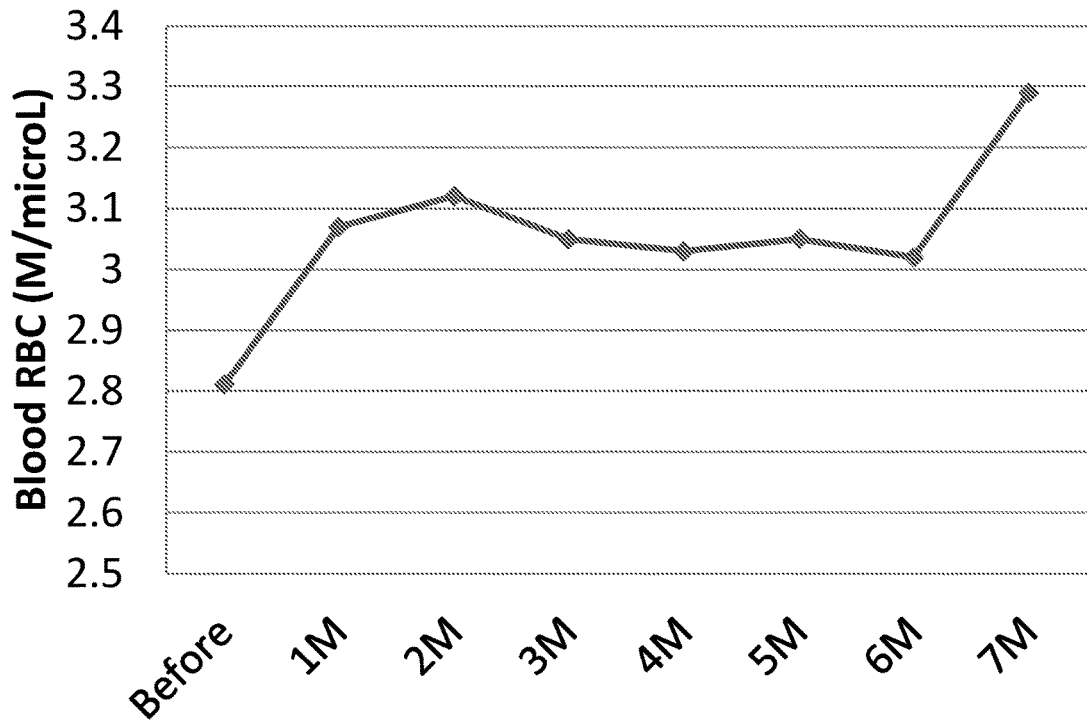
FIG. 3J is a line graph illustrating the long term elevation in blood red blood cell (RBC) levels in a PS patient before and after therapy provided by the present invention.
Figure 3K:
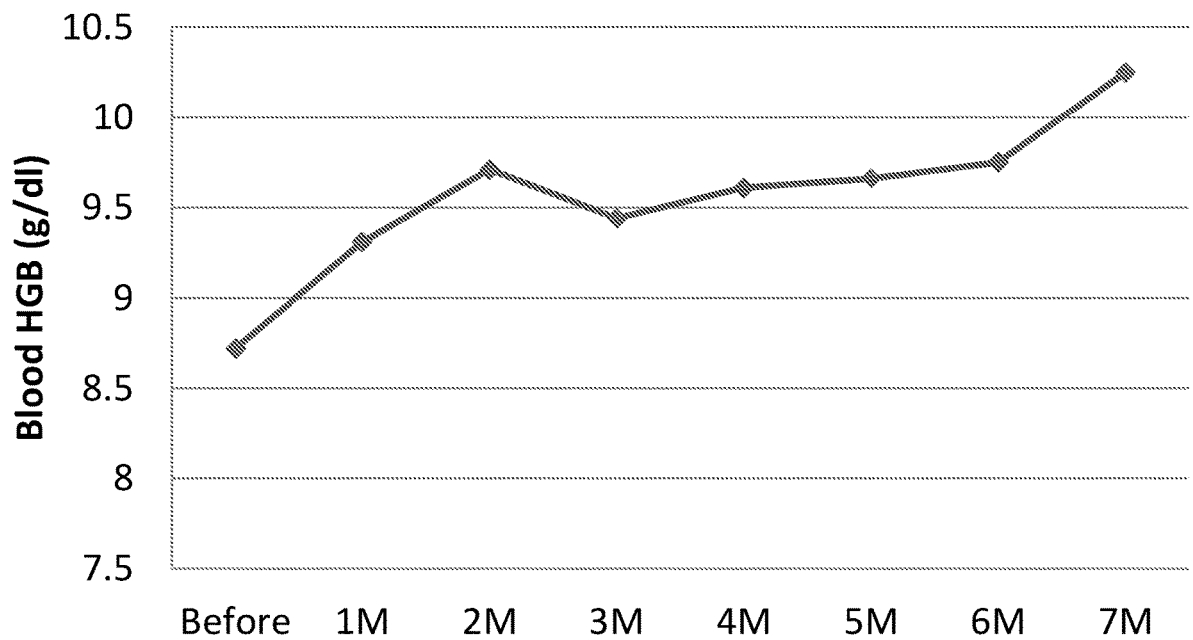
FIG. 3K is a line graph illustrating the long term elevation in blood hemoglobin (HGB) levels in a PS patient before and after therapy provided by the present invention.
Figure 3L:
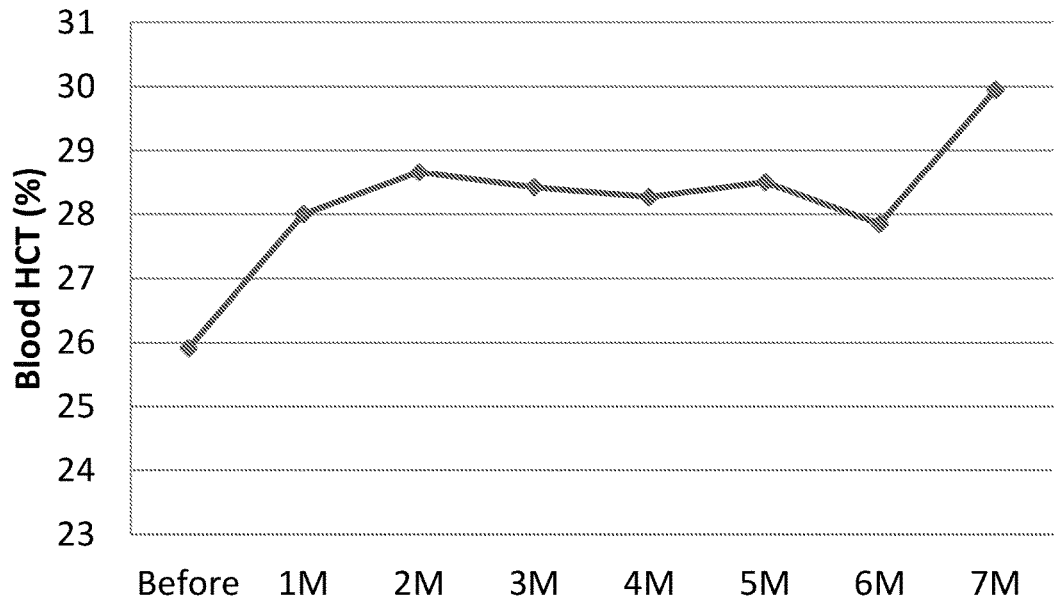
FIG. 3L is a line graph illustrating the long term elevation in blood hematocrit (HCT) levels in a PS patient before and after therapy provided by the present invention.
Figure 3M:
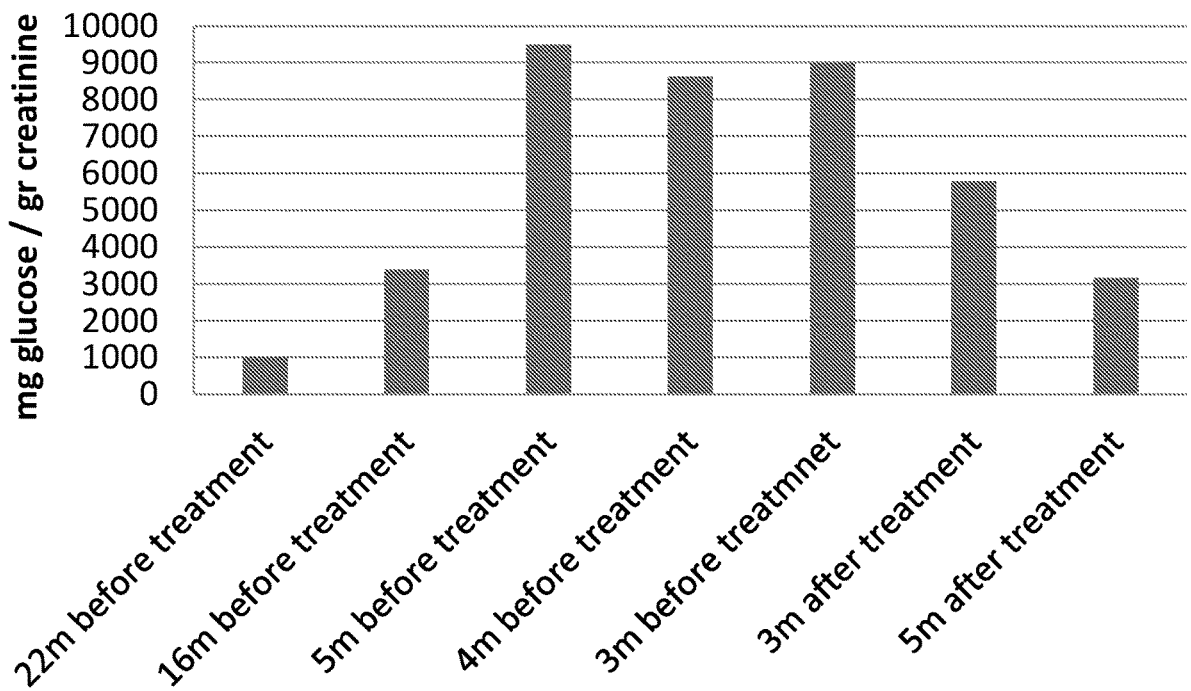
FIG. 3M is a bar graph illustrating the glucose to creatinine ratio in the urine of a PS patient treated by the methods provided in the present invention as a function of time before and after therapy.

As can be seen in FIGS. 3J-3K, treatment resulted in pronounced improvements in red blood cells levels (FIG. 3J), hemoglobin levels (FIG. 3K) and hematocrit levels (FIG. 3L). These results show that a single treatment was sufficient to ameliorate symptoms of anemia.

Figure 3N:
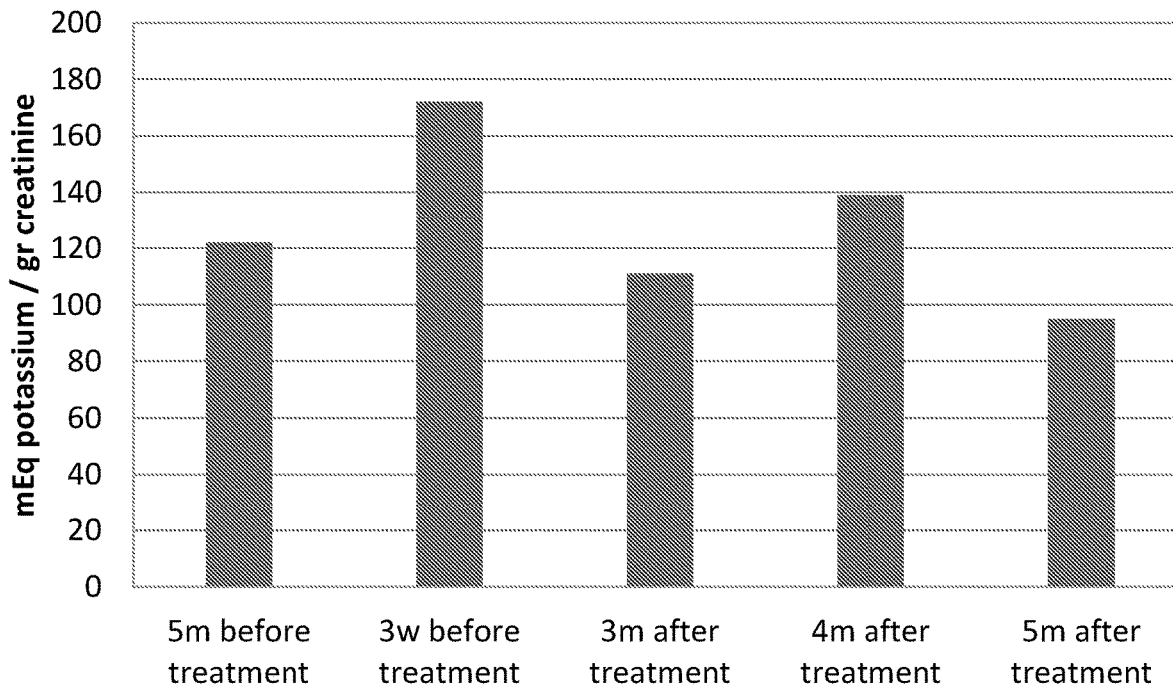
FIG. 3N is a bar graph illustrating the potassium to creatinine ratio in the urine of a PS patient treated by the methods provided in the present invention as a function of time before and after therapy.
Figure 3O:
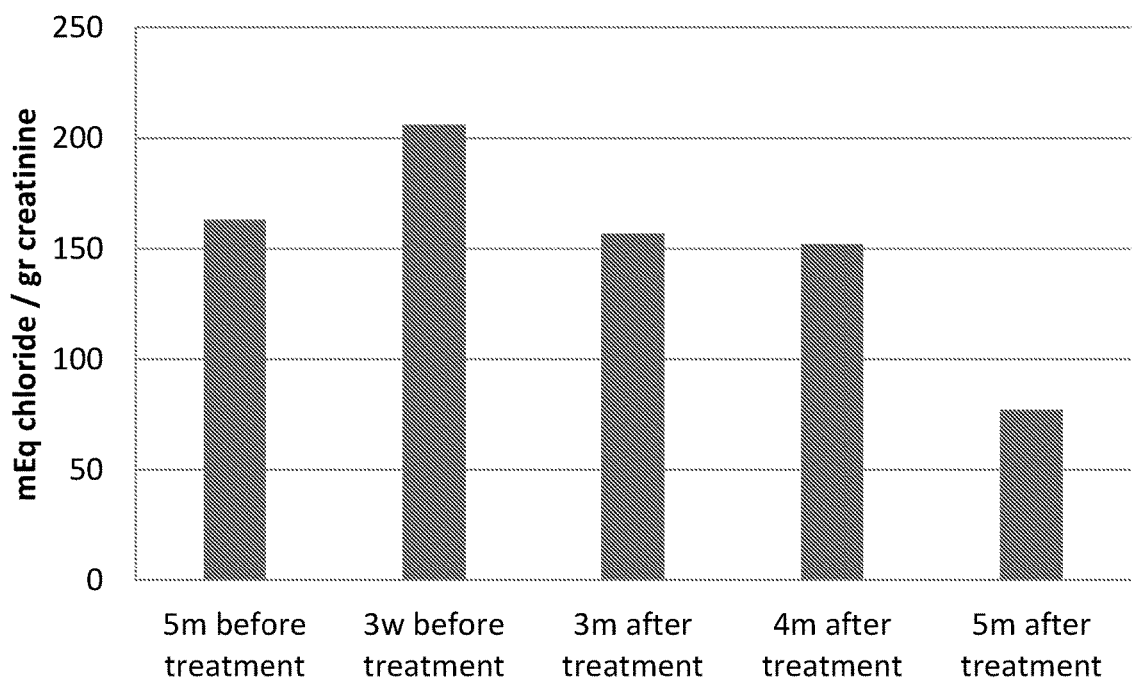
FIG. 3O is a bar graph illustrating the chloride to creatinine ratio in the urine of a PS patient treated by the methods provided in the present invention as a function of time before and after therapy.
Figure 3P:
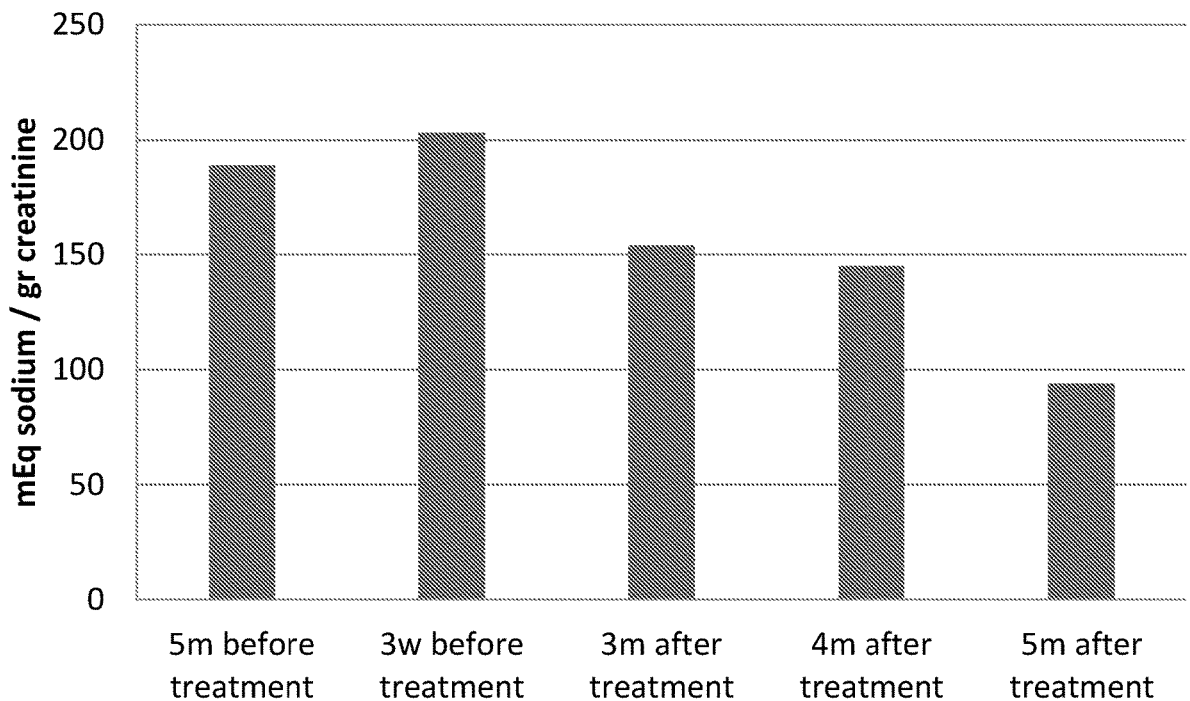
FIG. 3P is a bar graph illustrating the sodium to creatinine ratio in the urine of a PS patient treated by the methods provided in the present invention as a function of time before and after therapy.

As can be seen in FIGS. 3M-3P, a single treatment also resulted in pronounced reduction in the levels of several renal tubulopathy indicators, such as glucose levels (FIG. 3M) and certain salt levels in the urine (FIG. 3N—potassium; FIG. 3O—chloride; FIG. 3P—sodium). Taken together, the data indicates that a single round of cellular treatment was further sufficient to ameliorate symptoms of Fanconi's Syndrome.

Figure 4:
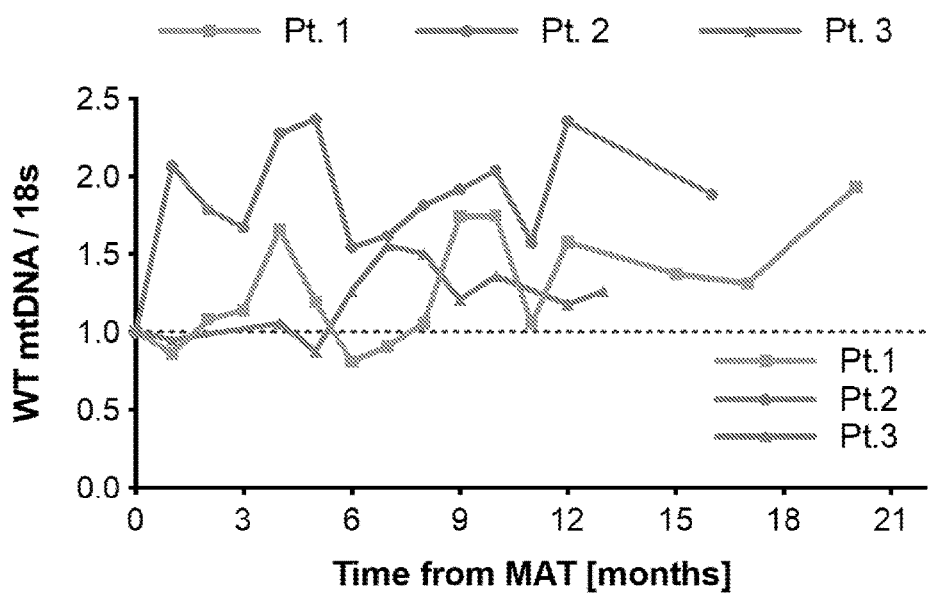
FIG. 4 is a line graph illustrating the normal mtDNA content in 3 PS patients (Pt.1, Pt.2 and Pt.3) treated by the methods provided in the present invention as a function of time before and after therapy, as measured by digital PCR for the deleted region (in each patient) compared to the 18S genomic DNA representing number of normal mtDNA per cell, and normalized per baseline.

A genetic indication to the success of the therapy used, is the prevalence of normal mtDNA compared to total mtDNA. As illustrated in FIG. 4 (Pt.1), the prevalence of normal mtDNA in the patient was increased from a baseline of about 1 to as high as 1.6 (+60%) in just 4 months, and to 1.9 (+90%) after 20 months from treatment. Notably, normal mtDNA levels were above the baseline level on most of the time points.

As the data presented above indicates, a single round of the therapeutic method provided by the present invention was successful in treating PS, FS, improving kidney function, and increasing the prevalence of normal mtDNA in peripheral blood. Evidence for such a combination of beneficial effects is further found in the patient's gain of weight, which is normal to healthy subjects of his age.

Example 5. Compassionate Treatment Using Autologous CD34+ Cells Enriched with MNV-BLD (Blood Derived Mitochondria) for a Young Patient with Pearson Syndrome (PS) and PS-Related Fanconi's Syndrome (FS).

Patient 2 was a 7-years female patient diagnosed with Pearson Syndrome, having a deletion of 4977 nucleotides in her mtDNA. The patient also suffered from anemia, endocrine pancreatic insufficiency, and is diabetic (hemoglobin A1C 7.1%). Patient has high lactate levels (>25 mg/dL), low body weight, and problems with eating and gaining weight. The patient further suffers from hypermagnesuria (high levels of magnesium in urine, low levels in blood). Patient has memory and learning problems, astigmatism, and low mitochondrial activity in peripheral lymphocytes as determined by TMRE, ATP content and 02 consumption rate (relative to the healthy mother).

Mobilization of autologous hematopoietic stem and progenitor cells (HSPC), leukapheresis and CD34 positive selection were performed similar to patient 1 (Example 4) with the addition of plerixafor (n=2) on day −1 prior to leukapheresis. Mitochondria were isolated from maternal peripheral blood mononuclear cells (PBMCs) using 250 mM sucrose buffer pH 7.4 by differential centrifugation.

For MAT, the autologous CD34+ cells were incubated with the healthy mitochondria from the patient's mother ($1*10^6$ cells per amount of mitochondria having 4.4 milli-units of citrate synthase (CS)), resulting in a 1.62 fold increase in the cells mitochondrial content (62% increase in mitochondrial DNA content as demonstrated CS activity. Incubation with mitochondria was performed for 24 hours at R.T. in saline containing 4.5% HSA. It should be noted that after mitochondrial enrichment, the CD34+ cells from the patient increased the rate of colony formation by 26%.

Figure 5A:
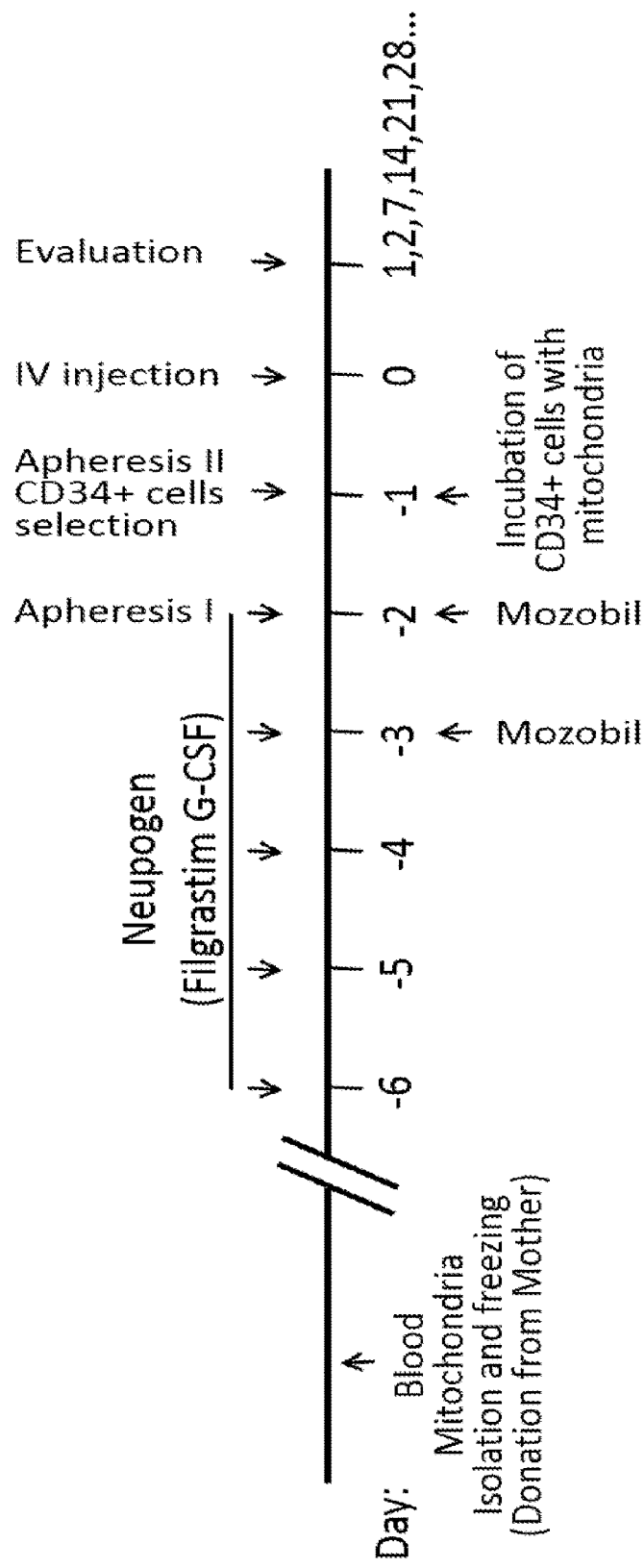
FIG. 5A is another scheme of the different stages of treatment of a Pearson Syndrome (PS) patient, as further provided by the present invention.

Patient 2 (15 KG at day of treatment) was treated by IV infusion with $1.8*10^6$ autologous CD34+ cells enriched with healthy mitochondria per kilogram body weight, according to the timeline presented in FIG. 5A.

Figure 5B:
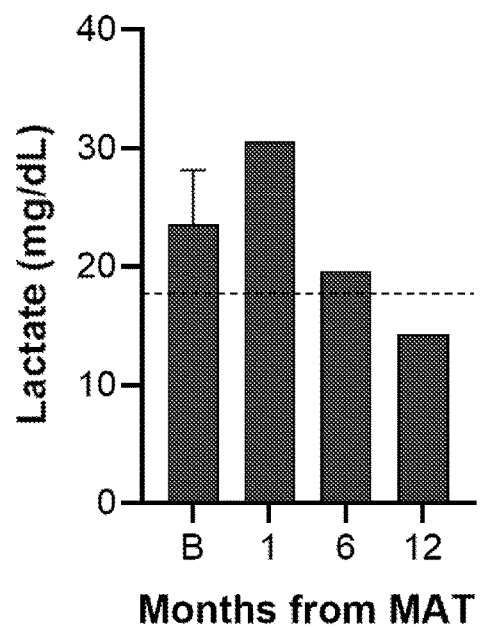
FIG. 5B is a bar graph illustrating the level of lactate in the blood of a PS patient treated by the methods provided in the present invention as a function of time before and after therapy.

FIG. 5B presents the level of lactate found in the blood of the patient as a function of time post the I.V. injection. Blood lactate is lactic acid that appears in the blood as a result of anaerobic metabolism when mitochondria are damaged or when oxygen delivery to the tissues is insufficient to support normal metabolic demands, one of the hallmarks of mitochondria dysfunction. The data teach that the level of blood lactate was significantly reduced over time.

Figure 5C:
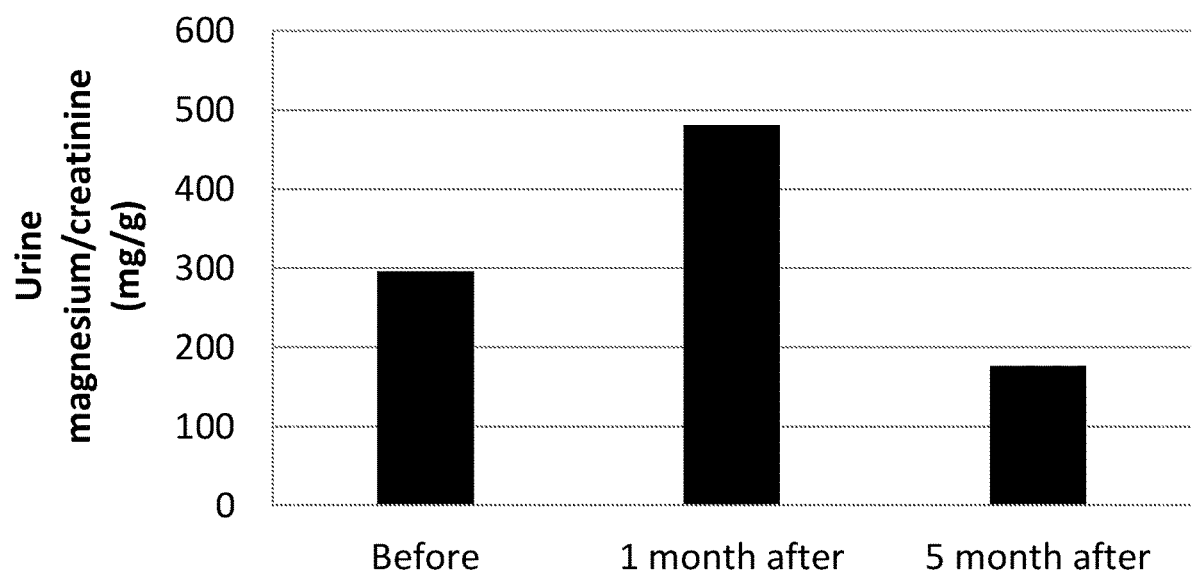
FIG. 5C is a bar graph illustrating the urine magnesium to creatinine ratio in a PS patient treated by the methods provided in the present invention as a function of time before and after therapy.
Figure 5D:
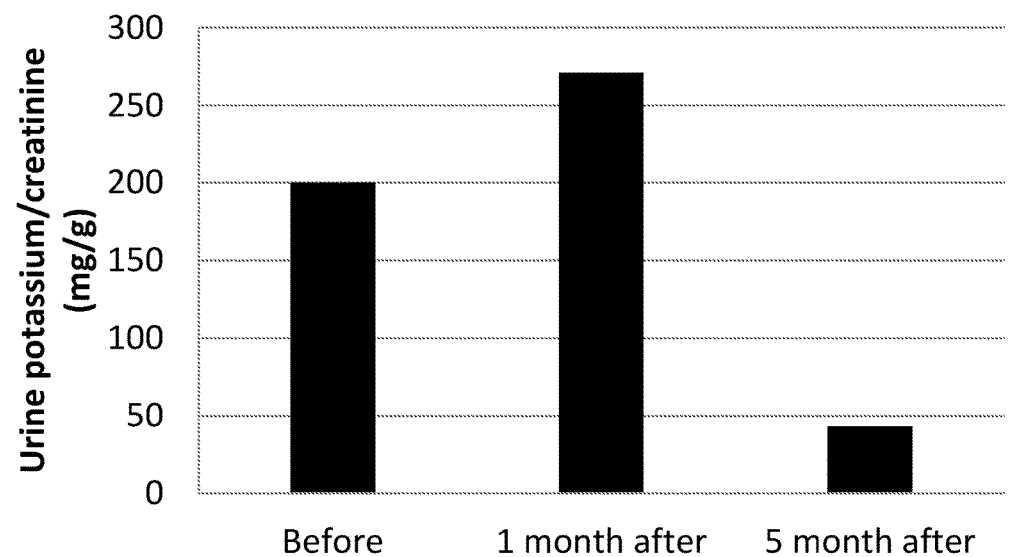
FIG. 5D is a bar graph illustrating the urine potassium to creatinine ratio in a PS patient treated by the methods provided in the present invention as a function of time before and after therapy.
Figure 5E:
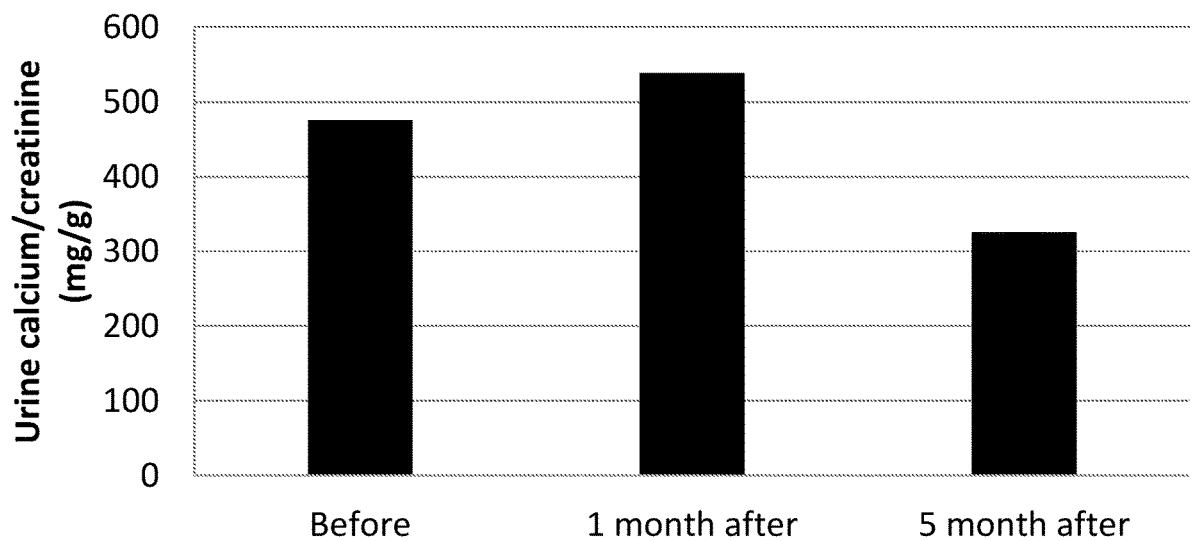
FIG. 5E is a bar graph illustrating the urine calcium to creatinine ratio in a PS patient treated by the methods provided in the present invention as a function of time before and after therapy.

FIGS. 5C, 5D and 5E present the ratios of magnesium, potassium and calcium compared to creatinine found in the urine of the patient as a function of time post the I.V. injection, respectively. The data teach that those rations were significantly reduced over time.

Figure 5F:
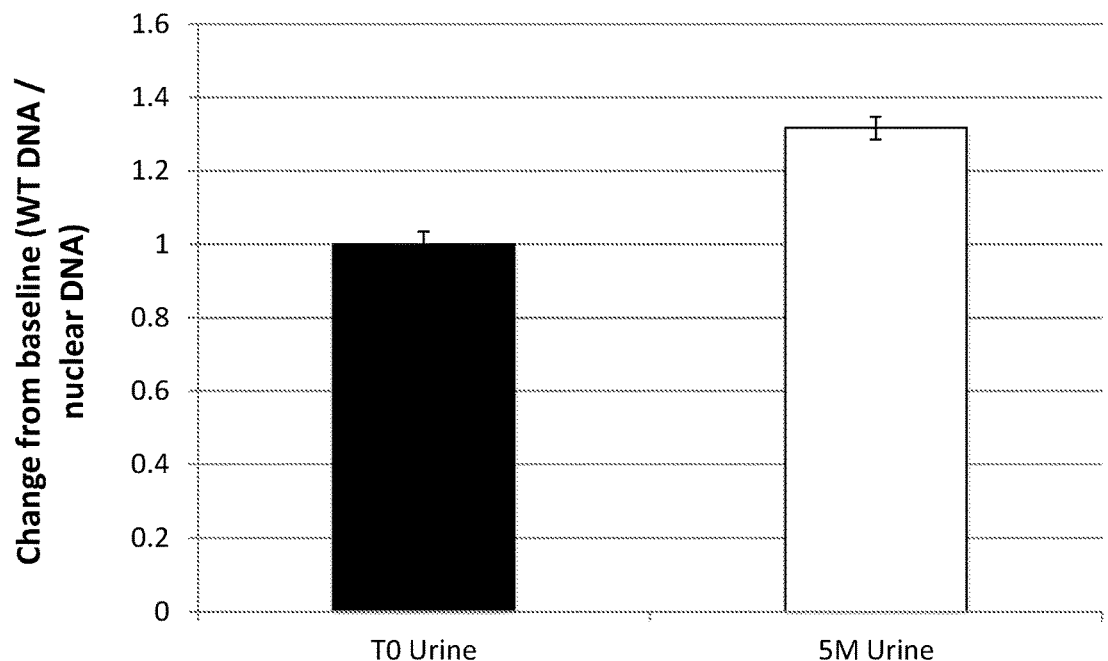
FIG. 5F is a bar graph illustrating the ATP8 to 18S copy number ratio in the urine of a PS patient treated by the methods provided in the present invention as a function of time before and after therapy.

FIG. 5F presents the genetic ratio between ATP8 to 18S in the urine of the patient as a function of time post the I.V. injection. The data teach that the patient's ATP8/18S ratio was improved over time.

Figure 5G:
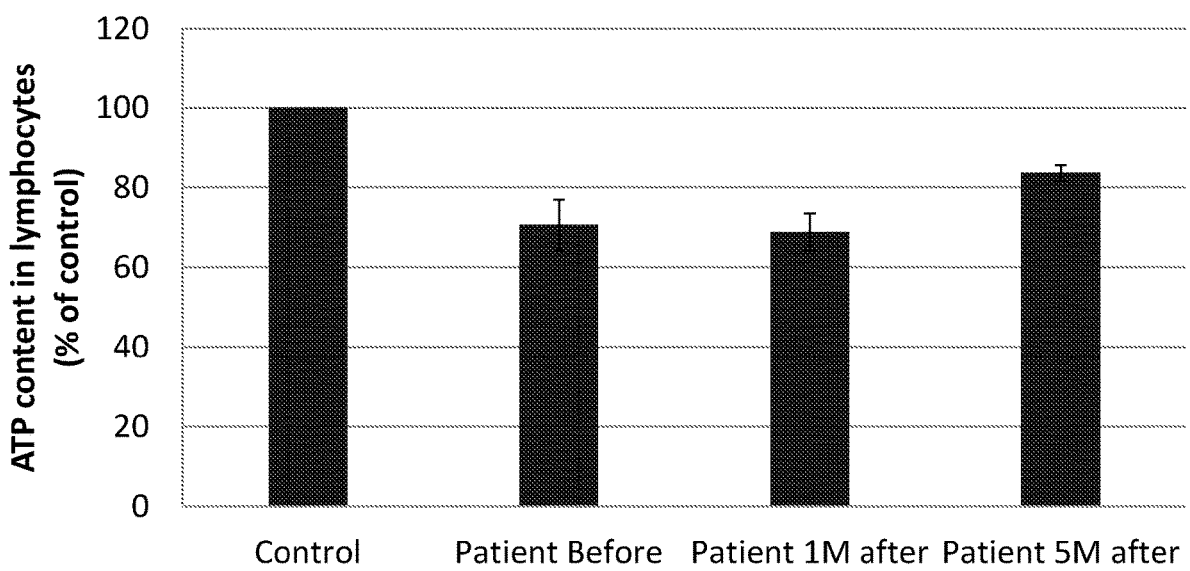
FIG. 5G is a bar graph illustrating the ATP level in lymphocytes of a PS patient treated by the methods provided in the present invention as a function of time before and after therapy.

FIG. 5G presents the ATP content in lymphocytes of the patient as a function of time post the I.V. injection. The control is the ATP content in lymphocytes of the patient's mother, which is the donor of the mitochondria. The data teach that the patient's ATP content was improved over time.

FIG. 4 (Pt.2) presents the prevalence of normal mtDNA as a function of time post the I.V. injection. As can be seen in FIG. 4 (Pt.2), the prevalence of normal mtDNA was increased from a baseline of about 1 to as high as 2 (+100%) in just 1 month, remaining relatively high until 10 months post treatment. Notably, normal mtDNA levels were above the baseline level at all time points.

Example 6. Compassionate Treatment Using Autologous CD34+ Cells Enriched with MNV-BLD (Blood Derived Mitochondria) for a Young Patient with Pearson Syndrome (PS).

Patient 3 was a 10.5-years old female patient, diagnosed with Pearson Syndrome, having a deletion of nucleotides 12113-14421 in her mtDNA. The patient also suffered from anemia, and from Fanconi's Syndrome that developed into kidney insufficiency stage 4. Patient was treated with dialysis three times a week. In the last two months, patient also suffered from a severe vision disorder, narrowing of the vision field and loss of near vision. Patient was incapable of any physical activity at all (no walking, sits in a stroller). Patient had high lactate levels (>50 mg/dL), and a pancreatic disorder which was treated with insulin. Brain MRI showed many lesions and atrophic regions. Patient was fed only through a gastrostomy. Patient had memory and learning problems. Patient had low mitochondrial activity in peripheral lymphocytes as determined by Tetramethylrhodamine, Ethyl Ester (TMRE), ATP content and $O_2$ consumption rate (relative to the healthy mother) tests.

Mobilization of autologous hematopoietic stem and progenitor cells (HSPC) as well as leukapheresis and CD34 positive selection were performed similar to patient 1 (Example 4) with the addition of plerixafor (n=1) on day −1 prior to leukapheresis. Leukapheresis was performed via a permanent dialysis catheter. Mitochondria were isolated from maternal peripheral blood mononuclear cells (PBMCs) using 250 mM sucrose buffer pH 7.4 by differential centrifugation.

For MAT, the autologous CD34+ cells were incubated with healthy mitochondria from the patient's mother ($1*10^6$ cells per amount of mitochondria having 4.4 milliunits of citrate synthase (CS)), resulting in a 1.14 fold increase in the cells mitochondrial content (14% increase in mitochondrial content as demonstrated by CS activity). Cells were incubated with mitochondria for 24 hours at R.T. in saline containing 4.5% HSA. It should be noted that after mitochondrial enrichment, the CD34+ cells from the patient increased the rate of colony formation by 52%.

Figure 6A:
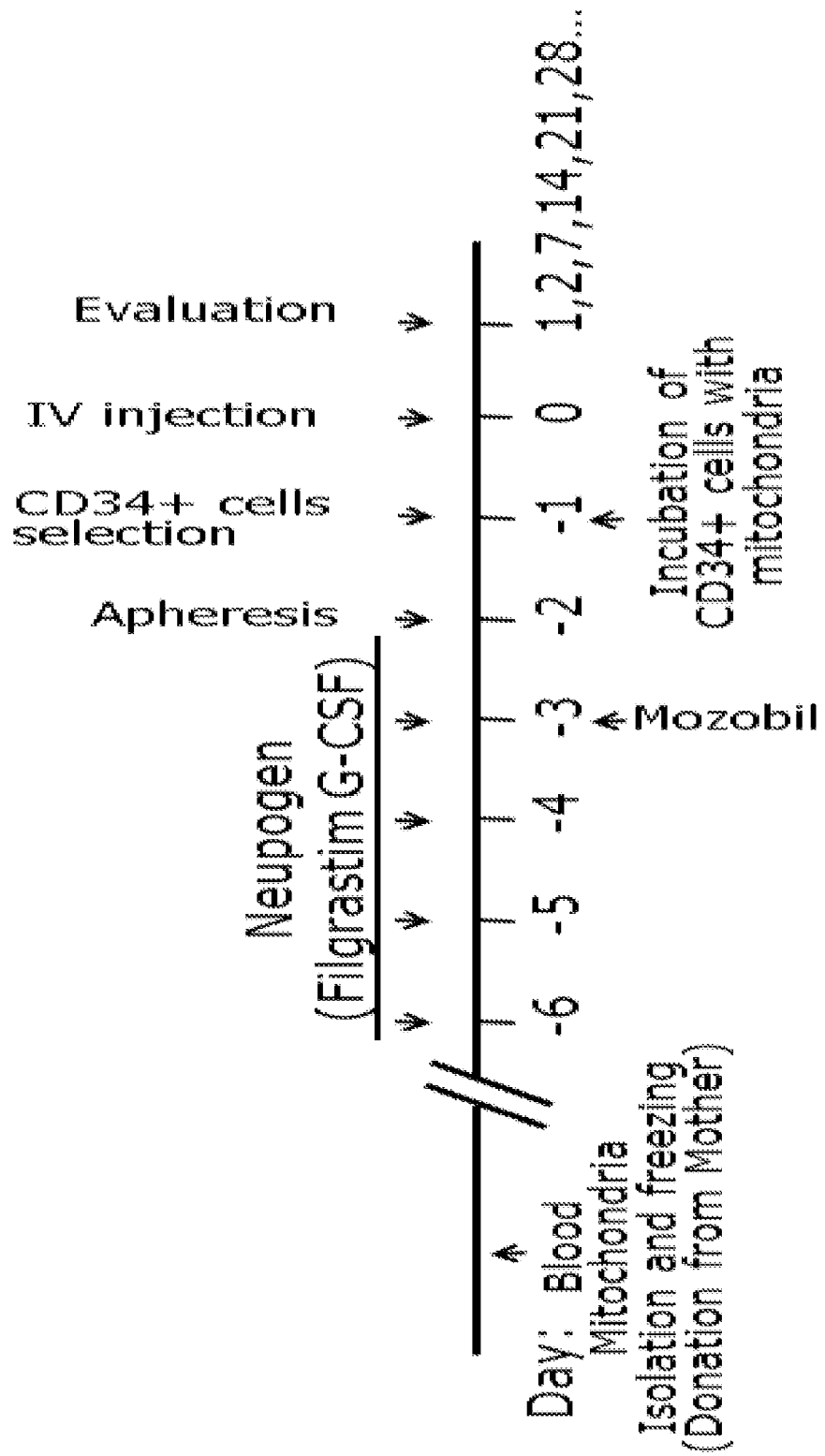
FIG. 6A is yet another scheme of the different stages of treatment of a Pearson Syndrome (PS) patient, as further provided by the present invention.

Patient 3 (21 KG) was treated by IV infusion with $2.8*10^6$ autologous CD34+ cells enriched with healthy mitochondria from her mother per kilogram body weight, according to the timeline presented in FIG. 6A.

Figure 6B:
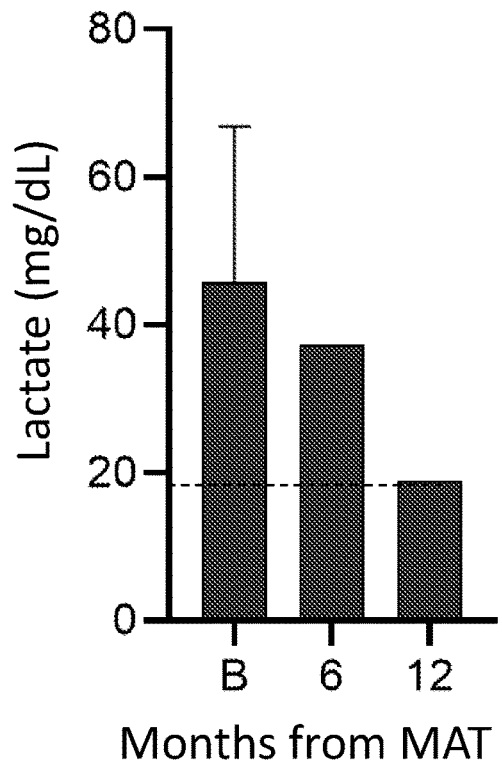
FIG. 6B is a bar graph illustrating the level of lactate in the blood of a PS patient treated by the methods provided in the present invention as a function of time before and after therapy.

FIG. 6B presents the level of lactate found in the blood of the patient as a function of time before and after therapy. The data teach that the level of blood lactate was significantly reduced over time.

FIG. 3 (Pt.3 presents the prevalence of normal mtDNA as a function of time post the I.V. injection. As can be seen in FIG. 3 (Pt.3), the prevalence of normal mtDNA was increased by 50% at 7 months post treatment. Notably, normal mtDNA levels were above the baseline level on most of the time points.

Figure 6C:
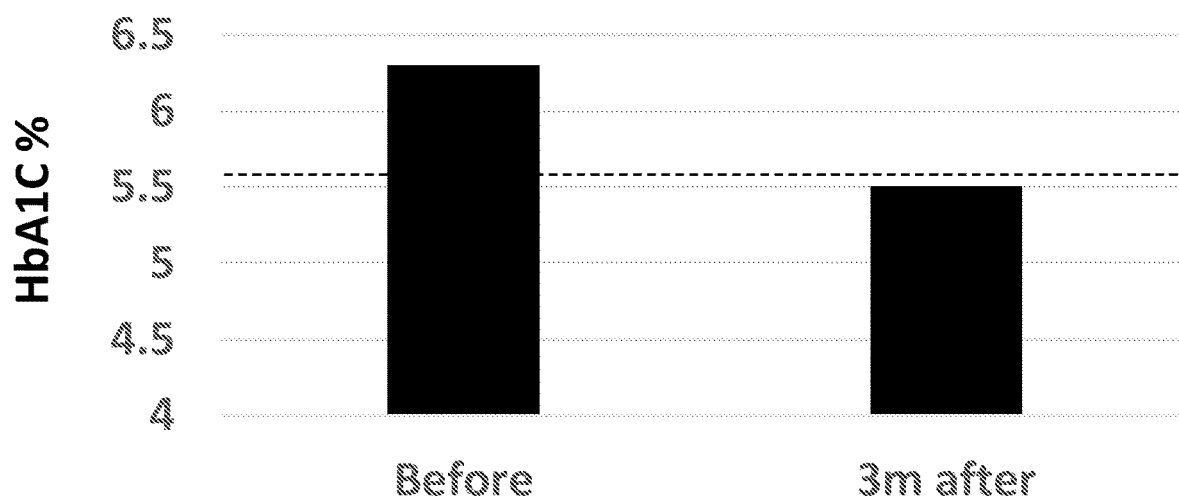
FIG. 6C is a bar graph illustrating the hemoglobin A1C (HbA1C) score of a PS patient treated by the methods provided in the present invention as a function of time before and after therapy.

Glycated hemoglobin (sometimes also referred to as hemoglobin A1c, HbA1c, A1C, Hb1c, Hb1c or HGBA1C) is a form of hemoglobin that is measured primarily to identify the three-month average plasma glucose concentration. The test is limited to a three-month average because the lifespan of a red blood cell is four months (120 days). FIG. 6C presents the result of the HbA1C test of the patient as a function of time before and after therapy.

Example 7. Mitochondrial Augmentation Therapy for Renal Diseases and Disorders.

Title: A phase I/II, open label, single dose clinical study to evaluate the safety, engraftment and therapeutic effects of transplantation of stem cells enriched with mitochondria in patients with renal diseases and disorders.

Design: All patients enrolled have a confirmed diagnosis of a renal disease or disorder. The donor of the mitochondria is confirmed as carrying no mtDNA abnormalities. Eligible patients are enrolled into the study and admitted to hospital for a short period and undergo the treatment procedure. Treatment safety, adverse events (AEs) and disease assessments are recorded throughout the duration of treatment and the post-treatment follow up period.

Treatment Doses: Therapeutic cell dose of up to $4^{\wedge}10^6$ cells/kg body weight, are transplanted by IV infusion according to the routine standard procedure at the clinical department.

Primary Safety Endpoints Assessments: Subjects are assessed for adverse events following treatment with the cells, according to CTCAE v4.03, starting enrollment.

Primary Efficacy Endpoints Assessments: Change in annual rate of metabolic crisis; Change in relative abundance of wild-type mtDNA.

Secondary Efficacy Endpoints Assessment: Systemic benefit of MNV-BM-BLD (bone marrow cells enriched with blood-derived mitochondria) and effect on distal organs (Hospitalization avoidance, Transfusion avoidance, Weight gain on standard growth curves, as compared to rate of gain in the year prior to the therapy). Additional patient-specific individualized outcomes include change in disease target organs (Renal glomerular function measured by creatinine clearance, compared to the year prior to the study; Renal tubular function, measured by serum and urine levels of potassium and magnesium; Endocrine pancreatic function as assessed by insulin requirement, C-peptide and hemoglobin A1c; Exocrine pancreatic function and rate of diarrhea; Change in Brain MRI findings compared to baseline; Change in Quality of Life (QoL) questionnaire/PEDI-CAT (Pediatric Evaluation of Disability Inventory—Computer Adaptive Test) scores).

Exploratory Efficacy Assessments: Functional Assessment (Neuromuscular function as assessed by Gross Motor Function Measure); 6-min walk test; Stress test; Developmental test; WIPSSI (Wechsler Preschool and Primary Scale of Intelligence); Memory test; Reaction time; Box and Blocks test; 30-Second Chair Stand; Standing without Support); Pathologic Assessment (Echocardiography; Bone marrow aspiration+Biopsy; Lymphocyte $O_2$ consumption, ATP content, TMRE/MTG).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The invention claimed is:

1. A method of treating a renal disease or disorder or symptom thereof in a human patient in need of such treatment, the method comprising parenterally administering to the patient a pharmaceutical composition comprising at least about $5\times10^5$ to $5\times10^9$ human stem cells enriched with human exogenous mitochondria, wherein the renal disease or disorder is not a primary mitochondrial disease or disorder caused by a pathogenic mutation in mitochondrial DNA or by a pathogenic mutation in nuclear DNA encoding a mitochondrial protein, and wherein the administration of the pharmaceutical composition improves kidney functions and arrests renal deterioration.

2. The method of claim 1, wherein the exogenous mitochondria are syngeneic or allogeneic.

3. The method of claim 1, wherein the disease or disorder is selected from the group consisting of nephropathy, nephritis, nephrosis, nephritic syndrome, nephrotic syndrome, Fanconi's syndrome and kidney failure.

4. The method of claim 1, wherein the symptom is selected from the group consisting of low blood alkaline phosphatase levels, low blood magnesium levels, high blood creatinine levels, low blood bicarbonate levels, low blood base excess levels, high urine glucose/creatinine ratios, high urine chloride/creatinine ratios, high urine sodium/creatinine ratios, high blood lactate levels, high urine magnesium/creatinine ratios, high urine potassium/creatinine ratios, high urine calcium/creatinine ratios and high blood urea levels.

5. The method of claim 1, wherein the mitochondrially-enriched human stem cells have at least one of:
   (i) an increased mitochondrial DNA content;
   (ii) an increased level of citrate synthase (CS) activity;
   (iii) an increased content of at least one mitochondrial protein selected from SDHA and COX1;
   (iv) an increased rate of O2 consumption;
   (v) an increased rate of ATP production; or
   (vi) any combination thereof, relative to the corresponding level in the stem cells prior to mitochondrial enrichment.

6. The method of claim 1, wherein the human stem cells are hematopoietic stem cells, mesenchymal stem cells, pluripotent stem cells (PSCs), induced pluripotent stem cells (iPSCs), or CD34$^+$ cells.

7. The method of claim 1, wherein the human stem cells are isolated, derived or obtained from cells of the bone marrow, adipose tissue, oral mucosa, skin fibroblasts, blood or umbilical cord blood.

8. The method of claim 1, wherein the human exogenous mitochondria are isolated or obtained from placenta, placental cells grown in culture or blood cells.

9. The method of claim 1, wherein the human exogenous mitochondria constitute at least 1-30% of the total mitochondria in the mitochondrially enriched human stem cells.

10. The method of claim 9, wherein the human exogenous mitochondria constitute at least 1%, 3%, 5%, 10%, 15%, 20%, 25% or 30% of the total mitochondria in the mitochondrially enriched human stem cells.

11. The method of claim 1, wherein the composition further comprises non-enriched stem cells, megakaryocytes, erythrocytes, mast cells, myeloblasts, basophils, neutrophils, eosinophils, monocytes, macrophages, natural killer (NK) cells, small lymphocytes, T lymphocytes, B lymphocytes, plasma cells, reticular cells, or any combination thereof.

12. The method of claim 1, wherein said administering the pharmaceutical composition is directly to the renal system.

13. The method of claim 1, wherein said administering the pharmaceutical composition is by systemic administration.

14. The method of claim 1, wherein the human stem cells are obtained or derived from the patient before enrichment with the exogenous mitochondria.

15. The method of claim 1, wherein the human stem cells are obtained or derived from a donor different than the patient before enrichment with the exogenous mitochondria.

16. The method of claim 15, wherein the donor is at least partly HLA-matched with the patient.

17. The method of claim 15, further comprising a step of administering to the patient an agent which prevents, delays, minimizes or abolishes an adverse immunogenic reaction between the patient and the mitochondrially-enriched human stem cells.

18. The method of claim 17, wherein the adverse immunogenic reaction is a graft-versus-host disease (GvHD).

19. The method of claim 1, further comprising administering to the subject non-enriched stem cells, megakaryocytes, erythrocytes, mast cells, myeloblasts, basophils, neutrophils, eosinophils, monocytes, macrophages, natural killer (NK) cells, small lymphocytes, T lymphocytes, B lymphocytes, plasma cells, reticular cells, or any combination thereof.

20. The method of claim 5, wherein increased mitochondrial DNA content is from endogenous and/or exogenous mitochondria.

21. The method of claim 10, wherein the human exogenous mitochondria constitute at least 1% of the total mitochondria in the mitochondrially enriched human stem cells.

* * * * *